(12) United States Patent
Schaffer et al.

(10) Patent No.: US 12,310,997 B2
(45) Date of Patent: May 27, 2025

(54) COMPOSITIONS AND METHODS OF TREATING OCULAR DISEASES

(71) Applicant: The Regents of the University of California, Oakland, CA (US)

(72) Inventors: David V. Schaffer, Danville, CA (US); Leah C. Byrne, San Francisco, CA (US); Timothy P. Day, Berkeley, CA (US); John G. Flannery, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/167,598

(22) Filed: Feb. 10, 2023

(65) Prior Publication Data
US 2024/0091378 A1    Mar. 21, 2024

Related U.S. Application Data

(63) Continuation of application No. 16/486,681, filed as application No. PCT/US2018/040115 on Jun. 28, 2018, now abandoned.

(60) Provisional application No. 62/535,042, filed on Jul. 20, 2017, provisional application No. 62/527,871, filed on Jun. 30, 2017.

(51) Int. Cl.
| | |
|---|---|
| *C12N 15/861* | (2006.01) |
| *A61K 9/00* | (2006.01) |
| *A61K 35/761* | (2015.01) |
| *A61K 48/00* | (2006.01) |
| *A61P 27/02* | (2006.01) |
| *C07K 7/06* | (2006.01) |
| *C07K 7/08* | (2006.01) |
| *C07K 14/075* | (2006.01) |
| *C12N 9/22* | (2006.01) |
| *C12N 15/10* | (2006.01) |
| *C12N 15/11* | (2006.01) |
| *C12N 15/113* | (2010.01) |
| *C12N 15/86* | (2006.01) |
| *C12N 15/90* | (2006.01) |

(52) U.S. Cl.
CPC .......... *A61K 35/761* (2013.01); *A61K 9/0048* (2013.01); *A61K 48/0041* (2013.01); *A61K 48/0075* (2013.01); *A61P 27/02* (2018.01); *C07K 7/06* (2013.01); *C07K 7/08* (2013.01); *C07K 14/075* (2013.01); *C12N 9/22* (2013.01); *C12N 15/1082* (2013.01); *C12N 15/11* (2013.01); *C12N 15/113* (2013.01); *C12N 15/86* (2013.01); *C12N 15/902* (2013.01); *C12N 2310/20* (2017.05); *C12N 2750/14122* (2013.01); *C12N 2750/14142* (2013.01); *C12N 2750/14143* (2013.01); *C12N 2750/14145* (2013.01); *C12N 2750/14171* (2013.01); *C12N 2800/80* (2013.01)

(58) Field of Classification Search
CPC ....... C12N 15/861; A61K 35/761; C07K 7/06
See application file for complete search history.

(56) References Cited

U.S. PATENT DOCUMENTS

| | | |
|---|---|---|
| 5,773,700 A | 6/1998 | Grinsven et al. |
| 6,096,548 A | 8/2000 | Stemmer |
| 6,482,634 B1 | 11/2002 | Wilson et al. |
| 6,491,907 B1 | 12/2002 | Rabinowitz et al. |
| 6,596,539 B1 | 7/2003 | Stemmer et al. |
| 6,703,237 B2 | 3/2004 | Samulski et al. |
| 6,710,036 B2 | 3/2004 | Kurtzman et al. |
| 6,733,757 B2 | 5/2004 | Patel et al. |
| 6,855,314 B1 | 2/2005 | Chiorini et al. |
| 6,943,153 B1 | 9/2005 | Manning, Jr. et al. |
| 6,962,815 B2 | 11/2005 | Bartlett |
| 7,172,893 B2 | 2/2007 | Rabinowitz et al. |
| 7,252,997 B1 | 8/2007 | Hallek et al. |
| 7,254,489 B2 | 8/2007 | Mossel |
| 7,285,381 B1 | 10/2007 | Hallek et al. |
| 7,314,912 B1 | 1/2008 | Hallek et al. |
| 7,368,428 B2 | 5/2008 | Serrero |
| 7,427,396 B2 | 9/2008 | Arbetman et al. |
| 7,556,965 B2 | 7/2009 | Hallek et al. |

(Continued)

FOREIGN PATENT DOCUMENTS

| | | |
|---|---|---|
| AU | 2014331708 | 5/2016 |
| CA | 2379220 | 1/2001 |

(Continued)

OTHER PUBLICATIONS

Khabou et al. (2016) "Insight into the mechanisms of enhanced retinal transduction by the engineered AAV2 capsid variant—7m8" Biotechnology and bioengineering, 113(12), 2712-2724. (Year: 2016).*
Dalkara et al. (2013) "In vivo-directed evolution of a new adeno-associated virus for therapeutic outer retinal gene delivery from the vitreous" Science translational medicine, 5(189), 189ra76, 11 pages. (Year: 2013).*
Adachi, et al.; "A New Recombinant Adeno-Associated Virus (AAV)-Based Random Peptide Display Library System: Infection-Defective AAV1.9-3 as a Novel Detargeted Platform for Vector Evolution"; Gene Therapy and Regulation; vol. 5, No. 1, pp. 31-55 (Oct. 2010).

(Continued)

*Primary Examiner* — Teresa E Knight
*Assistant Examiner* — James Joseph Graber
(74) *Attorney, Agent, or Firm* — Shweta Chandra; Bozicevic, Field & Francis LLP

(57) ABSTRACT

The present disclosure provides recombinant adeno-associated virus (AAV) virions with altered capsid protein, where the recombinant AAV (rAAV) virions exhibit greater ability to cross barriers between intravitreal fluid and retinal cells, and thus greater infectivity of a retinal cell compared to wild-type AAV, and where the rAAV virions comprise a heterologous nucleic acid. The present disclosure provides methods of delivering a gene product to a retinal cell in an individual.

16 Claims, 39 Drawing Sheets
Specification includes a Sequence Listing.

(56) References Cited

U.S. PATENT DOCUMENTS

| | | |
|---|---|---|
| 7,629,322 B2 | 12/2009 | Kleinschmidt et al. |
| 7,749,492 B2 | 7/2010 | Bartlett et al. |
| 7,892,809 B2 | 2/2011 | Bowles et al. |
| 7,968,340 B2 | 6/2011 | Hallek et al. |
| 8,263,396 B2 | 9/2012 | Xiao |
| 8,524,446 B2 | 9/2013 | Gao et al. |
| 8,574,583 B2 | 11/2013 | Kay et al. |
| 8,632,764 B2 | 1/2014 | Xiao et al. |
| 8,663,624 B2 | 3/2014 | Schaffer et al. |
| 9,193,956 B2 | 11/2015 | Schaffer et al. |
| 9,233,131 B2 | 1/2016 | Schaffer et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 9,587,282 B2 | 3/2017 | Schaffer et al. |
| 9,856,539 B2 | 1/2018 | Schaffer et al. |
| 9,909,142 B2 | 3/2018 | Yazicioglu et al. |
| 10,046,016 B2 | 8/2018 | Schaffer et al. |
| 10,202,657 B2 | 2/2019 | Schaffer et al. |
| 10,214,566 B2 | 2/2019 | Schaffer et al. |
| 10,214,785 B2 | 2/2019 | Schaffer et al. |
| 10,494,612 B2 | 12/2019 | Schaffer et al. |
| 10,738,326 B2 | 8/2020 | Muramatsu |
| 10,883,117 B2 | 1/2021 | Ojala et al. |
| 10,961,282 B2 | 3/2021 | Dudman et al. |
| 11,021,519 B2 | 6/2021 | Chalberg et al. |
| 11,136,557 B2 | 10/2021 | Schaffer et al. |
| 11,167,041 B2 | 11/2021 | Kim et al. |
| 11,236,402 B2 | 2/2022 | Schaffer et al. |
| 11,554,180 B2 | 1/2023 | Schaffer et al. |
| 11,565,000 B2 | 1/2023 | Schaffer et al. |
| 11,565,001 B2 | 1/2023 | Schaffer et al. |
| 11,634,691 B2 | 4/2023 | Schaffer et al. |
| 11,680,249 B2 | 6/2023 | Schaffer et al. |
| 2002/0136710 A1 | 9/2002 | Samulskl et al. |
| 2002/0155610 A1 | 10/2002 | Colosi |
| 2002/0192823 A1 | 12/2002 | Bartlett |
| 2002/0192853 A1 | 12/2002 | Behammer |
| 2003/0138772 A1 | 7/2003 | Gao et al. |
| 2003/0143732 A1 | 7/2003 | Fosnaugh et al. |
| 2003/0149235 A1 | 8/2003 | Baker et al. |
| 2003/0171254 A1 | 9/2003 | Sasaki et al. |
| 2003/0228284 A1 | 12/2003 | McCown et al. |
| 2004/0180440 A1 | 9/2004 | Zolotukhin |
| 2005/0019927 A1 | 1/2005 | Hildinger et al. |
| 2005/0053922 A1 | 3/2005 | Schaffer |
| 2005/0089973 A1 | 4/2005 | Yocum et al. |
| 2005/0106558 A1 | 5/2005 | Perabo et al. |
| 2005/0148069 A1 | 7/2005 | Gage et al. |
| 2005/0220766 A1 | 10/2005 | Amalfitano et al. |
| 2005/0287122 A1 | 12/2005 | Bartlett et al. |
| 2006/0051333 A1 | 3/2006 | Arbetman et al. |
| 2006/0127358 A1 | 6/2006 | Muzyczka et al. |
| 2006/0188483 A1 | 8/2006 | Rabinowitz et al. |
| 2006/0292117 A1 | 12/2006 | Loiler et al. |
| 2007/0020624 A1 | 1/2007 | Rubenfield et al. |
| 2007/0036760 A1 | 2/2007 | Wilson et al. |
| 2007/0172460 A1 | 7/2007 | Kleinschmidt et al. |
| 2007/0196338 A1 | 8/2007 | Samulski et al. |
| 2008/0269149 A1 | 10/2008 | Bowles et al. |
| 2009/0202490 A1 | 8/2009 | Schaffer et al. |
| 2010/0166729 A9 | 7/2010 | Madison et al. |
| 2010/0172871 A1 | 7/2010 | Flannery et al. |
| 2011/0104120 A1 | 5/2011 | Xiao et al. |
| 2011/0171262 A1 | 7/2011 | Bakker et al. |
| 2011/0236353 A1 | 9/2011 | Wilson et al. |
| 2012/0093772 A1 | 4/2012 | Horsager et al. |
| 2012/0164106 A1 | 6/2012 | Schaffer et al. |
| 2013/0323302 A1 | 12/2013 | Constable et al. |
| 2014/0242031 A1 | 8/2014 | Schaffer et al. |
| 2014/0294771 A1 | 10/2014 | Schaffer et al. |
| 2014/0364338 A1 | 12/2014 | Schaffer et al. |
| 2015/0118201 A1 | 4/2015 | Xiao et al. |
| 2015/0132262 A1 | 5/2015 | Schaffer et al. |
| 2015/0152142 A1 | 6/2015 | Asokan et al. |
| 2015/0225702 A1 | 8/2015 | Schaffer et al. |
| 2015/0232953 A1 | 8/2015 | Schaffer et al. |
| 2015/0315610 A1 | 11/2015 | Nishie et al. |
| 2016/0017295 A1 | 1/2016 | Schaffer et al. |
| 2016/0102324 A1 | 4/2016 | Duchateau et al. |
| 2016/0184394 A1 | 6/2016 | Schaffer et al. |
| 2016/0340393 A1 | 11/2016 | Schaffer et al. |
| 2016/0375151 A1 | 12/2016 | Schaffer et al. |
| 2016/0376323 A1 | 12/2016 | Schaffer et al. |
| 2017/0044504 A1 | 2/2017 | Schaffer et al. |
| 2017/0096683 A1 | 4/2017 | Scaria et al. |
| 2018/0066285 A1 | 3/2018 | Ojala et al. |
| 2018/0289757 A1 | 10/2018 | Schaffer et al. |
| 2019/0169237 A1 | 6/2019 | Schaffer et al. |
| 2019/0218627 A1 | 7/2019 | Schaffer et al. |
| 2019/0255192 A1 | 8/2019 | Kirn et al. |
| 2019/0300579 A1 | 10/2019 | Dudman et al. |
| 2020/0095559 A1 | 3/2020 | Schaffer et al. |
| 2020/0231942 A1 | 7/2020 | Schaffer et al. |
| 2021/0077552 A1 | 3/2021 | Schaffer et al. |
| 2021/0147876 A1 | 5/2021 | Ojala et al. |
| 2021/0283274 A1 | 9/2021 | Schaffer et al. |
| 2022/0017876 A1 | 1/2022 | Schaffer et al. |
| 2022/0243291 A1 | 8/2022 | Schaffer et al. |
| 2022/0331450 A1 | 10/2022 | Schaffer et al. |
| 2022/0331451 A1 | 10/2022 | Schaffer et al. |
| 2022/0362409 A1 | 11/2022 | Schaffer et al. |
| 2022/0389390 A1 | 12/2022 | Schaffer et al. |
| 2023/0321282 A1 | 10/2023 | Schaffer et al. |
| 2023/0323311 A1 | 10/2023 | Schaffer et al. |

FOREIGN PATENT DOCUMENTS

| | | |
|---|---|---|
| CN | 1325451 A | 12/2001 |
| CN | 1826414 A | 8/2006 |
| CN | 1966082 A | 5/2007 |
| CN | 101484005 A | 7/2009 |
| CN | 101532024 A | 9/2009 |
| CN | 103561774 A | 2/2014 |
| CN | 106232618 A | 10/2014 |
| JP | 2008-523813 A | 7/2008 |
| WO | WO 1997/038723 | 10/1997 |
| WO | WO 1999/067393 | 12/1999 |
| WO | WO 2000/028004 | 5/2000 |
| WO | WO 2001/070276 | 9/2001 |
| WO | WO 2002/053703 | 7/2002 |
| WO | WO 2003/018820 | 3/2003 |
| WO | WO 2003/023032 | 3/2003 |
| WO | WO 2003/054197 | 7/2003 |
| WO | WO 2003/093436 | 11/2003 |
| WO | WO 2004/083441 | 9/2004 |
| WO | WO2004083411 A1 | 9/2004 |
| WO | WO 2004/108922 | 12/2004 |
| WO | WO 2004/112727 | 12/2004 |
| WO | WO 2005/005610 | 1/2005 |
| WO | WO 2005/033321 | 4/2005 |
| WO | WO 2006/066066 | 6/2006 |
| WO | WO 2006/110689 | 10/2006 |
| WO | WO 2007/120542 | 10/2007 |
| WO | WO 2008/131951 | 11/2008 |
| WO | WO 2009/137006 | 11/2009 |
| WO | WO 2009/154452 | 12/2009 |
| WO | WO 2010/093784 | 8/2010 |
| WO | WO 2010/138263 | 12/2010 |
| WO | WO 2011/117258 | 9/2011 |
| WO | WO 2012/145601 | 10/2012 |
| WO | WO 2013/029030 | 2/2013 |
| WO | WO 2013/170078 | 11/2013 |
| WO | WO 2013/173512 | 11/2013 |
| WO | WO 2014/124282 | 8/2014 |
| WO | WO 2014/194132 | 12/2014 |
| WO | WO 2014/207190 | 12/2014 |
| WO | WO 2014200910 | 12/2014 |
| WO | WO2015012501 A1 | 1/2015 |
| WO | WO 2015/048534 | 4/2015 |
| WO | WO 2015/054653 | 4/2015 |
| WO | WO 2015/121501 | 8/2015 |
| WO | WO 2015/142941 | 9/2015 |
| WO | WO 2015/191693 | 12/2015 |

(56) References Cited

FOREIGN PATENT DOCUMENTS

| WO | WO2016034375 A1 | 3/2016 |
|---|---|---|
| WO | WO 2016/134375 | 8/2016 |
| WO | WO 2016/141078 | 9/2016 |
| WO | WO 2016/144892 | 9/2016 |
| WO | WO 2017/023724 | 2/2017 |
| WO | WO 2017/197355 | 11/2017 |
| WO | WO 2019/046069 | 3/2019 |

OTHER PUBLICATIONS

Akiyama, et al.; "Intraocular Injection of an Aptamer that Binds PDGF-B: A Potential Treatment for Proliferative Retinopathies"; Journal of Cellular Physiology; vol. 207, pp. 407-412 (2006).
Ali, et al.; "Restoration of photoreceptor ultrastructure and function in retinal degeneration slow mice by gene therapy"; Nature Genetics; vol. 25, pp. 306-310 (Jul. 2000).
Allocca, et al.; "Novel adeno-associated virus serotypes efficiently transduce murine photoreceptors"; Journal of Virology; vol. 81, No. 20, pp. 11372-11380 (Oct. 2007).
Asokan, et al., "Reengineering a receptor footprint of adeno-associated virus enables selective and systemic gene transfer to muscle"; Nat Biotechnol; vol. 28, No. 1, pp. 79-82 (Jan. 2010).
Asuri, et al.; "Directed Evolution of Adena-associated Virus for Enhanced Gene Delivery and Gene Targeting in Human Pluripotent Stem Cells"; Molecular Therapy, vol. 20, No. 2, pp. 329-338 (Feb. 1, 2012).
Bichsel, et al.; "Bacterial delivery of nuclear proteins into pluripotent and differentiated cells"; PLoS One; vol. 6, No. 1, pp. 1-9 (Jan. 2011).
Blacklow, et al.; "A Seroepidemiologic Study of Adenovirus-Associated Virus Infection in Infants and Children"; Am J Epidemiol.; vol. 94, No. 4, pp. 359-366 (Oct. 1971).
Boucas, et al.; "Engineering adeno-associated virus serotype 2-based targeting vectors using a new insertion site-position 453-and single point mutations"; J Gene Med.; vol. 11, No. 12, pp. 1103-1113 (Dec. 2009).
Buch, et al., "in Contrast to AAC-Mediated Cntf Expression, AAV-Mediated Gdnf Expression Enhances Gene Replacement Therapy in Rodent Models of Retinal Degeneration"; Molecular Therapy; vol. 14, No. 5, pp. 700-709 (Nov. 2006).
Buning, et al., "Receptor targeting of adeno-associated virus vectors"; Gene Therapy; vol. 10, pp. 1142-1151 (2003).
Chadderton, et al.; "Improved Retinal Function in a Mouse Model of Dominant Retinitis Pigmentosa Following AAV-delivered Gene Therapy"; Molecular Therapy; vol. 17, No. 4, pp. 593-599 (Apr. 2009).
Choi, et al.; "AAV Hybrid Serotypes: Improved Vectors for Gene Delivery."; Current Gene Therapy; vol. 5, No. 3, pp. 299-310 (Jun. 2005).
Cronin, et al.; "Efficient transduction and optogenetic stimulation of retinal bipolar cells by a synthetic adeno-associated virus capsid and promoter"; EMBO Molecular Medicine; 16 pages (2014).
Dalkara, et al.; "In Vivo-Directed Evolution of a New Adeno-Associated Virus for Therapeutic Outer Retinal Gene Delivery from the Vitreous"; Science Translational Medicine; vol. 5, Issue 187, 11 pages (Jun. 12, 2013).
Dalkara, et al.; "Developing Photoreceptor Targeted AAV Variant by Directed Evolution"; ARVO Annual Meeting Abstract Search and Program Planner; vol. 2011, pp. 4381 (May 2011).
Database Geneseq [Online] Oct. 16, 2008 (Oct. 16, 2008), "Modified Adena-associated virus (hu.44) capsid protein, VP1, hu.44R2.", retrieved from EBI accession No. GSP:AEL63853, Database accession No. AEL63853.
Database Geneseq [Online] Oct. 16, 2008 (Oct. 16, 2008), "Modified Adena-associated virus (hu.44) capsid protein, VP1, hu.44R3.", retrieved from EBI accession No. GSP:AEL63854, Database accession No. AEL63854.
Davidson, et al.; "Recombinant adeno-associated virus type 2, 4, and 5 vectors: transduction of variant cell types and regions in the mammalian central nervous system."; Proc Natl Acad Sci USA.; vol. 97, No. 7, pp. 3428-3432 (Mar. 28, 2000).
Day, et al.; "Advances in AAV Vector Development for Gene Therapy in the Retina"; Adv. Exp. Med. Biol.; vol. 801, pp. 687-693 (2014).
Den Dunnen, et al.; "Mutation nomenclature extensions and suggestions to describe complex mutations: a discussion."; Human Mutation; vol. 15, pp. 7-12 (2000).
Diprimio, et al.; "Surface loop dynamics in adeno-associated virus capsid assembly"; Journal of Virology; vol. 82, No. 11, pp. 5178-5189 (Jun. 2008).
Erles, et al.; "Update on the prevalence of serum antibodies (IgG and IgM) to adeno-associated virus (AAV)."; J Med Virol.; vol. 59, No. 3, pp. 406-411 (Nov. 1999).
Excoffon, et al.; "Directed evolution of adeno-associated virus to an infectious respiratory virus"; Proc Natl Acad Sci USA; vol. 106, No. 10, pp. 3865-3870 (Mar. 10, 2009).
Flotte, et al.; "Gene expression from adeno-associated virus vectors in airway epithelial cells"; Am J Respir Cell Mol Biol.; vol. 7, No. 3, pp. 349-356 (Sep. 1992).
Gen Bank accession No. AAZ79678; rat AAV1 VP3 capsid protein sequence downloaded from NCBI; downloaded on Nov. 3, 2008.
GenBank accession No. ABZ10812; AAV13 capsid protein sequence downloaded from NCBI; downloaded on Nov. 3, 2008.
Girod, et al.; "Genetic capsid modifications allow efficient re-targeting of adeno-associated virus type 2"; Nat. Med.; vol. 5, No. 9, pp. 1052-1056 (Sep. 1999).
Gray, et al.; "Directed Evolution of a Novel Adeno-associated Virus (AAV) Vector That Crosses the Seizure-compromised Blood-Brain Barrier (BBB)"; Molecular Therapy; vol. 18, No. 3, pp. 570-578 (2010).
Gregory-Evans, et al.; "Ex vivo Gene Therapy Using Intravitreal Injection of GDNF-secreting Mouse Embryonic Stem Cells in a Rat Model of Retinal Degeneration"; Molecular Vision; vol. 15, pp. 962-973 (May 13, 2009).
Grieger, et al.; "Separate basic region motifs within the adeno-associated virus capsid proteins are essential for infectivity and assembly"; Journal of Virology; vol. 80, No. 11, pp. 5199-5210 (2006).
Grifman, et al.; "Incorporation of tumor-targeting peptides into recombinant adeno-associated virus capsids"; Molecular Therapy; vol. 3, No. 6, pp. 964-975 (Jun. 2001).
Grimm, et al.; "In Vitro and In Vivo Gene Therapy Vector Evolution via Multispecies Interbreeding and Retargeting of Adeno-Associated Viruses"; Journal of Virology; vol. 82, No. 12, pp. 5887-5911 (Jun. 2008).
Halbert, et al.; "Repeat transduction in the mouse lung by using adeno-associated virus vectors with different serotypes." J. Virol.; vol. 74, No. 3, pp. 1524-1532 (Feb. 2000).
Hellstrom, et al.; "Cellular tropism and transduction properties of seven adeno-associated viral vector serotypes in adult retina after intravitreal injection"; Gene Therapy; vol. 16, pp. 521-532 (2009).
Hirsch, et al.; "Directed Evolution of the AAV Capsid for Human Embryonic Stem Cell Transduction"; Molecular Therapy; vol. 17, Supp. 1, S177-S178 (May 2009).
Huttner, et al "Genetic Modifications of the Adeno-Associated Virus Type 2 Capsid Reduce Affinity to Human Serum Antibodies and Overcome Potential Limitations of Neutralizing Antibodies for the Used in Human Gene Therapy"; Blood; vol. 100, No. 11, pp. Abstract No. 5548 (Nov. 16, 2002).
Huttner, et al.; "Genetic modifications of the adeno-associated virus type 2 capsid reduce the affinity and the neutralizing effects of human serum antibodies."; Gene Ther; vol. 10, pp. 2139-2147 (Dec. 2003).
Jang, et al.; "An evolved adeno-associated viral variant enhances gene delivery and gene targeting in neural stem cells"; Mol Ther.; vol. 19, No. 4, pp. 667-675 (Apr. 2011).
Jeune, et al.; "Pre-existing Anti-Adeno-Associated Virus Antibodies as a Challenge in AAV Gene Therapy"; Human Gene Therapy Methods; vol. 24, pp. 59-67 (Apr. 2013).
Karp, et al.; "An in vitro model of differentiated human airway epithelia, Methods for establishing primary cultures"; Methods Mol Biol.; vol. 188, pp. 115-137 (2002).

(56) References Cited

OTHER PUBLICATIONS

Kern, et al.; "Identification of a heparin-binding motif on adeno-associated virus type 2 capsids"; Journal of Virology; vol. 77, No. 20, pp. 11072-11081 (Oct. 2003).
Khabou, et al.; "Insight Into the Mechanisms of Enhanced Retinal Transduction by the Engineered AAV2 Capsid Variant—7m8"; Biotechnology and Bioengineering; vol. 113, No. 12, pp. 2712-2724 (Dec. 2016).
Khani, et al.; "AAV-Mediated Expression Targeting of Rod and Cone Photoreceptors with a Human Rhodopsin Kinase Promoter"; Investigative Ophthalmology & Visual Science; vol. 48, No. 9, pp. 3954-3961 (Sep. 2007).
Klimczak, et al.; "A Novel Adeno-Associated Viral Variant for Efficient and Selective Intravitreal Transduction of Rat Muller Cells"; PLoS ONE; vol. 4, No. 10, pp. 1-10 (Oct. 2009).
Klimczak; "Molecular Evolution of Adeno-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 116 pages (2010).
Koerber, et al.; "DNA Shuffling of Adeno-associated Virus Yields Functionally Diverse Viral Progeny"; Molecular Therapy; vol. 16, No. 10, pp. 1703-1709 (Oct. 2008).
Koerber, et al.; "Engineering of a Novel AAV Vector In a Human Airway Model System for Cystic Fibrosis Gene Therapy"; AIChE Annual Meeting Abstract, 3 pages (Nov. 29, 2008).
Koerber, et al.; "Molecular Evolution of Adeno-associated Virus for Enhanced Glial Gene Delivery", Molecular Therapy; vol. 17, No. 12, pp. 2088-2095 (Dec. 2009).
Kotin et al., (2017) "Geneseq Accession No. BDN88104", computer printout, 2 pages.
Kotterman, et al.; "Engineering adeno-associated viruses for clinical gene therapy"; Nat Rev Genet; vol. 15, No. 7, pp. 445-451 (Jul. 1, 2014).
Kotterman, et al.; "Enhanced selective gene delivery to neural stem cells in vivo by an adeno-associated viral variant"; Development; vol. 142, pp. 1885-1892 (2015).
Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).
Lai, et al.; "Long-term evaluation of AAV-mediated sFlt-1 gene therapy for ocular neovascularization in mice and monkeys"; Mol Ther.; vol. 12, No. 4, pp. 659-668 (Oct. 2005).
Lee, at al.; "Adeno-associated Virus (AAV) Vectors: Rational Design Strategies for Capsid Engineering"; Current Opinion in Biomedical Engineering; pp. 7:58-7:63 (2018).
Li, et al.; "Engineering and Selection of Shuffled AAV Genomes: A New Strategy for Producing Targeted Biological Nanoparticles"; Molecular Therapy; vol. 16, No. 7, pp. 1252-1260 (Jul. 2008).
Li, et al.; "Generation of Novel AAV Variants by Directed Evolution for Improved CFTR Delivery to Human Ciliated Airway Epithelium"; Molecular Therapy; vol. 17, No. 12, pp. 2067-2077 (Dec. 2009).
Limberis, et al.; "Adeno-associated virus serotype 9 vectors transduce murine alveolar and nasal epithelia and can be readministered"; Proc Natl Acad Sci USA; vol. 103, No. 35, pp. 12993-12998 (Aug. 29, 2006).
Loiler, et al.; "Targeting recombinant adeno-associated virus vectors to enhance gene transfer to pancreatic islets and liver"; Gene Ther.; vol. 10, pp. 1551-1558 (2003).
Maguire, et al.; "Directed evolution of adeno-associated virus for glioma cell transduction"; J. Neurooncol.; vol. 96, pp. 337-347 (2010).
Maheshri, et al.; "Directed evolution of adeno-associated virus yields enhanced gene delivery vectors"; Nature Biotechnology; vol. 24, No. 2, pp. 198-204 (Feb. 2006).
McCullum, et al.; "Random Mutagenesis by Error-Prone PCR"; Methods Mol Biol.; vol. 634, pp. 103-109; doi: 10.1007/978-1-60761-652-8_7 (2010).
McGee, et al., "Glial Cell Line Derived Neurotrophic Factor Delays Photoreceptor in a Transgenic Rat Model of Retinitis Pigmentosa"; Molecular Therapy; vol. 4, No. 6, pp. 622-629 (Dec. 2001).
Michelfelder, et al.; "Successful Expansion but Not Complete Restriction of Tropism of Adeno-Associated Virus by In Vivo Biopanning of Random Virus Display Peptide Libraries"; PLoS One; vol. 4, No. 4, pp. 1-13 (Apr. 2009).
Michelfelder, et al.; "Vectors selected from adeno-associated viral display peptide libraries for leukemia cell-targeted cytotoxic gene therapy"; Experimental Hematology; vol. 35, pp. 1766-1776 (2007).
Mitchell, et al.; "AAV's anatomy: Roadmap for optimizing vectors for translational success"; Curr Gene Ther.; vol. 10, No. 5, pp. 319-340 (Oct. 2010).
Miyake, et al.; "Global gene transfer into the CNS across the BBB after neonatal systemic delivery of single-stranded AAV vectors"; Brain Research; vol. 1389, pp. 19-26 (2011).
Moskalenko, et al; "Epitope mapping of human anti-adeno-associated virus type 2 neutralizing antibodies: implications for gene therapy and virus structure."; J. Virol.; vol. 74, No. 4, pp. 1761-1766 (Feb. 2000).
Muller, et al.; "Random peptide libraries displayed on adeno-associated virus to select for targeted gene therapy vectors"; Nat Biotechnol; vol. 21, No. 9, pp. 1040-1046 (Sep. 2003).
Nguyen, et al; "Convection-enhanced delivery of AAV-2 combined with heparin increases TK gene transfer in the rat brain."; Neuroreport; vol. 12, No. 9, pp. 1961-1964 (Jul. 3, 2001).
Nicklin, et al.; "Efficient and selective AAV2-mediated gene transfer directed to human vascular endothelial cells"; Mol. Ther.; vol. 4, No. 2, pp. 174-181 (Aug. 2001).
Opie, et al.; "Identification of Amino Acid Residues in the Capsid Proteins of Adeno-Associated Virus Type 2 that Contribute to Heparan Sulfate Proteoglycan Binding"; Journal of Virology; vol. 77, No. 12, pp. 6995-7006 (Jun. 2003).
Ortolano, et al.; "Present and Future of Adeno Associated Virus Based Gene Therapy Approaches"; Recent Patents on Endocrine, Metabolic & Immune Drug Discovery; vol. 6, pp. 47-66 (2012).
Paddison, et al.; "Stable suppression of gene expression by RNAi in mammalian cells"; Proc. Nat'l Acad. Sci. USA; vol. 99, No. 3, pp. 1443-1448 (Feb. 5, 2002).
Padron, et al.; "Structure of adeno-associated virus type 4"; Journal of Virology; vol. 79, No. 8, pp. 5047-5058 (Apr. 2005).
Park, et al.; "Intravitreal delivery of AAV8 retinoschisin results in cell type-specific gene expression and retinal rescue in the Rs1-KO mouse"; Gene Therapy; vol. 16, pp. 916-926 (2009).
Pechan, et al; "Novel anti-VEGF chimeric molecules delivered by AAV vectors for inhibition of retinal neovascularization."; Gene. Ther.; vol. 16, No. 1, pp. 10-16 (Jan. 2009).
Perabo, et al.; "Combinatorial engineering of a gene therapy vector: directed evolution of adeno-associated virus"; The Journal of Gene Medicine; vol. 8, No. 2, pp. 155-162 (Feb. 2006).
Perabo, et al.; "Heparan Sulfate Proteoglycan Binding Properties of Adeno-Associated Virus Retargeting Mutants and Consequences for Their In Vivo Tropism"; Journal of Virology; vol. 80, No. 14, pp. 7265-7269 (Jul. 2006).
Perabo, et al.; "In Vitro Selection of Viral Vectors with Modified Tropism: The Adeno-associated Virus Display"; Molecular Therapy; vol. 8, No. 1, pp. 151-157 (Jul. 2003).
Petrs-Silva, et al.; "High-efficiency transduction of the mouse retina by tyrosine-mutant AAV serotype vectors"; Molecular Therapy; vol. 17, No. 3, pp. 463-471 (Mar. 2009).
Popa-Wagner, et al.; "Impact of VP1-Specific Protein Sequence Motifs on Adeno-Associated Virus Type 2 Intracellular Trafficking and Nuclear Entry"; Journal of Virology; vol. 86, No. 17, pp. 9163-9174 (Sep. 2012).
Rabinowitz, et al.; "Building a Better Vector: The Manipulation of AAV Virions"; Virology; vol. 278, pp. 301-308 (2000).
Rabinowitz, et al.; "Insertional mutagenesis of AAV2 capsid and the production of recombinant virus."; Virology; vol. 265, No. 2, pp. 274-285 (Dec. 20, 1999).
Rayaprolu, et al.; "Comparative Analysis of Adeno-Associated Virus Capsid Stability and Dynamics"; Journal of Virology; vol. 87, No. 24, pp. 13150-13160 (Dec. 2013).

(56) References Cited

OTHER PUBLICATIONS

Ried, et al.; "Adeno-associated virus capsids displaying immunoglobulin-binding domains permit antibody-mediated vector retargeting to specific cell surface receptors"; J. Virol.; vol. 76, No. 9, pp. 4559-4566 (May 2002).
Ryals, et al.; "Quantifying transduction efficiencies of unmodified and tyrosine capsid mutant AAV vectors in vitro using two ocular cell lines"; Mol Vision; vol. 17, pp. 1090-1102 (Apr. 2011).
Santiago-Ortiz, et al.; "AAV Ancestral Reconstruction Library Enables Selection of Broadly Infectious Viral Variants"; Gene. Ther.; vol. 22, No. 12, pp. 934-946 (Dec. 2015).
Schaffer et al., 2014, Geneseq Accession No. BBR00471, computer printout, pp. 1-2.
Schaffer, et al.; "Directed evolution of AAV vector mutants for enhanced gene delivery"; Abstracts of Papers American Chemical Society; vol. 227, Part 1, p. U214 (Mar. 2004).
Shao, et al.; "Gene Transfer to the Gastrointestinal Tract After Peroral Administration of Recombinant Adeno-associated Virus Type 2 Vectors"; Journal of Pediatric Gastroenterology and Nutrition; vol. 43, pp. 168-179 (Aug. 2006).
Shen, et al.; "Characterization of the relationship of AAV capsid domain swapping to liver transduction efficiency"; Mol Ther.; vol. 15, No. 11, pp. 1955-1962 (Aug. 28, 2007).
Shen, et al.; "Multiple Roles for Sialylated Glycans in Determining the Cardiopulmonary Tropism of Adeno-Associated Virus 4"; Journal of Virology; vol. 87, No. 24, pp. 13206-13213 (Dec. 2013).
Shi, et al.; "Capsid modifications overcome low heterogeneous expression of heparan sulfate proteoglycan that limits AAV2-mediated gene transfer and therapeutic efficacy in human ovarian carcinoma"; Gynecol. Oncol.; vol. 103, pp. 1054-1062 (2006).
Shi, et al.; "Insertional mutagenesis at positions 520 and 584 of adeno-associated virus type 2 (AAV2) capsid gene and generation of AAV2 vectors with eliminated heparin-binding ability and introduced novel tropism"; Hum. Gene Ther.; vol. 17, pp. 353-361 (Mar. 2006).
Shi, et al.; "RGD inclusion in VP3 provides adeno-associated virus type 2 (AAV2)-based vectors with a heparan sulfate-independent cell entry mechanism"; Mol. Ther.; vol. 7, No. 4, pp. 515-525 (Apr. 2003).
Shi, W. et al.; "Insertional Mutagenesis of the Adeno-Associated Virus Type 2 (AAV2) Capsid Gene and Generation of AAV2 Vectors Targeted to Alternative Cell-Surface Receptors"; Human Gene Therapy; vol. 12, pp. 1697-1711 (Sep. 20, 2001).
Sonntag, et al.; "Adeno-associated virus type 2 capsids with externalized VP1/VP2 trafficking domains are generated prior to passage through the cytoplasm and are maintained until uncoating occurs in the nucleus"; Journal of Virology; vol. 80, No. 22, pp. 11040-11054 (Nov. 2006).
Steinbach, et al.; "Assembly of adeno-associated virus type 2 capsids in vitro" J of Gen Virology; vol. 78, pp. 1453-1462 (1997).
Sullivan, et al.; "Rationally designed AAV2 and AAVrh8R capsids provide improved transduction in the retina and brain"; Gene Therapy; vol. 25, pp. 205-219 (2018).
Sun, et al.; "Immune responses to adeno-associated virus and its recombinant vectors"; Gene Therapy; vol. 10, pp. 964-976 (2003).
Surace, et al.; "Delivery of Adeno-Associated Virus Vectors to the Fetal Retina: Impact of Viral Capsid Proteins on Retinal Neuronal Progenitor Transduction"; Journal of Virology; vol. 77, No. 14, pp. 7957-7962 (Jul. 2003).
Takada, et al.; "Synaptic Pathology in Retinoschisis Knockout (Rs1$^{-/y}$) Mouse Retina and Modification by rAAV-Rs1 Gene Delivery"; Investigative Ophthalmology & Visual Science; vol. 49, No. 8, pp. 3677-3678 (Aug. 2008).
Tal; "Adeno-Associated Virus-Based Vectors in Gene Therapy"; Journal of Biomedical Science; vol. 7, No. 4, pp. 279-291 (Jul. 2000).
Tervo, et al.; "A Designer AAV Variant Permits Efficient Retrograde Access to Projection Neurons"; Neuron; vol. 92, pp. 372-382 (2016).
Tomar, et al.; "Use of Adeno-Associated Viral Vector for Delivery of Small Interfering RNA"; Oncogene; vol. 22, No. 36, pp. 5712-5715 (Aug. 28, 2003).
UniProtKB database: B4Y881_9VIRU; "Capsid protein VP1, adeno-associated virus"; 6 pages (Sep. 23, 2008).
Van Vliet, et al.; "Proteolytic mapping of the adeno-associated virus capsid"; Mol Ther.; vol. 14, No. 6, pp. 809-821 (Dec. 2006).
Venkatakrishnan, et al.; "Structure and Dynamics of Adeno-Associated Virus Serotype 1 VP1-Unique N-Terminal Domain and Its Role in Capsid Trafficking"; Journal of Virology; vol. 87, No. 9, pp. 4974-4984 (May 2013).
Watanabe, et al.; "Tropisms of AAV for Subretinal Delivery to the Neonatal Mouse Retina and Its Application for In Vivo Rescue of Developmental Photoreceptor Disorders"; PLoS ONE; vol. 8, No. 1, 12 pages (Jan. 15, 2013).
Waterkamp, et al.; "Isolation of targeted AAV2 vectors from novel virus display libraries"; J. Gene. Med.; vol. 8, pp. 1307-1319 (Sep. 6, 2006).
White, et al.; "Genetic Modification of Adeno-Associated Viral Vector Type 2 Capsid Enhances Gene Transfer Efficiency in Polarized Human Airway Epithelial Cells"; Human Gene Therapy; vol. 19, pp. 1407-1414 (Dec. 2008).
White, et al.; "Targeted gene delivery to vascular tissue in vivo by tropism-modified adeno-associated virus vectors"; Circulation; vol. 109, pp. 513-519 (Feb. 3, 2004).
Wickham, et al.; "Increased in vitro and in vivo gene transfer by adenovirus vectors containing chimeric fiber proteins"; Journal of Virology; vol. 71, No. 11, pp. 8221-8229 (Nov. 1997).
Willett, et al.; "Immunology of AAV-mediated gene transfer in the eye"; Frontiers in Immunology; vol. 4, No. 261, 8 pages (Aug. 2013).
Wobus, et al.; "Monoclonal antibodies against the adeno-associated virus type 2 (AAV-2) capsid: epitope mapping and identification of capsid domains involved in AAV-2-cell interaction and neutralization of AAV-2 infection."; J. Virol.; vol. 74, No. 19, pp. 9281-9293 (Oct. 2000).
Work, et al.; "Vascular bed-targeted in vivo gene delivery using tropism-modified adeno-associated viruses"; Mol. Ther.; vol. 13, No. 4, pp. 683-693 (Apr. 2006).
Wu, et al.; "Mutational analysis of the adeno-associated virus type 2 (AAV2) capsid gene and construction of AAV2 vectors with altered tropism"; Journal of Virology; vol. 74, No. 18, pp. 8635-8647 (Sep. 2000).
Wu, et al.; "$\alpha 2,3$ and $\alpha 2,6$ N-linked Sialic Acids Facilitate Efficient Binding and Transduction by Adeno-Associated Virus Types 1 and 6"; Journal of Virology; vol. 80, No. 18, pp. 9093-9103 (Sep. 2006).
Xiao, et al.; "Adenovirus-facilitated nuclear translocation of adeno-associated virus type 2"; Journal of Virology; vol. 76, No. 22, pp. 11505-11517 (Nov. 2002).
Xie, et al.; "The atomic structure of adeno-associated virus (AAV-2), a vector for human gene therapy"; PNAS; vol. 99, No. 16, pp. 10405-10410 (Aug. 6, 2002).
Yang, et al.; "A myocardium tropic adeno-associated virus (AAV) evolved by DNA shuffling and in vivo selection"; PNAS; vol. 106, No. 10, pp. 3946-3951 (Mar. 10, 2009).
Yang, et al.; "Directed Evolution of Adeno-Associated Virus (AAV) as Vector for Muscle Gene Therapy"; Methods in Molecular Biology; vol. 709, pp. 127-139 (2011).
Yu; "Current Approaches and Future Directions of Gene Therapy in Alzheimer's Disease"; Neurochemical Journal; vol. 5, No. 3, pp. 159-168 (2011).
Zabner, et al.; "Adeno-associated virus type 5 (AAV5) but not AAV2 binds to the apical surfaces of airway epithelia and facilitates gene transfer"; J Virol.; No. 74, No. 8, pp. 3852-3858 (Apr. 2000).
Zhao, et al.; "Molecular evolution by staggered extension process (StEP) in vitro recombination"; Nat Biotechnol; vol. 16, No. 3, pp. 258-261 (Mar. 1998).
Zincarelli, et al.; "Analysis of AAV Serotypes 1-9 Mediated Gene Expression and Tropism in Mice After Systemic Injection"; Molecular Therapy; vol. 16, No. 6, pp. 1073-1080 (Jun. 2008).
Zolotukhin, et al.; "Recombinant adeno-associated virus purification using novel methods improves infectious titer and yield"; Gene Therapy; vol. 6, pp. 973-985 (1999).

(56) References Cited

OTHER PUBLICATIONS

Weinstein, et al., "New Methods in Engineering Adeno-Associated Virus (AAV) for Improved Gene Delivery." Dissertaion from University of California, Berkeley, Dissertation No. 3720891, ProQuest ID: 1726005971, https://dialog.proquest.com/professional/docview/1726005971?accountid=131444. (Year: 2013).
Bantel-Schaal et al., (1999) "Human adeno-associated virus type 5 is only distantly related to other known primate helper-dependent parvoviruses.", J. Virol., 73:939-947.
Third-Party Submission dated Mar. 15, 2022, U.S. Appl. No. 16/315,032, 95 pages.
Antonarakis, "Recommendations for a nomenclature system for human gene mutations", Human Mutation, 1998, 11(1):1-3.
Arbetman et al., "Caprine adeno-associated virus capsid protein VP1", Score result 33 for WO2004112727A2, Accession No. ADV70291, Dec. 29, 2004, 3 pages.
Bantel-Schaal et al., "Score result: Human adeno-associated virus type 5 is only distantly related to other known primate helper-dependent parvoviruses, Gene Accession No. Y18065", 1999, 4 pages.
Bantel-Schaal et al., "Score result: Human adeno-associated virus type 5 is only distantly related to other known primate helper-dependent parvoviruses, Gene Accession No. Q9YIJ1, integrated into UniProtKB/TrEMBL on May 1, 1999", 3 pages.
Dimattia et al., "Structural insight into the unique properties of adeno-associated virus serotype 9", Journal of Virology, Jun. 2012, 86(12):6947-6958.
Douar, et al., "Deleterious effect of peptide insertions in a permissive site of the AAV2 capsiD", Virology, May 10, 2003, 309(2):203-208.
Gurda et al., "Mapping a neutralizing epitope onto the capsid of adeno-associated virus serotype 8", Journal of Virology, Aug. 2012, 86(15): 7739-7751.
Klimczak et al., "Molecular engineering of adeno-associated virus yields a novel variant with efficient intravitreal transduction of Muller cells", Molecular Therapy, May 2009, 17:Supplement 1:S178.
Koerber et al., "Molecular evolution of adeno-associated virus for enhanced glial gene delivery", Molecular Therapy, Dec. 2009, 17(12):2088-2095.
Koerber, "Engineering Adeno-associated Viral Vectors with Novel Structure-Function Relationships for Improved Gene Delivery", Koerber Dissertation, University of California, Berkeley, 2008, 323 pages.
Lane et al., "Production, purification, crystallization and preliminary X-ray analysis of adeno-associated virus serotype 8", Acta Crystallographica Section F Structural Biology and Crystallization Communications, Jun. 1, 2005, 61(6):558-561.
Lerch et al., "The structure of adeno-associated virus serotype 3B (AAV-3B): Insights into receptor binding and immune evasion", Virology, Jul. 20, 2010, 403(1):26-36.
Lochrie et al., "Mutations on the external surfaces of adeno-associated virus type 2 capsids that affect transduction and neutralization", Journal of Virology, Jan. 2006, 80(2):821-834.
Mace et al., "Targeting channelrhodopsin-2 to ON-bipolar cells with vitreally administered AAV restores on and off visual responses in blind mice", Molecular Therapy, Jan. 2015, 23(1):7-16.
McCraw, "Structure of adeno-associated virus-2 in complex with neutralizing monoclonal antibody A20", Virology, Sep. 2012, 431(1-2):40-49.
Miller et al., "Production, purification and preliminary X-ray crystallographic studies of adeno-associated virus serotype 1", Acta Crystallographica Section F Structural Biology and Crystallization Communications, Dec. 1, 2006, 62(12):1271-1274.
Nam et al., "Structure of adeno-associated virus serotype 8, a gene therapy vector", Journal of Virology, Nov. 2007, 81(22):12260-12271.
Petrs-Silva et al., "Novel properties of tyrosine-mutant AAV2 vectors in the mouse retina", Molecular Therapy, Feb. 2011, 19(2):293-301.
Samulski et al., "Rescue of adeno-associated virus from recombinant plasmids: gene correction within the terminal repeats of AAV", Cell, May 1983, 33(1):135-143.
Tse et al., "Structure-guided evolution of antigenically distinct adeno-associated virus variants for immune evasion", Proceedings of the National Academy of Sciences of the United States of America, Jun. 13, 2017, 114(24):E4812-E4821.
Walters et al., "Structure of Adeno-Associated Virus Serotype 5", Journal of Virology, Apr. 2004, 78(7):3361-3371.
Wu et al., "Single amino acid changes can influence titer, heparin binding, and tissue tropism in different adeno-associated virus serotypes", Journal of Virology, Nov. 2006, 80(22):11393-11397.
Xie et al., "Structure-function analysis of receptor-binding in adeno-associated virus serotype 6 (AAV-6)", Virology, Nov. 10, 2011, 420(1):10-19.
Xue et al., "CRALBP supports the mammalian retinal visual cycle and cone vision", The Journal of Clinical Investigation, Feb. 2015, 125(2):727-738.

\* cited by examiner

FIG. 2

| Source library | peptide insertion | Peptide No. | SEQ ID NO: |
|---|---|---|---|
| AAV2-7mer | LALIQDSMRA | 21 | 35 |
| AAV2-7mer | LTHQDTTKNA |  | 4 |
| AAV2-7mer | LANQEHVKNA | 22 | 2 |
| AAV2-7mer | QAHQDTTKNA |  | 5 |
| AAV4-7mer | TGVMRSTNSGLN | 1 | 6 |
| AAV4-7mer | TGEVDLAGGGLS | 2 | 7 |
| AAV4-7mer | TSPYSGSSDGLS | 3 | 8 |
| AAV4-7mer | TGGHDSSLDGLS | 4 | 9 |
| AAV4-7mer | TGDGGTTMNGLS | 5 | 98 |
| AAV4-7mer | TGGHGSAPDGLS | 6 | 99 |
| AAV5-7mer | TGMHVTMMAGLN | 7 | 100 |
| AAV5-7mer | TGASYLDNSGLS | 8 | 101 |
| AAV5-7mer | TVVSTQAGIGLS | 9 | 20 |
| AAV5-7mer | TGVMHSQASGLS | 10 | 21 |
| AAV5-7mer | TGDGSPAAPGLS | 11 | 22 |
| AAV5-7mer | TGSDMAHGTGLS | 12 | 23 |
| Anc-7mer | TGLDATRDHGLSPVTGT | 13 | 24 |
| Anc-7mer | TGSDGTRDHGLSPVTWT | 14 | 25 |
| Anc-7mer | NGAVADYTRGLSPATGT | 15 | 26 |
| Anc-7mer | TGGDPTRGTGLSPVTGA | 16 | 27 |
| LoopSwap588 | LQKNARPASTESVNFQ | 17 | 28 |
| LoopSwap588 | LQRGVRIPSVLEVNGQ | 18 | 29 |
| LoopSwap588 | LQRGNRPVTTADVNTQ | 19 | 30 |
| LoopSwap588 | LQKADRQPGVVVVNCQ | 20 | 31 |

FIG. 3A
*Streptococcus pyogenes* Cas9

```
   1 mdkkysigld igtnsvgwav itdeykvpsk kfkvlgntdr hsikknliga llfdsgetae
  61 atrlkrtarr rytrrknric ylqeifsnem akvddsffhr leesflveed kkherhpifg
 121 nivdevayhe kyptiyhlrk klvdstdkad irliyialah mikfrghfli egdlnpdnsd
 181 vdklfiqlvq tynqlfeenp inasgvdaka ilsarlsksr rlenliaqlp gekknglfgn
 241 lialsigltp nfksnfdlae dakiqlskdt yddldlnlla qigdqyadlf laaknlsdai
 301 llsdilrvnt eitkapisas mikrydehhq ditlikalvr qqipekykei ffdqskngya
 361 gyidggasqe efykfikpil ekmdgteeil vklnredllr kqrtfdngsi phqihlgelh
 421 ailrrqedfy pflkdnreki ekiltfripy yvgplargns rfawmtrkse etitpwnfee
 481 vvdkgasaqs fiermtnfdk nlpnekvlpk hsllyeyftv yneltkvkyv tegmrkpafl
 541 sgeqkkaivd llfktnrkvt vkqlkedyfk kiecfdsvei sgvedrfnas lgtyhdliki
 601 ikdkdfldne enediledlv itltifedre mieeriktya hlfddkvmkq lkrrrytgwg
 661 rlsrklingi rdkqsgktil dflksdgfan rnfmqlihdd sltfkediqk aqvsgqgdsl
 721 hehianlags paikkgilqt vkvvdelvkv mgrhkpeniv iemarenqtt qkgqknsrer
 781 mkrieegike lgsqilkehp ventqlqnek lylylqngr dmyvdqeldi nrlsdydvdh
 841 ivpqsfikdd sidnkvltrs dknrgksdnv pseevvkkmk nywrqllnak litqrkfdnl
 901 tkaergglse ldkagfikrq lvetrqitkh vaqildsrmn tkydendkli revkvitlks
 961 klvsdfrkdf qfykvreinn yhhahdayln avvgtalikk ypklesefvy gdykvydvrk
1021 miakseqeig katakyffys nimnfffktei tlangeirkr plietngetg eivwdkgrdf
1081 atvrkvlsmp qvnivkktev qtggfskesi lpkrnsdkli arkkdwdpkk yggfdsptva
1141 ysvlvvakve kgkskkliksv keligitime rssfeknpid fleakgykev kkdliiiklpk
1201 yslfelengr krmlasagel qkgnelaips kyvnflylas hyeklkgspe dneqkqlfve
1261 qhkhyldeii eqisefskrv iladanldkv lsaynkhrdk plreqaenii hlftltnlga
1321 paafkyfdtt idrkrytstk evldatlihq sitglyetri disqlggd   (SEQ ID NO: 32)
```

FIG. 3B
*Staphylococcus aureus* Cas9

```
   1 mkrnyilgld igitsvgygi idyetrdvid agvrlfkean vennegrrsk rgarrlkrrr
  61 rhrigrvkkl lfdynlltdh selsginpye arvkglsqkl seeefsaall hlakrrgvhn
 121 vneveedtgn elstkeqisr nskaleekyv aelqlerlkk dgevrgsinr fktsdyvkea
 181 kqllkvqkay hqldqsfidt yidlietrrt yyegpgegsp fgwkdikewy emlmghctyf
 241 peelrsvkya ynadlynain dinnlvitrd enekleyyek fqiienvfkq kkkptlkqia
 301 keilvneedi kgyrvtstgk peftnlkvyh dikditarke iienaelldq iakilltiyqs
 361 sediqeeltn inseltqeei eqisnlkgyt gthnlsikai nlildelwht ndnqiaifnr
 421 lkivpkkvdl sqqkeipttl vddfilspvv krsfiqsikv inailkkygl pndiiielar
 481 eknskdaqkm inemqkrnrq tnerieeiir ttgkenakyl iekiklhdmq egkclyslea
 541 iplediinnp fnyevdhiip rsvsfdnsfn nkvlvkqeen skkgnrtpfq ylsssdskis
 601 yetfkkhiln lakgkgrisk tkkeylleer dinrfsvqkd finrnlvdtr yatrglmnll
 661 rsyfrvnnld vkvksinggf tsflrrkwkf kkernkgykh haedaliian adfifkewkk
 721 ldkakkvmen qmfeekqaes mpeieteqey keifitphqi khikdfkdyk yshrvdkkpn
 781 relindtlys trkddkgntl ivnninglyd kdndkikkli nkspeklimy hhdpqtyqkl
 841 klimeqygde knplykyyee tgnyltkysk kdngpvikki kyygnkinah lditddypns
 901 rnkvvkislk pyrfdvyldn gvykfvtvkn ldvikkenyy evnskcyeea kklkkisnqa
 961 efiasfynnd likingelyr vignvndlln rievnmidit yreylenmnd krppriikti
1021 asktqsikky stdilgnlye vkskkhpqil kkg (SEQ ID NO: 33)
```

FIG. 3C
*Francisella tularensis* Cpf1

```
   1 msiyqefvnk yslsktlrfe lipqgktlen ikarglildd ekrakdykka kqiidkyhqf
  61 fieeilssvc isedllqnys dvyfklkksd ddnlqkdfks akdtikkqis eyikdsekfk
 121 nlfnqnlida kkgqesdlil wlkqskdngi elfkansdit didealeiik sfkgwttyfk
 181 gfhenrknvy ssndiptsii yrivddnlpk flenkakyes lkdkapeain yeqikkdlae
 241 eltfdidykt sevnqrvfsl devfeianfn nylnqsgitk fntiiggkfv ngentkrkgi
 301 neyinlysqq indktlkkyk msvlfkqils dtesksfvid kleddsdvvt tmqsfyeqia
 361 afktveeksi ketlsllfdd lkaqkldlsk iyfkndkslt dlsqqvfddy svigtavley
 421 itqqiapknl dnpskkeqel iakktekaky lsletiklal eefnkhrdid kqcrfeeila
 481 nfaaipmifd eiaqnkdnla qisikyqnqg kkdllqasae ddvkaikdll dqtnnllhkl
 541 kifhisqsed kanildkdeh fylvfeecyf elanivplyn kirnyitqkp ysdekfklnf
 601 enstlangwd knkepdntai lfikddkyyl gvmnkknnki fddkaikenk gegykkivyk
 661 llpgankmlp kvffsaksik fynpsedilr irnhsthtkn gspqkgyekf efniedcrkf
 721 idfykqsisk hpewkdfgfr fsdtqrynsi defyrevenq gykltfenis esyidsvvnq
 781 gklylfqiyn kdfsayskgr pnlhtlywka lfdernlqdv vyklngeael fyrkqsipkk
 841 ithpakeaia nknkdnpkke svfeydlikd krftedkfff hcpitinfks sgankfndei
 901 nlllkekand vhilsidrge rhlayytlvd gkgniikqdt fniigndrmk tnyhdklaai
 961 ekdrdsarkd wkkinnikem kegylsqvvh eiaklvieyn aivvfedlnf gfkrgrfkve
1021 kqvyqklekm lieklnylvf kdnefdktgg vlrayqltap fetfkkmgkq tgiiyyvpag
1081 ftskicpvtg fvnqlypkye svsksqeffs kfdkicynld kgyfefsfdy knfgdkaakg
1141 kwtiasfgsr linfrnsdkn hnwdtrevyp tkelekllkd ysieyghgec ikaaicgesd
1201 kkffakltsv lntilqmrns ktgteldyli spvadvngnf fdsrqapknm pqdadangay
1261 higlkglmll griknnqegk klnlviknee yfefvqnrnn (SEQ ID NO: 34)
```

Figure 4

| | | |
|---|---|---|
| AAV2 VP1 | 1 | MAADGYLPDWLEDTLSEGIRQWWKLKPGPPPPKPAERHKDDSRGLVLPGYKYLGPFNGLD |
| AAV2 VP1 | 61 | KGEPVNEADAAALEHDKAYDRQLDSGDNPYLKYNHADAEFQERLKEDTSFGGNLGRAVFQ |
| AAV2 VP1 | 121 | AKKRVLEPLGLVEEPVKTAPGKKRPVEHSPVEPDSSSGTGKAGQQPARKRLNFGQTGDAD |
| AAV2 VP1 | 181 | SVPDPQPLGQPPAAPSGLGTNTMATGSGAPMADNNEGADGVGNSSGNWHCDSTWMGDRVI |
| AAV2 VP1 | 241 | TTSTRTWALPTYNNHLYKQISSQSGASNDNHYFGYSTPWGYFDFNRFHCHFSPRDWQRLI |
| AAV2 VP1 | 301 | NNNWGFRPKRLNFKLFNIQVKEVTQNDGTTTIANNLTSTVQVFTDSEYQLPYVLGSAHQG |
| AAV2 VP1 | 361 | CLPPFPADVFMVPQYGYLTLNNGSQAVGRSSFYCLEYFPSQMLRTGNNFTFSYTFEDVPF |
| AAV2 VP1 | 421 | HSSYAHSQSLDRLMNPLIDQYLYYLSRTNTPSGTTTQSRLQFSQAGASDIRDQSRNWLPG |
| AAV2 VP1 | 481 | PCYRQQRVSKTSADNNNSEYSWTGATKYHLNGRDSLVNPGPAMASHKDDEEKFFPQSGVL |
| AAV2 VP1 | 541 | IFGKQGSEKTNVDIEKVMITDEEEIRTTNPVATEQYGSVSTNLQRGNRQAATADVNTQGV |
| AAV2 VP1 | 601 | LPGMVWQDRDVYLQGPIWAKIPHTDGHFHPSPLMGGFGLKHPPPQILIKNTPVPANPSTT |
| AAV2 VP1 | 661 | FSAAKFASFITQYSTGQVSVEIEWELQKENSKRWNPEIQYTSNYNKSVNVDFTVDTNGVY |
| AAV2 VP1 | 721 | SEPRPIGTRYLTR (SEQ ID NO:1) |

FIG. 5

```
AAV-2      570 PVATEQYGSVSTNLQRGNRQAATADVNTQGVLPGMVWQDRDV 611 (SEQ ID NO: 36)
AAV-1      571 PVATERFGTVAVNFQSSSTDPATGDVHAMGALPGMVWQDRDV 612 (SEQ ID NO: 37)
AAV-5      560 RVAYNVGGQMATNNQSSTTAPATGTYNLQEIVPGSVWMERDV 601 (SEQ ID NO: 38)
AAV-6      571 PVATERFGTVAVNLQSSSTDPATGDVHVMGALPGMVWQDRDV 612 (SEQ ID NO: 39)
AAV-7      572 PVATEEYGIVSSNLQAANTAAQTQVVNNQGALPGMVWQNRDV 613 (SEQ ID NO: 40)
AAV-8      573 PVATEEYGIVADNLQQQNTAPQIGTVNSQGALPGMVWQNRDV 614 (SEQ ID NO: 41)
AAV-9      571 PVATESYGQVATNHQSAQAQAQTGWVQNQGILPGMVWQNRDV 612 (SEQ ID NO: 42)
AAV-10     573 PVATEQYGVVADNLQQANTGPIVGNVNSQGALPGMVWQNRDV 614 (SEQ ID NO: 43)
AAV-4      569 ATDTDMWGNLPGGDQSNSNLPTVDRLTALGAVPGMVWQNRDI 610 (SEQ ID NO: 44)
Ancestral  573 PVATEXYGVVAXNLQSSNTAPXTGXVNSQGALPGMVWQNRDV 613 (SEQ ID NO: 45)
```

Figure 6A

```
AAV1      ---TFSYTFEEVPFHSSYAHSQSLDRLMNPLIDQYLYYLNRTQ-NQSGSAQNKDLLFSRGS  467  (SEQ ID NO: 46)
AAV6      ---TFSYTFEDVPFHSSYAHSQSLDRLMNPLIDQYLYYLNRTQ-NQSGSAQNKDLLFSRGS  467  (SEQ ID NO: 47)
AAV3      ---FSYTFEDVPFHSSYAHSQSLDRLMNPLIDQYLYYLNRTQGTTSGTTNQSRLLFSQAG  467  (SEQ ID NO: 48)
AAV2      ----FSYTFEDVPFHSSYAHSQSLDRLMNPLIDQYLYYLSRTN-TPSGTTTQSRLQFSQAG  466  (SEQ ID NO: 49)
AAV8      NFQFTYTFEDVPFHSSYAHSQSLDRLMNPLIDQYLYYLSRTQT--GGTANTQTLGFSQGG  469  (SEQ ID NO: 50)
AAV8.1    NFQFTYTFEDVPFHSSYAHSQSLDRLMNPLIDQYLYYLSRTQT--GGTANTQTLGFSQGG  469  (SEQ ID NO: 51)
AAV8 rh8  FQFSYTFEDVPFHSSYAHSQSLDRLMNPLIDQYLYYLVRTQTTGTGGTQTLAFSQAGPS  469  (SEQ ID NO: 52)
AAV10     NFEFSYTFEDVPFHSSYAHSQSLDRLMNPLIDQYLYYLSRTQST-GGTQGTQQLLFSQAG  469  (SEQ ID NO: 53)
AAV7      -FEFSYSFEDVPFHSSYAHSQSLDRLMNPLIDQYLYYLARTQSNPGGTAGNRELQFYQGG  469  (SEQ ID NO: 54)
AAV9      -FQFSYEFENVPFHSSYAHSQSLDRLMNPLIDQYLYYLSKTI--NGSGQNQQTLKFSVAG  467  (SEQ ID NO: 55)
AAV9.1    -FQFSYEFENVPFHSSYAHSQSLDRLMNPLIDQYLYYLSKTI--NGSGQNQQTLKFSVAG  467  (SEQ ID NO: 56)
AAV5      NFEFTYNFEEVPFHSSFAPSQNLFKLANPLVDQYLYRFVSTN------NTGGVQFNKNL  453  (SEQ ID NO: 57)
                * ** *:****:** .     . :  :****:**   .         .

AAV1      PAGMSVQPKNWLPGPCYRQQRVSKTKTDNNNSNFTWTGASKYNLNGRESIINPGTAMASH  527  (SEQ ID NO: 58)
AAV6      PAGMSVQPKNWLPGPCYRQQRVSKTKTDNNNSNFTWTGASKYNLNGRESIINPGTAMASH  527  (SEQ ID NO: 59)
AAV3      PQSMSLQARNWLPGPCYRQQRLSKTANDNNNSNFPWTAASKYHLNGRDSLVNPGPAMASH  527  (SEQ ID NO: 60)
AAV2      ASDIRDQSRNWLPGPCYRQQRVSKTSADNNNSEYSWTGATKYHLNGRDSLVNPGPAMASH  526  (SEQ ID NO: 61)
AAV8      PNTMANQAKNWLPGPCYRQQRVSTTTGQNNNSNFAWTAGTKYHLNGRNSLANPGIAMATH  529  (SEQ ID NO: 62)
AAV8.1    PNTMANQAKNWLPGPCYRQQRVSTTTGQNNNSNFAWTAGTKYHLNGRNSLANPGIAMATH  529  (SEQ ID NO: 63)
AAV8 rh8  S--MANQARNWVPGPCYRQQRVSTTTNQNNNSNFAWTGAAKFKLNGRDSLMNPGVAMASH  527  (SEQ ID NO: 64)
AAV10     PANMSAQAKNWLPGPCYRQQRVSTTLSQNNNSNFAWTGATKYHLNGRDSLVNPGVAMATH  529  (SEQ ID NO: 65)
AAV7      PSTMAEQAKNWLPGPCFRQQRVSKTLDQNNNSNFAWTGATKYHLNGRNSLMNPGPAMASH  527  (SEQ ID NO: 66)
AAV9      PSNMAVQGRNYIPGPSYRQQRVSTTVTQNNNSEFAWPGASSWALNGRNSLMNPGPAMASH  529  (SEQ ID NO: 67)
AAV9.1    PSNMAVQGRNYIPGPSYRQQRVSTTVTQNNNSEFAWPGASSWALNGRNSLMNPGPAMASH  527  (SEQ ID NO: 68)
AAV5      AGRYANTYKNWFPGPMGRTQGWNLGSGVNRASVSAFATTNRMELEGASYQVPPQPNGMTN  513  (SEQ ID NO: 69)
           .     ::* ** .* :      .      . :   .              .    ::
```

Figure 6B

```
AAV1     KDDEDKFFPMSGVMIFGK--ESAGASNTALD-NVMITDEEEIKATNPVATERFGTVAVNF 584 (SEQ ID NO: 70)
AAV6     KDDKDKFFPMSGVMIFGK--ESAGASNTALD-NVMITDEEEIKATNPVATERFGTVAVNL 584 (SEQ ID NO: 71)
AAV3     KDEEKFFPMHGNLIFGK--EGTTASNAELD-NVMITDEEEIRTTNPVATEQYGTVANNL 584 (SEQ ID NO: 72)
AAV2     KDEEKFFPQSGVLIFGK--QGSEKTNVDIE-KVMITDEEEIRTTNPVATEQYGSVSTNL 583 (SEQ ID NO: 73)
AAV8     KDEERFFPSNGILIFGK--QNAARDNADYS-DVMLTSEEEIKTTNPVATEEYGIVADNL 586 (SEQ ID NO: 74)
AAV8.1   KDDEERFFPSNGILIFGK--QNAARDNADYS-DVMLTSEEEIKTTNPVATEEYGIVADNL 586 (SEQ ID NO: 75)
AAV8 rh8 KDDDDRFFPSSGVLIFGK--QGAGNDGVDYS-QVLITDEEEIKATNPVATEEYGAVAINN 584 (SEQ ID NO: 76)
AAV10    KDDEERFFPSSGVLMFGK--QGAGRDNVDYS-SVMLTSEEEIKTTNPVATEQYGVVADNL 586 (SEQ ID NO: 77)
AAV7     KDDEDRFFPSSGVLIFGK--TGAT-NKTTLE-NVLMTNEEEIRPTNPVATEEYGIVSSNL 585 (SEQ ID NO: 78)
AAV9     KEGEDRFFPLSGSLIFGK--QGTGRDNVDAD-KVMITNEEEIKTTNPVATESYGQVATNH 584 (SEQ ID NO: 79)
AAV9.1   KEGEDRFFPLSGSLIFGK--QGTGRDNVDAD-KVMITNEEEIKTTNPVATESYGQVATNH 584 (SEQ ID NO: 80)
AAV5     NLQGSNTYALENTMIFNSQPANPGTTATYLEGNMLITSESETQPVNRVAYNVGGQMATNN 573 (SEQ ID NO: 81)

AAV1     QSSSTDPATGDVHAMGALPGMVWQDRDVYLQGPIWAKIPHTDGHFHPSPLMGGFGLKNPP 644 (SEQ ID NO: 82)
AAV6     QSSSTDPATGDVHVMGALPGMVWQDRDVYLQGPIWAKIPHTDGHFHPSPLMGGFGLKHPP 644 (SEQ ID NO: 83)
AAV3     QSSNTAPTTGTVNHQGALPGMVWQDRDVYLQGPIWAKIPHTDGHFHPSPLMGGFGLKHPP 644 (SEQ ID NO: 84)
AAV2     QRGNRQAATADVNTQGVLPGMVWQDRDVYLQGPIWAKIPHTDGHFHPSPLMGGFGLKHPP 643 (SEQ ID NO: 85)
AAV8     QQQNTAPQIGTVNSQGALPGMVWQNRDVYLQGPIWAKIPHTDGNFHPSPLMGGFGLKHPP 646 (SEQ ID NO: 86)
AAV8.1   QGQRQAAQIGTVNSQGALPGMVWQNRDVYLQGPIWAKIPHTDGNFHPSPLMGGFGLKHPP 646 (SEQ ID NO: 87)
AAV8 rh8 QAANTQAQTGLVHNQGVIPGMVWQNRDVYLQGPIWAKIPHTDGNFHPSPLMGGFGLKHPP 644 (SEQ ID NO: 88)
AAV10    QQANTGPIVGNVNSQGALPGMVWQNRDVYLQGPIWAKIPHTDGNFHPSPLMGGFGLKHPP 646 (SEQ ID NO: 89)
AAV7     QAANTAAQTQVVNNQGALPGMVWQNRDVYLQGPIWAKIPHTDGNFHPSPLMGGFGLKHPP 645 (SEQ ID NO: 90)
AAV9     QSAQAQAQTGWVQNQGILPGMVWQNRDVYLQGPIWAKIPHTDGNFHPSPLMGGFGMKHPP 644 (SEQ ID NO: 91)
AAV9.1   QSGQAQAATGWVQNQGILPGMVWQNRDVYLQGPIWAKIPHTDGNFHPSPLMGGFGMKHPP 644 (SEQ ID NO: 92)
AAV5     QSSTTAPATGTYNLQEIVPGSVWMERDVYLQGPIWAKIPETGAHFHPSPAMGGFGLKHPP 633 (SEQ ID NO: 93)
```

Figure 6C

| | | |
|---|---|---|
| AAV1 | PQILIK- 650 | (SEQ ID NO: 94) |
| AAV6 | PQILIK- 650 | (SEQ ID NO: 94) |
| AAV3 | PQIMIK- 650 | (SEQ ID NO: 95) |
| AAV2 | PQILIKN 650 | (SEQ ID NO: 96) |
| AAV8 | PQILIKN 653 | (SEQ ID NO: 96) |
| AAV8.1 | PQILIKN 653 | (SEQ ID NO: 96) |
| AAV8 rh8 | PQILIKN 651 | (SEQ ID NO: 96) |
| AAV10 | PQILIKN 653 | (SEQ ID NO: 96) |
| AAV7 | PQILIKN 652 | (SEQ ID NO: 96) |
| AAV9 | PQILIK- 650 | (SEQ ID NO: 94) |
| AAV9.1 | PQILIK- 650 | (SEQ ID NO: 94) |
| AAV5 | PMMLIKN 640 | (SEQ ID NO: 97) |

\* ::\*\*

FIG. 7A
Retinoschisin-1
*Homo sapiens*

```
  1 msrkiegfll lllfgyeatl glsstedege dpwyqkackc dcqggpnalw sagatsldci
 61 pecpyhkplg fesgevtpdq itcsnpeqyv gwysswtank arlnsqgfgc awlskfqdss
121 qwlqidlkei kvisgiltqg rcdidewmtk ysvqyrtder lnwiyykdqt gnnrvfygns
181 drtstvqnll rppiisrfir liplgwhvri airmellecv skca (SEQ ID NO:10)
```

FIG. 7B
BDNF
*Homo sapiens*

```
  1 mtilfltmvi syfgcmkaap mkeanirgqg glaypgvrth gtlesvngpk agsrgltsla
 61 dtfehvieel ldedhkvrpn eennkdadly tsrvmlssqv plepplifl eeyknyldaa
121 nmsmmvlrhs dparrgelsv cdsisewvta adkktavdms ggtvtvlekv pvskgqlkqy
181 fyetkcnpmg ytkegcrgid krhwnsqcrt tqsyvraltm dskkrigwrf iridtscvct
241 ltikrgr (SEQ ID NO:11)
```

FIG. 7C
RPE65
*Homo sapiens*

```
  1 msiqvehpag gykklfetve elsspltahv tgriplwltg sllrcgpglf evgsepfyhl
 61 fdgqallhkf dfkeghvtyh rrfirtdayv ramtekrivi tefgtcafpd pcknifsrff
121 syfrgvevtd nalvnvypvg edyyactetn fitkinpetl etikqvdlcn yvsvngatah
181 phiendgtvy nigncfgknf siaynivkip plqadkedpi skseivvqfp csdrfkpsyv
241 hsfgltpnyi vfvetpvkin lfkflsswsl wganymdcfe snetmgvvwlh iadkkrkkyl
301 nnkyrtspfn lfhhintyed ngflivdlcc wkgfefvyny lylanlrenw eevkknarka
361 pqpevrryvl plnidkadtg knlvtlpntt atailcsdet iwlepevlfs gprqafefpq
421 inyqkycgkp ytyaygigln hfvpdrickl nvktketwvw qepdsypsep ifvshpdale
481 eddgvvlsvv vspgagqkpa yllilnakdl sevaraevei nipvtfhglf kks (SEQ ID NO:12)
```

FIG. 7D
Peripherin-2
*Homo sapiens*

```
  1 mallkvkfdq kkrvklaqgl wlmnwfsvla giiifslglf lkielrkrsd vmnnseshfv
 61 pnsligmgvl scvfnslagk icydaldpak yarwkpwlkp ylaicvlfni ilflvalccf
121 llrgslentl ggglkngmky yrdtdtpgrc fmkktidmlq iefkccgnng frdwfeiqwi
181 snryldfssk evkdriksnv dgrylvdgvp fsccnpsspr pciqyqitnn sahysydhqt
241 eeinlwvrgc raallsyyss lmnsmgvvtl liwlfevtit iglrylqtsl dgvsnpeese
301 sesqgwller svpetwkafl esvkklgkgn qveaegadag qapeag (SEQ ID NO:13)
```

FIG. 7E
Peripherin
*Homo sapiens*

```
  1 mshhpsglra gfsstsyrrt fgpppslspg afsysssrf sssrllgsas psssvrlgsf
 61 rspragagal lrlpserldf smaealnqef latrsnekqe lqelndrfan fiekvrfleq
121 qnaalrgels qarqqepara dqlcqqelre lrreleligr erdrvqverd glaediaalk
181 qrleeetrkr edaehnlvlf rkdvddatls rlelerkies lmdeiefikk lheeelrdlq
241 vsvesqqvqq veveatvkpe ltaalrdira qyesiaaknl qeaeewyksk yadlsdaanr
301 nhealrqakq emnesrrqiq sltcevdglr gtneallrql releeqfale aggyqagaar
361 leeelrqlke emarhlreyq ellnvkmald ieiatyrkll egeesrisvp vhsfaslnik
421 ttvpeveppq dshsrktvli ktietrngev vtesqkeqrs eldkssahsy (SEQ ID NO:14)
```

FIG. 7F
RPGR-interacting protein-1
*Homo sapiens*

```
   1 mshlvdptsg dlpvrdidai plvlpaskgk nmktqpplsr mnreeledsf frlredhmlv
  61 kelswkqqde ikrlrttllr itaagrdirv aeeaaplset arrgqkagwr qrlsmhqrpq
 121 mhrlqghfhc vgpasprraq prvqvghrql htagapvpek pkrgprdrls ytappsfkeh
 181 atnenrgeva skpselvsgs nsiisfssvi smakpiglcm pnsahimasn tmqveeppks
 241 pekmwpkden feqrssleca qkaaelrasi kekvelirlk kllhernasl vmtkaqltev
 301 qeayetllqk ngqilsaahe allkqvnelr aelkeeskka vslksqledv silqmtlkef
 361 qervedleke rkllndnydk llesmldssd sssqphwsne liaeqlqqqv sqlqdqldae
 421 ledkrkrvlle lsrekaqned lklevtnilq khkqevellq naatisqppd rqsepathpa
 481 vlqentqiep sepknqeekk lsqvlnelqv shaettlele ktrdmlilqr kinvcyqeel
 541 eammtkadnd nrdhkekler ltrlidiknn rikqlegilr shdlptseql kdvaygtrpl
 601 sicletlpah gdedkvdisl lhqgenlfel hihqafltsa alaqagdtqp ttfctysfyd
 661 fethctplsv gpqplydfts qyvmetdslf lhylqeasar ldihqamase hstlaagwic
 721 fdrvletvek vhglatliga ggeefgvley wmrlrfpikp slqacnkrkk aqvylstdvl
 781 ggrkaqeeef rseswepqne lwieitkccg lrsrwlgtqp spyavyrfft fsdhdtaiip
 841 asnnpyfrdq arfpvlvtsd ldhylrreal sihvfdddedl epgsylgrar vpllplakne
 901 sikgdfnltd paekpngsiq vqldwkfpyi ppesflkpea qtkgkdtkds skisseeeka
 961 sfpsqdqmas pevpieaggy rskrkpphgg erkekehqvv sysrrkhgkr igvqgknrme
1021 ylslnilngn tpeqvnytew kfisetnsfig dgfknqheee emtlshsalk qkeplhpvnd
1081 kesseqgsev seaqtttdsdd vivppmsqky pkadsekmci eivslafype aevmsdenik
1141 qvvveykfyd lplsetetpv slrkpragee ihfhfskvid ldpqeqqgrr rflfdmlnqq
1201 dpdqghlkft vvsdpldeek keceevgyay lqlwqilesg rdileqeldi vspedlatpi
1261 grlkvslqaa avlhaiykem tedlfs (SEQ ID NO:15)
```

FIG. 7G
Rab escort protein-1

```
  1 madtlpsefd vivigtgipe siiaaacsrs grrvlhvdsr syyggnwasf sfsgllswlk
 61 eyqensdivs dspvwqdqil eneeaialsr kdktiqhvev fcyasqdlhe dveeagaiqk
121 nhalvtsans teaadsaflp tedeslstms cemlteqtps sdpenalevn gaevtgeken
181 hcddktcvps tsaedmsenv piaedtteqp kknritysqi ikegrrfnid lvskllysrg
241 llidlliksn vsryaefkni trilafregr veqvpcsrad vfnskqitmv ekrmlmkflt
301 fcmeyekypd eykgyeeitf yeylktqkit pnlqyivmhs iamtsetass tidglkatkn
361 flhclgrygn tpflfplygq gelpqcfcrm cavfggiycl rhsvqclvvd kesrkckaii
421 dqfggrlise hflvedsyfp enmcsrvqyr qisravlitd rsvlktdsdq qisiltvpae
481 epgtfavrvi elcsstmtcm kgtylvhltc tssktaredi esvvqklfvp ytemeieneq
541 vekprilwal yfnmrdssdi srscyndips nvyvcsgpdc gigndnavkq aetlfqeicp
601 nedfcppppn pediildgds lqpeasessa ipeansetfk estnlgnlee sse (SEQ ID NO:16)
```

FIG. 7H
212-amino acid isoform of RdCVF

```
  1 maslfsgril irnnsdqdel dteaevsrrl enrlvllffg agacpqcqaf vpilkdffvr
 61 ltdefyvlra aqlalvyvsq dsteeqqdlf lkdmpkkwlf ipfeddlrrd lgrqfsverl
121 pavvvlkpdg dvltrdgade iqrlgtacfa nwqeaaevld rnfqlpedle dqeprsltec
181 lrrhkyrvek aarggrdpgg gggeeggagg lf (SEQ ID NO:17)
```

FIG. 7I
156-amino acid isoform of RdCVF (isoform 1)

```
  1 mvdilgerhl vtckgatvea eaalqnkvva lyfaaarcap srdftplicd fytalvaear
 61 rpapfevvfv sadgssqeml dfmrelhgaw laipfhdpyr helrkrynvt aipklvivkq
121 ngevitnkgr kqirerglac fqdwveaadi fqnfsv (SEQ ID NO:18)
```

FIG. 7J
135-amino acid isoform of RdCVF (isoform 2)

```
  1 mvdilgerhl vtckgatvea eaalqnkvva lyfaaarcap srdftplicd fytalvaear
 61 rpapfevvfv sadgssqeml dfmrelhgaw laipfhdpyr qrslallprl ecsgvilahc
121 nlcllgssds lalas (SEQ ID NO:19)
```

FIG. 7K

Rod cGMP-specific 3',5'-cyclic phosphodiesterase subunit alpha (PDE6α)
GenBank NP_00431

```
  1 mgevtaeeve kfldsnigfa kqyynlihyra kliisdligak eaavdfsnyh spssmeesei
 61 ifdilrdfqe nlqtekcifn vmkklcfllq adrmslfmyr trngiaelat rlfnvhkdav
121 ledclvmpdq eivfpldmgi vghvahskki anvpnteede hfcdfvdilt eyktknilas
181 pimngkdvva iimavnkvdg shftkrdeei llkylnfanl imkvyhisyl hncetrggi
241 llwsgskvfe eltdiergfh kalytvrafi ncdrysvgli dmtkqkeffd vwpvlmgevp
301 pysgprtpdg reinfykvid yilhgkedik vipnpppdhw alvsglpayv aqnglicnim
361 napaedffaf qkepidesgw miknvlsmpi vnkkeeivgv atfynrkdgk pfdemdetlm
421 esltqfigws vlnpdtyesm nklenrkdif qdivkyhvkc dneeiqkilk trevygkepw
481 eceeeelaei lqaelpdadk yeinkfhfsd lpitelelvk cgiqmyyelk vvdkfhipqe
541 alvrfmysls kgyrkityhn wrhgfnvgqt mfsllvtgki kryftdieal amvtaafchd
601 idhrgtnnly qmksqnpiak lhgssilerh hiefgktllr desinifqnl nrrqhehaih
661 mmdiaiiatd lalyfkkrtm fgkivdqskt yeseqewtqy mmleqtrkei vmammmtacd
721 lsaitkpwev qsqvallvaa efweggdler tviqqnpipm mdrnkadelp klqvgfidfv
781 ctfvykefsr fheeitpmid gitnnrkewk aladeydakm kvqeekkqkq qsaksaaagn
841 qpggnpspgg attsksccig  (SEQ ID NO:102)
```

FIG. 7L

Rod cGMP-specific 3′,5′-cyclic phosphodiesterase subunit beta isoform 1 (PDE6β isoform 1) GenBank NP_000274

```
  1 mslseeqars fldqnpdfar qyfgkkispe nvaaacedgc ppdcdslrdi cqveestall
 61 elvqdmqesi nmervvfkvl rrictliqad rcslfmyrqr ngvaelatrl fsvqpdsvle
121 dclvppdsei vfpldigvvg hvaqtkkmvn vedvaecphf ssfadeltdy ktknmiatpi
181 mngkdvvavi mavnkingpf ftsededvfl kylnfatlyl kiyhlsylhn cetrrgqvll
241 wsankvfeel tdierqfhka fytvraylnc erysvglidm tkekeffdvw svlmgesqpy
301 sgprtpdgre ivfykvidyi lhgkeeikvi ptpsadhwal asglpsyvae sgficnimna
361 sademkfqe gaiddsgwli knvismpivn kkeeivgvat fynrkdgkpf deqdevlmes
421 itqflgwsvm ntdtydkmnk lenrkdiaqd mvlyhvkcdr deiqliliptr arigkepadc
481 dedelgeilk eelpgpttfd iyefhfsdle cteldlvkcg iqmyyelgvv rkfqipqevl
541 vrflfsiskg yrrityhnwr hgfnvaqtmf tllmtgkiks yytdleafam vtaglchdid
601 hrgtnnlyqm ksqnplaklh gssilerhhl efgkfilsee tiniyqninr rqhehvihlm
661 diaiiatdla lyfkkramfq kivdesknyq dkkswveyls lettrkeivm ammmtacdls
721 aitkpwevqs kvallvaaef weggdlertv ldqqpipmmd rnkaaelpkl qvgfidfvct
781 fvykefsrfh eeilpmfdri qnnrkewkal adeyeakvka leekeeeerv aakkvgteic
841 nggpapksst ccil (SEQ ID NO: 103)
```

FIG. 7M

Rod cGMP-specific 3',5'-cyclic phosphodiesterase subunit beta isoform 2 (PDE6β isoform 2) GenBank NP_001138763

```
  1 mslseeqars fldqnpdfar qyfgkklispe nvaaacedgc ppdcdslrdi cqveestall
 61 elvqdmqesi nmervvfkvl rrictliqad rcslfmyrqr ngvaelatri fsvqpdsvle
121 dclvppdsei vfpldigvvg hvaqtkkmvn vedvaecphf ssfadeltdy ktknmiatpi
181 mngkdvvavi mavnklngpf ftsededvfl kylnfatlyl kiyhlsylhn cetrrgqvll
241 wsankvfeel tdierqfhka fytvraylnc erysvglidm tkekeffdvw svlmgesqpy
301 sgprtpdgre ivfykvidyi lhgkeeikvi ptpsadhwal asglpsyvae sgficnimna
361 sademkfqe gaidddsgwli knvismpivn kkeeivgvat fynrkdgkpf deqdevlmes
421 itqflgwsvm ntdtydkmnk lenrkdiaqd mvlyhvkcdr deiqliliptr arlgkepadc
481 dedelgeilk eelpgpttfd iyefhfsdle cteldlvkcg iqmyyelgvv rkfqipqevl
541 vrflfsiskg yrrityhnwr hgfnvaqtmf tllmtgkiks yytdleafam vtaglchdid
601 hrgtnnlyqm ksqnplaklh gssilerhhl efgkfllsee tiniyqnlnr rqhehvihlm
661 diaiiatdla lyfkkramfq kivdesknyq dkkswveyls lettrkeivm ammmtacdls
721 aitkpwevqs kvallvaaef weggdlertv ldqqpipmmd rnkaaelpkl qvgfidfvct
781 fvykefsrfh eeilpmfdri qnnrkewkal adeyeakvka leekeeeerv aakkgteicn
841 ggpapksstc cil (SEQ ID NO: 104)
```

FIG. 7N

Rod cGMP-specific 3',5'-cyclic phosphodiesterase subunit beta isoform 3 (PDE6β isoform 3)
GenBank NP_001138764

```
  1 mtkekeffdv wsvlmgesqp ysgprtpdgr eivfykvidy iilhgkeeikv iptpsadhwa
 61 lasgipsyva esgficnimn asademfkfq egalddsgwl iknvlsmpiv nkkeeivgva
121 tfynrkdgkp fdeqdevlme sltqflgwsv mntdtydkmn klenrkdiaq dmvlyhvkcd
181 rdeiqlilpt rarlgkepad cdedelgeil keelgpttf diyefhfsdi ecteldivkc
241 giqmyyelgv vrkfqipqev lvrflfsisk gyrrityhnw rhgfnvaqtm ftllmtgklk
301 syytdleafa mvtagichdi dhrgtnnlyq mksqnplakl hgssilerhh lefgkfllse
361 etlniyqnin rrqhehvihl mdiaiiatdl alyfkkramf qkivdeskny qdkkswveyl
421 slettrkeiv mammmtacdl saitkpwevg skvallvaae fweggdlert vldqqpipmm
481 drnkaaelpk lqvgfidfvc tfvykefsrf heeilpmfdr lqnnrkewka ladeyeakvk
541 aleekeeeer vaakkvgtei cnggpapkss tccil (SEQ ID NO: 105)
```

FIG. 7O

Cyclic nucleotide-gated cation channel alpha-3 isoform 1 (CNGA3 isoform 1)
GenBank NP_001289

```
  1 makintqysh psrthikvkt sdrdlnraen glsrahssse etssvlqpgi ametrglads
 61 gqgsftgqgi arisrlifli rrwaarhvhh qdqgpdsfpd rfrgaelkev ssqesnaqan
121 vgsqepadrg rsawplakcn tntsnnteee kktkkkdaiv vdpssnlyyr witaialpvf
181 ynwylicra cfdelqseyl mlwlvldysa dvlyvldvlv rartgfleqg lmvsdtnrlw
241 qhyktttqfk ldvlslvptd laylkvgtny yfaiskfigf gtdswvypni sipehgrlsr kyiyslywst
301 frignlvlyi llilhwnaci yfaiskfigf vvvdflvgvl ifativgnvg smisnmnasr aefqakidsi
361 itlttigetp ppvkdeeylf fdylwankkt vdekeviksl pdklkaeiai nvhldtlkkv
421 kqymqfrkvt kdletrvirw fdylwankkt tvfspqdyic kkgdigkemy iinegklavv addgvtqfvv
481 rifqdceagl lvelviklrp tvfspqdyic gnrtanirs igysdlfcls kddlmealte ypeakkalee
541 isdgsyfgei silnikgsks gnrtanirs adpkdleekv eqlgssldtl qtrfarllae ynatqmkmkq
601 kgrqilmkdn lideeiarag evpgdatkte dkqq (SEQ ID NO: 106)
661 rlsqiesqvk gggdkpladg
```

FIG. 7P

Cyclic nucleotide-gated cation channel alpha-3 isoform 2 (CNGA3 isoform 2)
GenBank NP_001073347

```
  1 makintqysh psrthlkvkt sdrdinraen glsrahssse etssvlqpgi ametrglads
 61 gqgsftgqgi arlsrlifil rrwaarhvhh qdqgpdsfpd rfrgaelkev ssqesnaqan
121 vgsqepadrg rrkktkkkda ivvdpssnly yrwitaialp vfynwyliic racfdelqse
181 ylmiwlvidy sadvlyvldv ivrartgfle qgimvsdtnr lwqhyktttq fkldvlslvp
241 tdiaylkvgt nypevrfnrl ikfsrlifeff drtetrtnyp nmfrignivl yiliiihwna
301 ciyfaiskfi gfgtdswvyp nisipehgri srkyiyslyw stitlttige tpppvkdeey
361 lfvvvdflvg vlifativgn vgsmisnmna sraefqakid sikqymqfrk vtkdletrvi
421 rwfdylwank ktvdekevlk sipdklkaei ainvhldtlk kvrifqdcea gllvelvikl
481 rptvfspgdy ickkgdigke myiinegkla vvaddgvtqf vvisdgsyfg eisilinikgs
541 ksgnrrtani rsigysdifc iskddimeal teypeakkal eekgrqiimk dnlideelar
601 agadpkdlee kveqigssid tiqtrfarli aeynatqmkm kqrisqlesq vkgggdkpia
661 dgevpgdatk tedkqq (SEQ ID NO: 107)
```

FIG. 7Q

Cyclic nucleotide-gated cation channel beta-3 (CNGB3)
GenBank NP_061971

```
  1 mfksltkvnk vkpigennen eqssrrneeg shpsnqsqqt taqeenkgee kslktkstpv
 61 tseephtniq dklskknssg dlttnpdpqn aaeptgtvpe qkemdpgkeg pnspqnkppa
121 apvineyada qlhnlvkrmr qrtalykkl vegdisspea spqtakptav ppvkesddkp
181 tehyyrllwf kvkkmpitey lkriklpnsi dsytdrlyli willvtlayn wnccfiplrl
241 vfpyqtadni hywliadiic diiylydmlf iqprlqfvrg gdiivdsnel rkhyrtstkf
301 qldvasiipf dicylffgfn pmfranrmik ytsffefnhh lesimdkayi yrvirttgyl
361 lfilhinacv yywasnyegi gttrwvydge gneylrcyyw avrtlitigg lpepqtlfei
421 vfqlinffsg vfvfssligq mrdvigaata nqnyfracmd dtiaymnnys ipklvqkrvr
481 twyeytwdsq rmidesdilk tipttvqial aidvnfsiis kvdlfkgcdt qmiydmliri
541 ksvlylpgdf vckkgeigke myiikhgevq vlggpdgtkv lvtlkagsvf geisllaagg
601 gnrrtanvva hgfanlltld kktlqeilvh ypdserilmk karvllkqka ktaeatpprk
661 dlallfppke etpklfktli ggtgkaslar likkreqaa qkkensegge eegkenedkq
721 kenedkqken edkgkenedk dkgrepeekp ldrpectasp iaveeephsv rrtvlprgts
781 rqsliismap saeggeevlt ievkekakq (SEQ ID NO: 108)
```

FIG. 7R

Guanine nucleotide-binding protein G(t) subunit alpha-2 (GNAT2)
GenBank NP_005263

```
  1 mgsgasaedk elakrskele kklqedadke aktvkillig agesgkstiv kqmkiihqdg
 61 yspeeclefk ailygnvlqs ilaiiramtt igidyaepsc addgrqinnl adsieegtmp
121 pelvevirrl wkdgvqacf eraaeyqind sasyylnqie ritdpeylps eqdvlrsrvk
181 ttgiietkfs vkdlnfrmfd vggqrserkk wihcfegvtc iifcaalsay dmvleddev
241 nrmhesihlf nsicnhkffa atsivlfink kdlfeekikk vhisicfpey dgnnsyddag
301 nyiksqfldi nmrkdvkeiy shmtcatdtq nvkfvfdavt diiikenlkd cglf (SEQ ID NO: 109)
```

FIG. 7S

RPGR – 815 amino acids
GenBank NP_000319

```
  1 mrepeelmpd sgavftfgks kfaennpgkf wfkndvpvhl scgdehsavv tgnnklymfg
 61 snnwqiglg sksaiskptc vkalkpekvk laacgrnhtl vsteggnvya tggnneqqig
121 lgdteerntf hvisfftseh kikqlsagsn tsaaltedgr lfmwgdnseg qigiknvsnv
181 cvpqqvtigk pvswiscgyy hsafvtttdge lyvfgepeng klgipnqilg nhrtpqlvse
241 ipekviqvac ggehtvvite navytfglgq fgqlgigtfi fetsepkvie nirdqtisyi
301 scgenhtali tdigimytfg dgrhgklgig lenftnhfip tlcsnflrfi vklvacggch
361 mvvfaaphrg vakeiefdei ndtclsvatf lpyssitsgn vlqrtlsarm rrrererspd
421 sfsmrtlpp iegtlglsac flpnsvfprc sernlqesvl seqdlmqpee pdylldemtk
481 eaeidnsstv eslgettdil nmthimslns nekslkispv qkqkkqqtig eltqdtalte
541 nddsdeyeem semkegkack qhvsqgifmt qpattieafs deeveipeek egaedskgng
601 ieeqeveane envkvhggrk ekteilsddi tdkaedhefs kteelkledv deeinaenve
661 skkktvgdde svptgyhskt egaertndds saetiekkek anleeraice ynenpkgyml
721 ddadsssiei lensettpsk dmkktkkifl fkrvpsinqk ivknnneplp eiksigdqii
781 lksdnkdadq nhmsqnhqni pptnterrsk sctil (SEQ ID NO: 110)
```

FIG. 7T

RPGR – 646 amino acids
GenBank CAB54002

```
  1 mrepeelmpd sgavfitgks kfaennpgkf wfkndvpvhl scgdehsavv tgnnklymfg
 61 snnwqlglg sksaiskptc vkalkpekvk laacgrnhtl vsteggnvya tggnneqqig
121 lgdteerntf hvisfftseh kikqlsagsn tsaaltedgr lfmwgdnseg qiglknvsnv
181 cvpqqvtigk pvswiscgyy hsafvttdge lyvfgepeng klglpnqilg nhrtpqlvse
241 ipekviqvac gqehtvvite navytfglgq fgqlglgtfi fetsepkvie nirdqtisyi
301 scgenhtali tdiglmytfg dgrhgklglg lenftnhfip tlcsnflrfi vklvacggch
361 mvvfaaphrg vakeiefdei ndtclsvatf lpysslitsgn vlqrtlsarm rrererspd
421 sfsmrtlpp ieqtlglsac flpnsvfipr sernlqesvl seqdlmqpee pdylidemtk
481 eaeidnsstv eslgettdil nmthimslns neksklkispv qkqkkqqtig eltqdtalte
541 nddsdeyeem semkegkack qhvsqgifmt qpattieafs deeveipeek egaedskgng
601 ieeqeveane envkvhggrk ekteiisddl tdkaeysash sqivsv (SEQ ID NO: 111)
```

FIG. 7U

RPGR – 1152 amino acids

```
   1  mrepeelmpd sgavftfgks kfaennpgkf wfkndvpvhl scgdehsavv tgnnklymfg
  61  snnwqiglg sksaiskptc vkalkpekvk laacgrnhtl vsteggnvya tggnneqqig
 121  lgdteerntf hvisfftseh kikqisagsn tsaaltedgr lfmwgdnseg qigiknvsnv
 181  cvpqqvtigk pvswiscgyy hsafvttdge lyvfgepeng kigipnqilg nhrtpqlvse
 241  ipekviqvac ggehtvvite navytfgigq fgqlgigtfi fetsepkvie nirdqtisyi
 301  scgenhtali tdigimytfg dgrhgklgig lenftnhfip tlcsnflrfi vklvacggch
 361  mvvfaaphrg vakeiefdei ndtclsvatf lpyssitsgn vlqrtlsarm rrererspd
 421  sfsmrrtlpp iegtiglsac flpnsvfprc sernlqesvl seqdlmqpee pdylidemtk
 481  eaeidnsstv eslgettdil nmthimslns neksikispv qkqkkqqtig eltqdtalte
 541  nddsdeyeem semkegkack qhvsqgifmt qpattieafs deeveipeek egaedskgng
 601  ieeqeveane envkvhggrk ekteiisddi tdkaevsegk aksvgeaedg pegrgdgtce
 661  egssgaehwq deerekgekd kgrgemerpg egekelaeke ewkkrdgeeq eqkereqghq
 721  kernqemeeg geeehgegee eegdreeeee kegegkeege geevegerek eegerkkeer
 781  agkeekgeee gdqgegeeee tegrgeekee ggeveggeve egkgereeee eegegeeeeg
 841  egeeeegege eeegegkgee egeeegegek geeeegeeeg egeeeegege gegegegeeg
 901  egeeeegeg egeeegegeg egeeeegeg geeegeegeg gedgegegee eegewegeee
 961  egeeegeeeg egeeegeeege eegeegegeg eeeegeeeg eegegeeege gegeeeeege
1021  vegevegeeg egegeeeege eegeerekeg egeenrrnre eeeeeegkyq etgeeeenerg
1081  dgeeykkvsk ikgsvkygkh ktyqkksvtn tqgngkeqrs kmpvqskrll kngpsgskkf
1141  wnnvlphyle lk (SEQ ID NO: 112)
```

FIG. 7V

RPGR — 1020 amino acids

```
  1 mrepeelmpd sgavftfgks kfaennpgkf wfkndvpvhl scgdehsavv tgnnklymfg
 61 snnwqiglg  sksaiskptc vkalkpekvk laacgrnhtl vsteggnvya tggnneggig
121 lgdteerntf hvisfftseh kikqlsagsn tsaaltedgr lfmwgdnseg qiglknvsnv
181 cvpqqvtigk pvswiscgyy hsafvttdge lyvfgepeng klgipnqilg nhrtpqlvse
241 ipekviqvac ggehtvvlte navytfglgq fgqlgigtfl fetsepkvie nirdqtisyi
301 scgenhtali tdiglmytfg dgrhgklgig lenftnhfip tlcsnflrfi vklvacggch
361 mvvfaaphrg vakeiefdei ndtclsvatf lpyssltsgn vlqrtlsarm rrererspd
421 sfsmrrtlpp iegtglsac fipnsvfprc sernlqesvl seqdlmqpee pdylidemtk
481 eaeidnsstv eslgettdil nmthimslns nekslkispv qkqkkqqtig eltqdtalte
541 nddsdeyeem semkegkack qhvsqgifmt qpattieafs deevgndtgq vgpqadtdge
601 glqkevyrhe nngvdqida keiekesdgg hsqkeseaee idseketkla eiagmkdire
661 rekstkkmsp ffgnipdrgm nteseenkdf vkkresckqd vifdseresv ekpdsymega
721 sesqgiadg  fqqpeaiefs sgekeddeve tdqnirygrk lieqgneket kpliisksmak
781 ydfkcdrlse ipeekegaed skgngieeqe veaneenvkv hggrkektei isdditdkae
841 dhefskteel kledvdeein aenveskkkt vgddesvptg yhsktegaer tnddssaeti
901 ekkekaniee raiceynenp kgymidddads sstellense ttpskdmkkt kkiflfkrvp
961 sinqkivknn neplpeiksi gdqillksdn kdadqnhmsq nhqnipptnt errsksctil  (SEQ ID NO: 113)
```

FIG. 8A

AAV4 capsid
GenBank NP_044927

```
  1 mtdgylpdwl ednlsegvre wwalqpgapk pkanqqhqdn arglvlpgyk ylgpqngldk
 61 gepvnaadaa alehdkaydq qlkagdnpyl kynhadaefq qrlqgdtsfg gnlgravfqa
121 kkrvleplgl veqagetapg kkrpliespq qpdsstgigk kgkqpakkkl vfedetgagd
181 gppegstsga msddsemraa aggaaveggq gadgvgnasg dwhcdstwse ghvtttstrt
241 wvlptynnhl ykrlgeslqs ntyngfstpw gyfdnrfhc hfsprdwqrl innnwgmrpk
301 anrvkifniq vkevttsnge ttvannltst vqifadssye lpyvmdagqe gslppfpndv
361 fmvpqygycg lvtgntsqqq tdrnafycle yfpsqmlrtg nnfeitysfe kvpfhsmyah
421 sqsldrlmnp lidqylwglq stttgttlna gtattnftkl rptnfsnfkk nwlpgpsikq
481 qgfsktanqn ykipatgsds likyethstl dgrwsaltpg ppmatagpad skfsnsqlif
541 agpkqngnta tvpgtlifts eeelaatnat dtdmwgnlpg gdqsnsnipt vdrltalgav
601 pgmvwqnrdi yyqgpiwaki phtdghfhps pliggfglkh pppqifiknt pvpanpattf
661 sstpvnsfit qystgqvsvq idweiqkers krwnpevqft snygqqnsll wapdaagkyt
721 epraigtryl thhl (SEQ ID NO: 114)
```

FIG. 8B
Ancestral AAV capsid

MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADA
EFQERLQEDTSFGGNLGRAVFQAKKRVLEPLGLVEEGAKTAPGKKRPVEPSPQRSPDSSTGIGKKGQQPAKKRLNFGQTGDSESVPDPQPLGEPPAGP
SGLGSGTMAAGGAPMADNNEGADGVGNASGNWHCDSTWLGDRVITTSTRTWALPTYNNHLYKQISSXSXGXTNDNHYFGYSTPWGYFDFNRFHCHFS
PRDWQRLINNNWGFRPKRLNFKLFNIQVKEVTTNDGVTTIANNLTSTVQVFSDSEYQLPYVLGSAHQGCLPPFADVFMIPQYGYLTLNNGSQAVGRS
SFYCLEYFPSQMLRTGNNFTFSYTFEDVPFHSSYAHSQSLDRLMNPLIDQYLYYLXRTQSTGGTAGXXELLFSQXGPXXMSXQAKNWLPGPCYRQQRV
SKTIXQNNNSNFAWTGATKYHLNGRXSLVNPGVAMATHKDDEXRFFPSSGVLIFGKXGAGXNNTXIXNVMXTXEEEIKTTNPVATEXYGVVAXNLQSS
NTAPXTGXVNSQGALPGMVWQNRDVYLQGPIWAKIPHTDGNFHPSPLMGGFGLKHPPPQILIKNTPVPANPPPXXFXXAKFASFITQYSTGQVSVEIEW
ELQKENSKRWNPEIQYTSNYAKSXNVDFAVXXXGVYXEPRPIGTRYLTRNL (SEQ ID NO: 115)

(X is any amino acid)

FIG. 9 – Table 1
ONL

| | Fold increase in reads | Insert | Source library | Region |
|---|---|---|---|---|
| (SEQ ID NO: 29) | 63.79919679 | LQRGVRIPSVLEVNGQ | LS588 | Central |
| (SEQ ID NO: 31) | 7.153386879 | LQKADRQPGVVVVNCQ | LS588 | Peripheral |
| (SEQ ID NO: 24) | 2.181299886 | TGLDATRDHGLSPVTGT | Anc-7mer | Central |
| (SEQ ID NO: 26) | 1.975644028 | NGAVADYTRGLSPATGT | Anc-7mer | Peripheral |
| | 1.558702536 | 7m8 | 7m8 | CONTROL |
| (SEQ ID NO: 28) | 1.500800454 | LQKNARPASTESVNFQ | LS588 | Central |
| (SEQ ID NO: 27) | 1.371471857 | TGGDPTRGTGLSPVTGA | Anc-7mer | Peripheral |
| | 1.181900886 | k916 | k916 | CONTROL |
| | 1.180138343 | AAV24YF+ | AAV24YF+ | CONTROL |
| | 1.096454525 | AAV2 | AAV2 | CONTROL |
| (SEQ ID NO: 25) | 1.040515096 | TGSDGTRDHGLSPVTWT | Anc-7mer | Central |
| (SEQ ID NO: 30) | 0.915832658 | LQRGNRPVTTADVNTQ | LS588 | Peripheral |
| (SEQ ID NO: 5) | 0.821793827 | QAHQDTTKNA | AAV2-7mer | Peripheral |
| | 0.565046307 | k912 | k912 | CONTROL |
| (SEQ ID NO: 21) | 0.562635287 | TGVMHSQASGLS | AAV5-7mer | Peripheral |
| | 0.500833298 | k91 | k91 | CONTROL |
| (SEQ ID NO: 35) | 0.387792793 | LALIQDSMRA | AAV2-7mer | Central |
| (SEQ ID NO: 20) | 0.377253299 | TVVSTQAGIGLS | AAV5-7mer | Peripheral |
| (SEQ ID NO: 23) | 0.346854635 | TGSDMAHGTGLS | AAV5-7mer most abundant | CONTROL |
| (SEQ ID NO: 22) | 0.34669906 | TGDGSPAAPGLS | RPE-AAV5-7mer | Central |
| (SEQ ID NO: 100) | 0.324308359 | TGMHVTMMAGLN | AAV5-7mer | Central |
| (SEQ ID NO: 2) | 0.298540099 | LANQEHVKNA | AAV2-7mer | Peripheral |
| | 0.258738252 | AAV5 | AAV5 | CONTROL |
| (SEQ ID NO: 4) | 0.238979892 | LTHQDTTKNA | AAV2-7mer | Central |
| (SEQ ID NO: 99) | 0.161482878 | TGGHGSAPDGLS | RPE-AAV4-7mer | Central |
| (SEQ ID NO: 9) | 0.141133263 | TGGHDSSLDGLS | AAV4-7mer | Peripheral |
| (SEQ ID NO: 98) | 0.136923607 | TGDGGTTMNGLS | AAV4-7mer most abundant | CONTROL |
| (SEQ ID NO: 8) | 0.128082381 | TSPYGSSDGLS | AAV4-7mer | Peripheral |
| (SEQ ID NO: 6) | 0.090871196 | TGVMRSTNSGLN | AAV4-7mer | Central |
| | 0.057446852 | AAV4 | AAV4 | CONTROL |

FIG. 10 – Table 2
RPE

| | Fold increase in reads | Insert | Source library | Region |
|---|---|---|---|---|
| (SEQ ID NO: 29) | 33.65598086 | LQRGVRIPSVLEVNGQ | LS588 | Central |
| (SEQ ID NO: 35) | 4.627963274 | LALIQDSMRA | AAV2-7mer | Central |
| (SEQ ID NO: 4) | 4.155171929 | LTHQDTTKNA | AAV2-7mer | Central |
| (SEQ ID NO: 5) | 3.418111986 | QAHQDTTKNA | AAV2-7mer | Peripheral |
| | 3.307311067 | k91 | k91 | CONTROL |
| (SEQ ID NO: 2) | 2.250383296 | LANQEHVKNA | AAV2-7mer | Peripheral |
| (SEQ ID NO: 26) | 1.553340346 | NGAVADYTRGLSPATGT | Anc-7mer | Peripheral |
| (SEQ ID NO: 24) | 1.039956858 | TGLDATRDHGLSPVTGT | Anc-7mer | Central |
| (SEQ ID NO: 31) | 0.98426325 | LQKADRQPGVVVVNCQ | LS588 | Peripheral |
| (SEQ ID NO: 30) | 0.691860699 | LQRGNRPVTTADVNTQ | LS588 | Peripheral |
| | 0.584426815 | k916 | k916 | CONTROL |
| | 0.569675877 | AAV24YF+ | AAV24YF+ | CONTROL |
| | 0.563819035 | AAV2 | AAV2 | CONTROL |
| (SEQ ID NO: 28) | 0.515236441 | LQKNARPASTESVNFQ | LS588 | Central |
| (SEQ ID NO: 27) | 0.475479014 | TGGDPTRGTGLSPVTGA | Anc-7mer | Peripheral |
| (SEQ ID NO: 25) | 0.474443207 | TGSDGTRDHGLSPVTWT | Anc-7mer | Central |
| (SEQ ID NO: 21) | 0.405199224 | TGVMHSQASGLS | AAV5-7mer | Peripheral |
| (SEQ ID NO: 9) | 0.337284091 | TGGHDSSLDGLS | AAV4-7mer | Peripheral |
| (SEQ ID NO: 99) | 0.334179068 | TGGHGSAPDGLS | RPE-AAV4-7mer | Central |
| (SEQ ID NO: 8) | 0.292104518 | TSPYGSSDGLS | AAV4-7mer | Peripheral |
| | 0.25410362 | AAV5 | AAV5 | CONTROL |
| (SEQ ID NO: 98) | 0.208508888 | TGDGGTTMNGLS | AAV4-7mer most abundant | CONTROL |
| | 0.195373303 | 7m8 | 7m8 | CONTROL |
| | 0.175139543 | k912 | k912 | CONTROL |
| | 0.171857536 | AAV4 | AAV4 | CONTROL |
| (SEQ ID NO: 23) | 0.157923226 | TGSDMAHGTGLS | AAV5-7mer most abundant | CONTROL |
| (SEQ ID NO: 20) | 0.115992687 | TVVSTQAGIGLS | AAV5-7mer | Peripheral |
| (SEQ ID NO: 6) | 0.115792655 | TGVMRSTNSGLN | AAV4-7mer | Central |
| (SEQ ID NO: 22) | 0.046990066 | TGDGSPAAPGLS | RPE-AAV5-7mer | Central |
| (SEQ ID NO: 100) | 0.035004376 | TGMHVTMMAGLN | AAV5-7mer | Central |

FIG. 12C
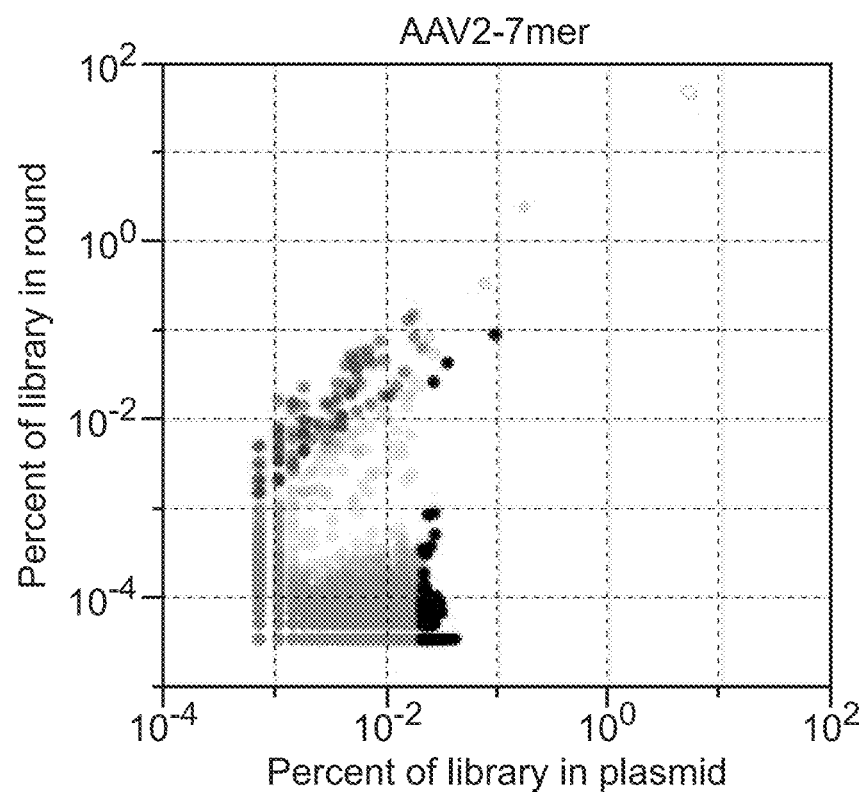
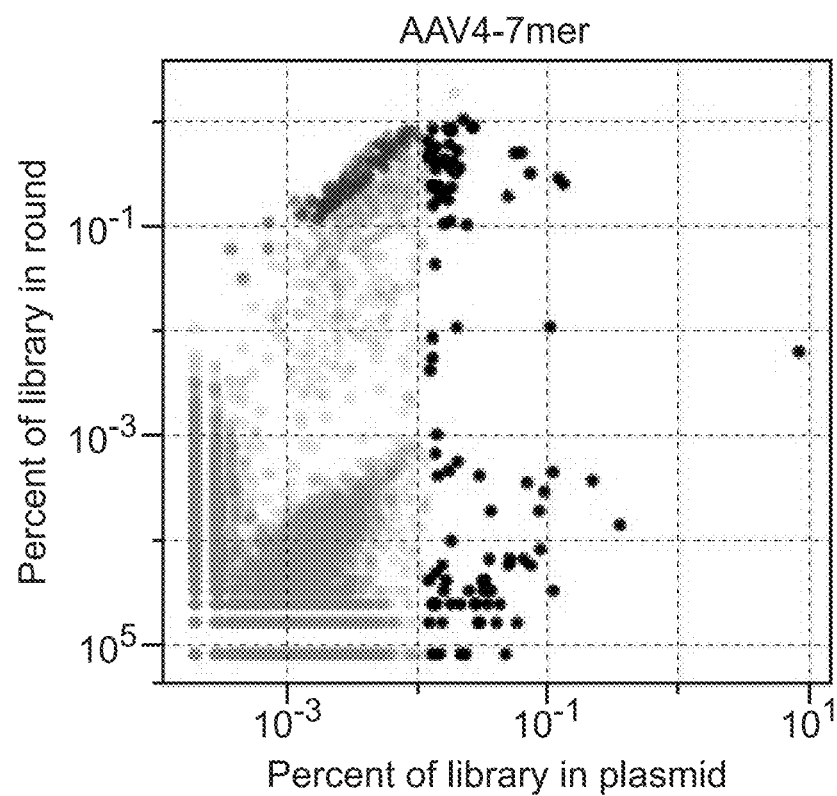

FIG. 12C (Cont.)
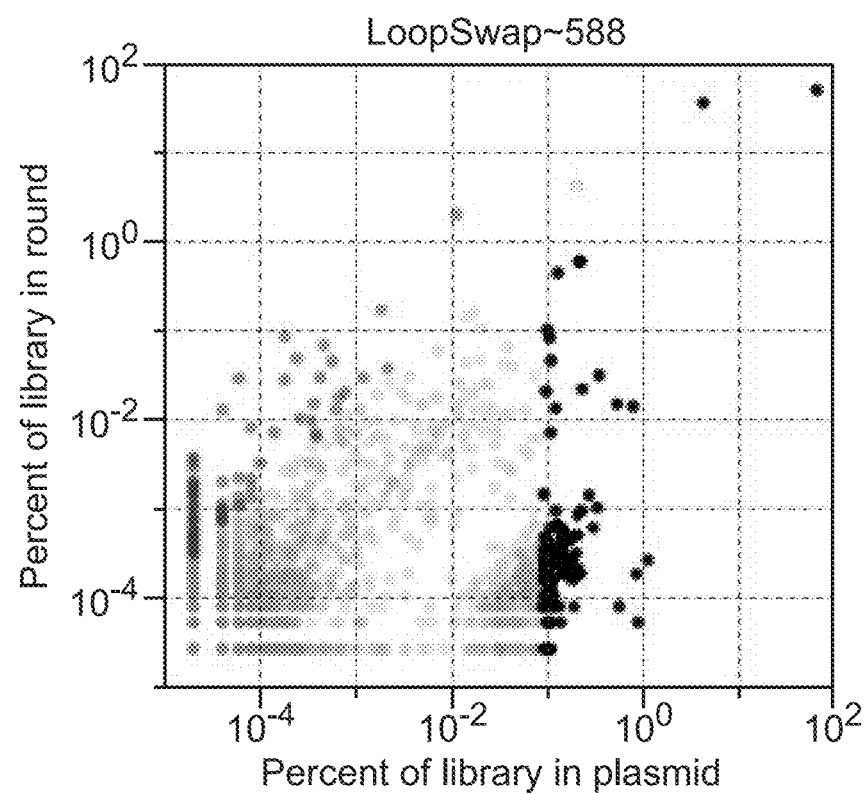
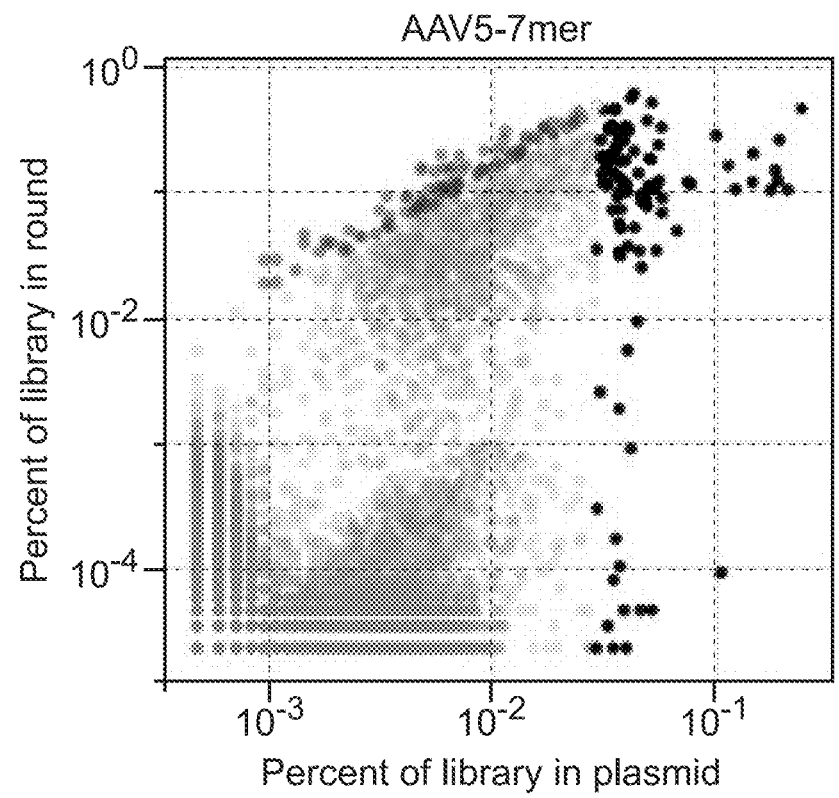

NHP outer retina
(33.66) LQRGVRIPSVLEVNGQ
(4.63) LALIQDSMRA
(4.16) LTHQDTTKNA
(3.42) QAHQDTTKNA
(3.31) LAHQDTTKNA
(2.25) LANQEHVKNA
(1.55) NGAVADYTRGLSPATGT
(1.04) TGLDATRDHGLSPVTGT
(0.98) LQKADRQPGVVVVNCQ
(0.69) LQRGNRPVTTADVNTQ
(0.58) PAPQDTTKKA
(0.57) AAV2 4YF+
(0.56) AAV2 control
(0.52) LQKNARPASTESVNFQ
(0.48) TGGDPTRGTGLSPVTGA
(0.47) TGSDGTRDHGLSPVTWT
(0.41) TGVMHSQASGLS
(0.34) TGGHDSSLDGLS
(0.25) AAV5 control
(0.20) LALGETTRPA
(0.18) LAPDSTTRSA
(0.17) AAV4 control
(0.12) TVVSTQAGIGLS

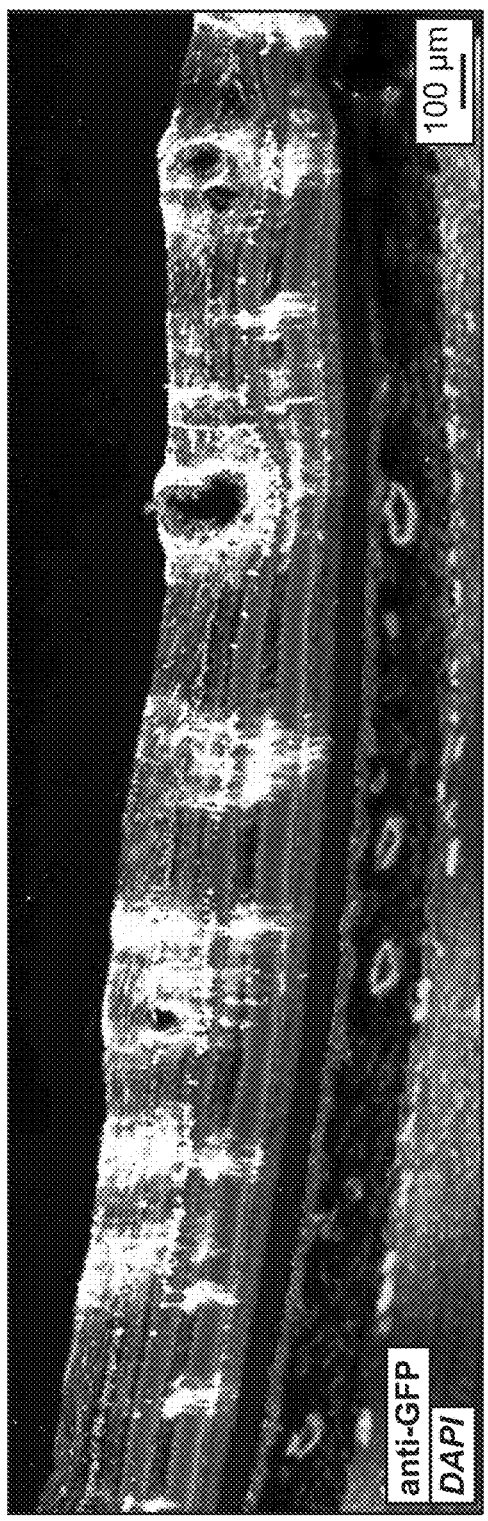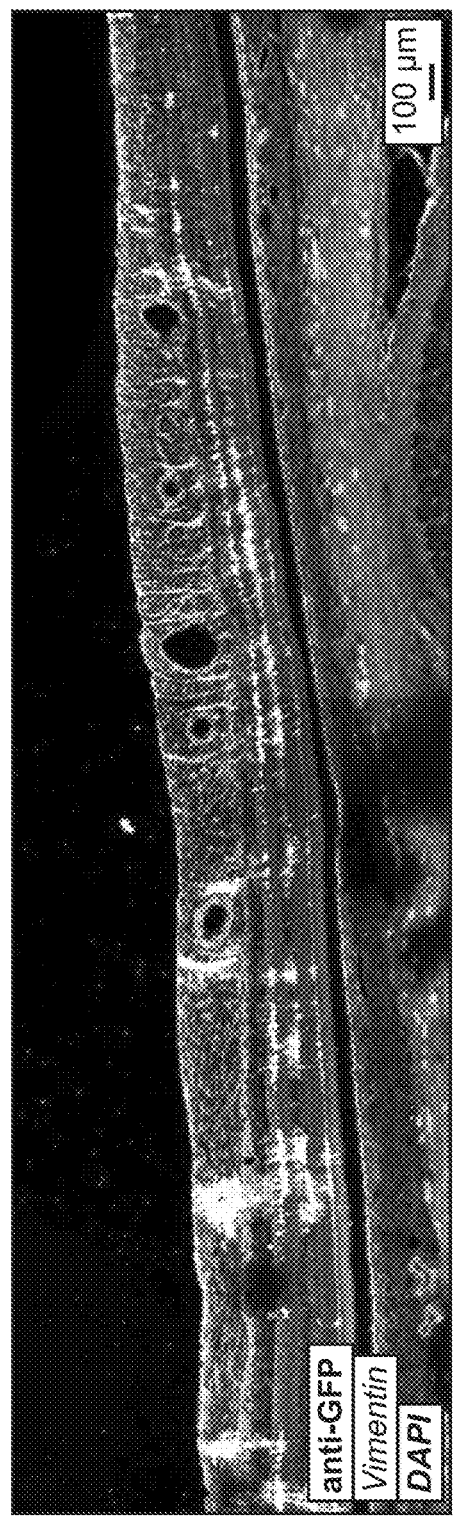

COMPOSITIONS AND METHODS OF TREATING OCULAR DISEASES

STATEMENT REGARDING FEDERALLY SPONSORED RESEARCH

This invention was made with government support under Grant No. 1R01EY022975-01A1 awarded by the National Institutes of Health. The government has certain rights in the invention.

INCORPORATION BY REFERENCE OF SEQUENCE LISTING PROVIDED AS A SEQUENCE LISTING XML FILE

A Sequence Listing is provided herewith as a Sequence Listing XML, BERK-355CON_SEQ_LIST_12_24.xml, created on Dec. 20, 2024 and having a size of 263,120 bytes. The contents of the Sequence Listing XML are incorporated herein by reference in their entirety.

INTRODUCTION

Vision is mediated by cells located in the retina, a thin, layered structure lining the back of the eye. Photoreceptors, which lie at the back of the retina, respond to the absorption of photons, initiating a stream of signal processing that passes through second and third order neurons in the retina, including bipolar, horizontal and amacrine cells. Retinal pigment epithelium (RPE) cells, which lie underneath photoreceptors, promote the regeneration of the photon-detecting molecule, 11-cis retinal, via the visual cycle pathway and hence are essential for promoting this photoreceptor function. Retinal ganglion cells (RGCs) in the inner retina receive visual signals from third order neurons, and communicate the visual signals in the form of action potentials to the brain.

Mutations in genes expressed in retinal cells, including transcripts in photoreceptors, RPE, bipolar cells and other cells, result in a breakdown of visual signal processing and retinal degeneration. Many of the mutations underlying retinal degenerative disease result in the death of photoreceptor and RPE cells.

Adeno-associated virus (AAV) belongs to the Parvoviridae family and Dependovirus genus, whose members require co-infection with a helper virus such as adenovirus to promote replication, and AAV establishes a latent infection in the absence of a helper. Virions are composed of a 25 nm icosahedral capsid encompassing a 4.7 kb single-stranded DNA genome with two open reading frames: rep and cap. The non-structural rep gene encodes four regulatory proteins essential for viral replication, whereas cap encodes three structural proteins (VP1-3) that assemble into a 60-mer capsid shell. This viral capsid mediates the ability of AAV vectors to overcome many of the biological barriers of transduction-including cell surface receptor binding, endocytosis, intracellular trafficking, and unpackaging in the nucleus.

SUMMARY

The present disclosure provides recombinant adeno-associated virus (AAV) virions with altered capsid protein, where the recombinant AAV (rAAV) virions exhibit greater ability to cross barriers between intravitreal fluid and retinal cells, and thus greater infectivity of a retinal cell compared to wild-type AAV, and where the rAAV virions comprise a heterologous nucleic acid. The present disclosure provides methods of delivering a gene product to a retinal cell in an individual.

BRIEF DESCRIPTION OF THE DRAWINGS

FIG. 2 provides a table of peptide insertions and peptide replacements in variant AAV capsids.

FIG. 3A-3C provide amino acid sequences of exemplary guide-RNA-directed endonucleases.

FIG. 4 provides an amino acid sequence of AAV2 capsid protein VP1 Amino acids 587 and 588 (NP) are in bold and underlined.

FIG. 5 provides amino acid sequences corresponding to amino acids 570-610 of AAV capsid protein VP1 of various AAV serotypes.

FIG. 6A-6C provide an alignment of amino acid sequences of AAV capsid protein loop IV (GH loop) regions. Insertion sites are shown in bold and underlining.

FIG. 7A-7V provide amino acid sequences of exemplary heterologous gene products.

FIG. 8A-8B provide amino acid sequences of AAV4 capsid (FIG. 8A) and an ancestral AAV capsid (FIG. 8B).

FIG. 9 provides Table 1. Table 1 provides a ranking of primate-derived variants and controls recovered from photoreceptors following injection of a green fluorescent protein (GFP)-Barcode library.

FIG. 10 provides Table 2. Table 2 provides a ranking of primate-derived variants and controls recovered from RPE cells following injection of a GFP-Barcode library.

DEFINITIONS

Figure 1:
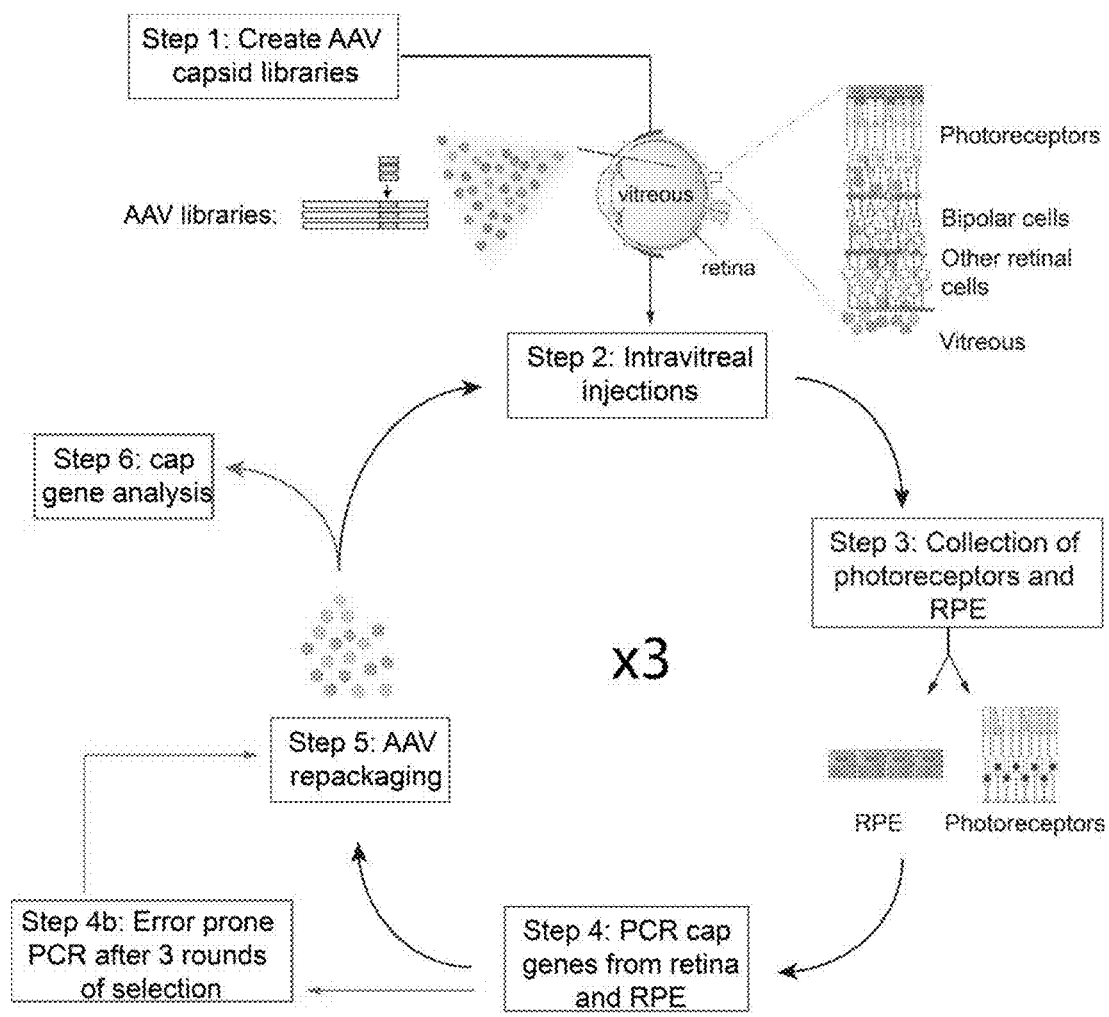
FIG. 1 provides a schematic depiction of the directed evolution methodology used to develop primate retinal AAV variants.

The term "retinal cell" can refer herein to any of the cell types that comprise the retina, such as retinal ganglion cells; amacrine cells; horizontal cells; bipolar cells; photoreceptor cells including rods and cones; Müller glial cells; astrocytes (e.g., a retinal astrocyte); and retinal pigment epithelium.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10), AAV type 11 (AAV-11), avian AAV, bovine AAV, canine AAV, equine AAV, primate AAV, non-primate AAV, and ovine AAV. See, e.g., Mori et al. (2004) Virology 330:375. The term "AAV" also includes chimeric AAV. "Primate AAV" refers to AAV isolated from a primate, "non-primate AAV" refers to AAV isolated from a non-primate mammal, "bovine AAV" refers to AAV isolated from a bovine mammal (e.g., a cow), etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is tropic. The term does not necessarily imply any replication capacity of the virus. As used herein, an "infectious" virus or viral particle is one that can access a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome (vg) copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA). Viral infectivity can be expressed as the ratio of infectious viral particles to total viral particles. Methods of determining the ratio of infectious viral particle to total viral particle are known in the art. See, e.g., Grainger et al. (2005) *Mol. Ther.* 11:S337 (describing a TCID50 infectious titer assay); and Zolotukhin et al. (1999) *Gene Ther.* 6:973.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wisconsin, USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

A "gene" refers to a polynucleotide containing at least one open reading frame that is capable of encoding a particular protein after being transcribed and translated.

The term "guide RNA", as used herein, refers to an RNA that comprises: i) an "activator" nucleotide sequence that binds to a guide RNA-directed endonuclease (e.g., a class 2 CRISPR/Cas endonuclease such as a type II, type V, or type VI CRISPR/Cas endonuclease) and activates the RNA-directed endonuclease; and ii) a "targeter" nucleotide sequence that comprises a nucleotide sequence that hybridizes with a target nucleic acid. The "activator" nucleotide sequence and the "targeter" nucleotide sequence can be on separate RNA molecules (e.g., a "dual-guide RNA"); or can be on the same RNA molecule (a "single-guide RNA").

A "small interfering" or "short interfering RNA" or siRNA is an RNA duplex of nucleotides that is targeted to a gene interest (a "target gene"). An "RNA duplex" refers to the structure formed by the complementary pairing between two regions of an RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV. As another example, a variant AAV capsid protein that comprises a heterologous peptide inserted into the GH loop of the capsid protein is a variant AAV capsid protein that includes an insertion of a peptide not normally included in a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses, camels, etc); mammalian farm animals (e.g., sheep, goats, cows, etc.); mammalian pets (dogs, cats, etc.); and rodents (e.g., mice, rats, etc.). In some cases, the individual is a human.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an rAAV virion" includes a plurality of such virions and reference to "the variant capsid protein" includes reference to one or more variant capsid proteins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides recombinant adeno-associated virus (AAV) virions with altered capsid protein, where the recombinant AAV (rAAV) virions exhibit greater ability to cross barriers between intravitreal fluid and retinal cells, and thus greater infectivity of a retinal cell compared to wild-type AAV, and where the rAAV virions comprise a heterologous nucleic acid. The present disclosure provides methods of delivering a gene product to a retinal cell in an individual. The present disclosure also provides methods of modifying a target nucleic acid present in a retinal cell.

The present disclosure provides recombinant adeno-associated virus (AAV) virions with altered capsid protein, where the recombinant AAV (rAAV) virions exhibit greater infectivity of a retinal cell compared to wild-type AAV; and where the rAAV virions comprise a heterologous nucleic acid. The rAAV virions exhibit increased ability to cross a barrier between intravitreal fluid and retinal cells. The rAAV virions exhibit greater infectivity of a retinal cell, compared to the infectivity of a corresponding wild-type AAV for the retinal cell. The retinal cell can be a photoreceptor (e.g., rods; cones), a retinal ganglion cell (RGC), a Müller cell (a Müller glial cell), an astrocyte (e.g., a retinal astrocyte), a bipolar cell, an amacrine cell, a horizontal cell, or a retinal pigment epithelium (RPE) cell. The present disclosure further provides methods of delivering a gene product to a retinal cell in an individual, and methods of treating an ocular disease. The present disclosure provides an rAAV virion with an altered capsid protein, where the rAAV virion exhibits at least 5-fold increased localization to one or more of the inner nuclear layer, the outer nuclear layer, the photoreceptor layer, the ganglion cell layer, and the retinal pigment epithelium, compared to the extent of localization to the inner nuclear layer, the outer nuclear layer, the photoreceptor layer, the ganglion cell layer, or the retinal pigment epithelium, by an AAV virion comprising the corresponding parental AAV capsid protein; and where the rAAV virions comprise a heterologous nucleic acid.

Variant AAV Capsid Polypeptides

The present disclosure provides a variant AAV capsid protein. As noted above, a variant AAV capsid protein of the present disclosure is altered, compared to a wild-type or other reference AAV capsid protein. Alterations include insertions and swaps (e.g., replacements of a contiguous stretch of amino acids with a different contiguous stretch of amino acids).

In some cases, a variant AAV capsid protein of the present disclosure comprises an insertion of a heterologous peptide of from 5 amino acids to 20 amino acids in length in an insertion site in a surface-accessible (e.g., solvent-accessible) portion of a parental AAV capsid protein, such that the variant capsid protein, when present in an AAV virion, confers increased infectivity of a retinal cell compared to the infectivity of the retinal cell by an AAV virion comprising the corresponding parental AAV capsid protein, particularly when the AAV virion is injected intravitreally. Thus, a variant AAV capsid protein of the present disclosure, when present in an AAV virion, confers increased ability of the AAV virion to cross a barrier between the intravitreal fluid ("vitreous") and a retinal cell, where such barriers include, e.g., the inner limiting membrane (ILM), the extracellular matrix of the retina, the cell membranes of the retinal cells themselves, inner nuclear layer, the outer nuclear layer, the photoreceptor layer, the ganglion cell layer, and the retinal pigment epithelium. In some cases, the retinal cell is a Müller cell. Other retinal cells include amacrine cells, bipolar cells, and horizontal cells. An "insertion of from about 5 amino acids to about 20 amino acids" is also referred to herein as a "peptide insertion" (e.g., a heterologous peptide insertion). A "corresponding parental AAV capsid protein" refers to an AAV capsid protein of the same AAV serotype, without a heterologous peptide insertion. In some instances, the variant AAV capsid comprises a single heterologous peptide insert of from 5 amino acids to 20 amino acids (e.g., from 5 to 7, from 7 to 10, from 10 to 12, from 12 to 15, or from 15 to 20 amino acids) in length.

An alteration in an AAV capsid can also be a swap, e.g., a replacement of a contiguous stretch of amino acids with a heterologous peptide. Thus, a replacement is an insertion of a heterologous peptide in place of a contiguous stretch of amino acids. In some cases, a variant AAV capsid protein of the present disclosure comprises replacement of a contiguous stretch of amino acids with a heterologous peptide of from 5 amino acids to 20 amino acids in length in a site in a surface-accessible (e.g., solvent-accessible) portion of a parental AAV capsid protein, such that the variant capsid protein, when present in an AAV virion, confers increased infectivity of a retinal cell compared to the infectivity of the retinal cell by an AAV virion comprising the corresponding parental AAV capsid protein, particularly when the AAV virion is injected intravitreally. Thus, a variant AAV capsid protein of the present disclosure, when present in an AAV virion, confers increased ability of the AAV virion to cross a barrier between the intravitreal fluid ("vitreous") and a retinal cell, where such barriers include, e.g., ILM, the extracellular matrix of the retina, the cell membranes of the retinal cells themselves, inner nuclear layer, the outer nuclear layer, the photoreceptor layer, the ganglion cell layer, and the retinal pigment epithelium. In some cases, the retinal cell is a Müller cell. Other retinal cells include amacrine cells, bipolar cells, and horizontal cells. A "replacement of from about 5 amino acids to about 20 amino acids" is also referred to herein as a "peptide swap" (e.g., a replacement of a contiguous stretch of amino acids with a heterologous peptide). A "corresponding parental AAV capsid protein" refers to an AAV capsid protein of the same AAV serotype, without a heterologous peptide. In some instances, the variant AAV capsid comprises a single heterologous peptide replacement of from 5 amino acids to 20 amino acids (e.g., from 5 to 7, from 7 to 10, from 10 to 12, from 12 to 15, or from 15 to 20 amino acids) in length.

For purposes of the following discussion, "insertion" refers to both insertion of a heterologous peptide without replacement of a contiguous stretch of amino acids, and to insertion of a heterologous peptide that replaces a contiguous stretch of amino acids.

The insertion site is in the GH loop, or loop IV, of the AAV capsid protein, e.g., in a solvent-accessible portion of the GH loop, or loop IV, of the AAV capsid protein. For the GH loop/loop IV of AAV capsid, see, e.g., van Vliet et al. (2006) *Mol. Ther.* 14:809; Padron et al. (2005) *J. Virol.* 79:5047; and Shen et al. (2007) *Mol. Ther.* 15:1955. For example, the insertion site can be within amino acids 411-650 of an AAV capsid protein, as depicted in FIG. 6A-6C. For example, the insertion site can be within amino acids 570-611 of AAV2, within amino acids 571-612 of AAV1, within amino acids 560-601 of AAV5, within amino acids 571 to 612 of AAV6, within amino acids 572 to 613 of AAV7, within amino acids 573 to 614 of AAV8, within amino acids 571 to 612 of AAV9, or within amino acids 573 to 614 of AAV10, as depicted in FIG. 5. In some cases, the insertion site is between amino acids 588 and 589 of an AAV2 capsid protein, or a corresponding insertion site in an AAV of a different serotype. In some cases, the insertion site is between amino acids 587 and 588 of an AAV2 capsid protein, or a corresponding insertion site in an AAV of a different serotype. In some cases, the insertion site is between amino acids 575 and 576 of an AAV2 capsid protein, or a corresponding insertion site in an AAV of a different serotype. In some cases, the insertion site is between amino acids 584 and 585 of an AAV2 capsid protein, or a corresponding insertion site in an AAV of a different serotype. In some cases, the insertion site is between amino acids 590 and 591 of an AAV2 capsid protein, or a corresponding insertion site in an AAV of a different serotype. In some cases, the insertion site is between amino acids 584 and 585 of an AAV4 capsid protein, or a corresponding insertion site in an AAV of a different serotype. In some cases, the insertion site is between amino acids 575 and 576 of an AAV5 capsid protein, or a corresponding insertion site in an AAV of a different serotype. In some cases, the site for replacement is between amino acids 584 and 598 of an AAV2 capsid protein, or a corresponding site in an AAV of a different serotype.

In some cases, a heterologous peptide of from about 5 amino acids to about 20 amino acids (e.g., from 5 to 7, from 7 to 10, from 10 to 12, from 12 to 15, or from 15 to 20 amino acids) in length is inserted in an insertion site in the GH loop or loop IV of the capsid protein relative to a corresponding parental AAV capsid protein. For example, the insertion site can be between amino acids 587 and 588 of AAV2, or between amino acids 588 and 589 of AAV2, or the corresponding positions of the capsid subunit of another AAV serotype. It should be noted that the insertion site 587/588 is based on an AAV2 capsid protein. A heterologous peptide of 5 amino acids to about 20 amino acids (e.g., from 5 to 7, from 7 to 10, from 10 to 12, from 12 to 15, or from 15 to 20 amino acids) in length can be inserted in a corresponding site in an AAV serotype other than AAV2 (e.g., AAV8, AAV9, etc.). Those skilled in the art would know, based on a comparison of the amino acid sequences of capsid proteins of various AAV serotypes, where an insertion site "corresponding to amino acids 587-588 of AAV2" would be in a capsid protein of any given AAV serotype. Sequences corresponding to amino acids 570-611 of capsid protein VP1 of AAV2 (see FIG. 4) in various AAV serotypes are shown in FIG. 5. See, e.g., GenBank Accession No. NP_049542 for AAV1; GenBank Accession No. NP_044927 for AAV4; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9; GenBank Accession No. AAT46337 for AAV10; and GenBank Accession No. AAO88208 for AAVrh10. See, e.g., Santiago-Ortiz et al. (2015) *Gene Ther.* 22:934 for ancestral AAV capsid.

For example, the insertion site can be between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, between amino acids 588 and 589 of AAV10, or between amino acids 585 and 586 of AAV4. The insertion sites are underlined in FIG. 5; the amino acid numbering is based on the numbering depicted in FIG. 5.

In some cases, a subject capsid protein includes a GH loop comprising an amino acid sequence having at least about 85%, at least about 90%, at least about 95%, at least about 98%, at least about 99%, or 100%, amino acid sequence identity to an amino acid sequence set forth in FIG. 6A-6C; and having an insertion of a heterologous peptide of from 5 to 20 amino acids (e.g., from 5 to 7, from 7 to 10, from 10 to 12, from 12 to 15, or from 15 to 20 amino acids) in length.

In some cases, a variant AAV capsid protein of the present disclosure comprises a replacement, or substitution, of a segment, or sequence of consecutive amino acids, in a surface-accessible (e.g., solvent-accessible) portion of a parental AAV capsid, such that the variant capsid protein, when present in an AAV virion, confers increased infectivity of a retinal cell compared to the infectivity of the retinal cell by an AAV virion comprising the corresponding parental AAV capsid protein, particularly when the AAV virion is injected intravitreally. Thus, a subject variant AAV capsid protein comprising the sequence substitution, when present in an AAV virion, confers increased ability of the AAV virion to cross a barrier between the vitreous and a retinal cell, where such barriers include, e.g., the inner limiting membrane, the extracellular matrix of the retina, and the cell membranes of the retinal cells themselves. A "replacement of from about 5 consecutive amino acids to about 25 consecutive amino acids" is also referred to herein as a "loop swap" (i.e. a heterologous peptide substitution). A "corresponding parental AAV capsid protein" in such instances refers to an AAV capsid protein of the same AAV serotype, without the subject loop swap. In some instances, the variant AAV capsid comprises a heterologous peptide substitution of from 5 contiguous amino acids to 25 contiguous amino acids, e.g. from 5 to 9, from 9 to 11, from 10 to 15, from 15 to 20, or from 20 to 25 amino acids in length.

In some cases, a heterologous peptide of from about 5 amino acids to about 25 amino acids (e.g., from 5 to 9, from 9 to 11, from 10 to 15, from 15 to 20, or from 20 to 25 amino acids) in length is substituted in for an equivalent number of consecutive amino acids in a corresponding parental AAV capsid protein. In some embodiments, the substitution begins at around amino acid 588 of AAV2, or the corresponding position of the capsid subunit of another AAV serotype, and ends at around amino acid 598 of AAV2 or the corresponding position of the capsid subunit of another AAV serotype. It should be noted that the residues 588-598 are based on an AAV2 VP1 capsid protein. A heterologous peptide of 5 amino acids to about 25 amino acids in length can be substituted into a corresponding site in an AAV serotype other than AAV2 (e.g., AAV8, AAV9, etc.). Those skilled in the art would know, based on a comparison of the amino acid sequences of capsid proteins of various AAV serotypes, where a substitution site "corresponding to amino acids 588-598 of AAV2" would be in a capsid protein of any given AAV serotype. The amino acid residue corresponding to amino acids 588-598 of capsid protein VP1 of AAV2 (see FIG. 4) in various AAV serotypes are shown in FIG. 5. See, e.g., GenBank Accession No. NP_049542 for AAV1; GenBank Accession No. NP_044927 for AAV4; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9, GenBank Accession No. AAT46337 for AAV10, and GenBank Accession No. AAO88208 for AAVrh10.

In some cases, a heterologous peptide of from about 5 amino acids to about 25 amino acids (e.g., from 5 to 9, from 9 to 11, from 10 to 15, from 15 to 20, or from 20 to 25 amino acids) in length is substituted in for an equivalent number of consecutive amino acids in a corresponding parental AAV capsid protein. In some embodiments, the substitution begins at around amino acid 585 of AAV2, or the corresponding position of the capsid subunit of another AAV serotype, and ends at around amino acid 598 of AAV2 or the corresponding position of the capsid subunit of another AAV serotype. It should be noted that the residues 585-598 are based on an AAV2 VP1 capsid protein. A heterologous peptide of 5 amino acids to about 25 amino acids in length can be substituted into a corresponding site in an AAV serotype other than AAV2 (e.g., AAV8, AAV9, etc.). Those skilled in the art would know, based on a comparison of the amino acid sequences of capsid proteins of various AAV serotypes, where a substitution site "corresponding to amino acids 585-598 of AAV2" would be in a capsid protein of any given AAV serotype. The amino acid residue corresponding to amino acids 585-598 of capsid protein VP1 of AAV2 (see FIG. 4) in various AAV serotypes are shown in FIG. 5. See, e.g., GenBank Accession No. NP_049542 for AAV1; GenBank Accession No. NP_044927 for AAV4; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9, GenBank Accession No. AAT46337 for AAV10, and GenBank Accession No. AAO88208 for AAVrh10.

Insertion/Replacement Peptides

As noted above, a heterologous peptide of from about 5 amino acids to about 20 amino acids in length is inserted into the GH loop of an AAV capsid, or replaces an equivalent number of consecutive amino acids in the GH loop of an AAV capsid. For simplicity, the term "insertion peptide" is used below to describe both a peptide that is inserted into a parental AAV capsid and a peptide that replaces a segment of contiguous amino acids in the GH loop of an AAV capsid. In some cases, the insertion peptide has a length of from 5 amino acids to 20 amino acids. In some cases, the insertion peptide has a length of from 7 amino acids to 15 amino acids. In some cases, the insertion peptide has a length of from 9 amino acids to 15 amino acids. In some cases, the insertion peptide has a length of from 9 amino acids to 12 amino acids. The insertion peptide has a length of 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, or 20 amino acids. In some cases, the insertion peptide has a length of 7 amino acids. In some cases, the insertion peptide has a length of 8 amino acids. In some cases, the insertion peptide has a length of 9 amino acids. In some cases, the insertion peptide has a length of 10 amino acids. In some cases, the insertion peptide has a length of 11 amino acids. In some cases, the insertion peptide has a length of 12 amino acids. In some cases, the insertion peptide has a length of 13 amino acids. In some cases, the insertion peptide has a length of 14 amino acids. In some cases, the insertion peptide has a length of 15 amino acids.

The peptide insert is, in some cases, a peptide of Formula I:

(SEQ ID NO: 136)
LA(L/N)(I/Q)(Q/E)(D/H)(S/V)(M/K)(R/N)A.

In some cases, a peptide of Formula I comprises the following amino acid sequence: (21) LALIQDSMRA (SEQ ID NO: 35). In some cases, a peptide of Formula I comprises the following amino acid sequence: (22) LANQEHVKNA (SEQ ID NO:2).

The peptide insert is, in some cases, a peptide of Formula II:

$TX_1X_2X_3X_4X_5X_6X_7X_8GLX_9$ (SEQ ID NO: 137), where:

$X_1$ is G, V, or S;

$X_2$ is V, E, P, G, D, M, A, or S;

$X_3$ is M, V, Y, H, G, S, or D;

$X_4$ is R, D, S, G, V, Y, T, H, or M;

$X_5$ is S, L, G, T, Q, P, or A;

$X_6$ is T, A, S, M, D, Q, or H;

$X_7$ is N, G, S, L, M, P, G, or A;

$X_8$ is S, G, D, N, A, I, P, or T; and $X_9$ is S or N.

Peptide inserts of Formula II include, but are not limited to: (1) TGVMRSTNSGLN (SEQ ID NO: 6); (2) TGEVDLAGGGLS (SEQ ID NO: 7); (3) TSPYSGSSDGLS (SEQ ID NO: 8); (4) TGGHDSSLDGLS (SEQ ID NO: 9); (5) TGDGGTTMNGLS (SEQ ID NO: 98); (6) TGGHGSAPDGLS (SEQ ID NO: 99); (7) TGMHVTMMAGLN (SEQ ID NO: 100); (8) TGASYLDNSGLS (SEQ ID NO: 101); (9) TVVSTQAGIGLS (SEQ ID NO: 135); (10) TGVMHSQASGLS (SEQ ID NO: 21); (11) TGDGSPAAPGLS (SEQ ID NO: 22); and (12) TGSDMAHGTGLS (SEQ ID NO: 23). In some cases, the peptide insert is (1) TGVMRSTNSGLN (SEQ ID NO: 6). In some cases, the peptide insert is (2) TGEVDLAGGGLS (SEQ ID NO: 7). In some cases, the peptide insert is (3) TSPYSGSSDGLS (SEQ ID NO: 8). In some cases, the peptide insert is (4) TGGHDSSLDGLS (SEQ ID NO: 9). In some cases, the peptide insert is (5) TGDGGTTMNGLS (SEQ ID NO: 98). In some cases, the peptide insert is (6) TGGHGSAPDGLS (SEQ ID NO: 99). In some cases, the peptide insert is (7) TGMHVTMMAGLN (SEQ ID NO: 100). In some cases, the peptide insert is (8) TGASYLDNSGLS (SEQ ID NO: 101). In some cases, the peptide insert is (9) TVVSTQAGIGLS (SEQ ID NO: 20). In some cases, the peptide insert is (10) TGVMHSQASGLS (SEQ ID NO: 21). In some cases, the peptide insert is (11) TGDGSPAAPGLS (SEQ ID NO: 22). In some cases, the peptide insert is (12) TGSDMAHGTGLS (SEQ ID NO: 23).

The peptide insert is, in some cases, a peptide of Formula III:
TGX$_1$X$_2$X$_3$X$_4$X$_5$X$_6$X$_7$GLS (SEQ ID NO: 138), where:
X$_1$ is V, E, P, G, D, M, A, or S;
X$_2$ is M, V, Y, H, G, S, or D;
X$_3$ is R, D, S, G, V, Y, T, H, or M;
X$_4$ is S, L, G, T, Q, P, or A;
X$_5$ is T, A, S, M, D, Q, or H;
X$_6$ is N, G, S, L, M, P, G, or A; and
X$_7$ is S, G, D, N, A, I, P, or T.

Peptide inserts of Formula III include, but are not limited to: (2) TGEVDLAGGGLS (SEQ ID NO: 7); (4) TGGHDSSLDGLS (SEQ ID NO: 9); (5) TGDGGTTMNGLS (SEQ ID NO: 98); (6) TGGHGSAPDGLS (SEQ ID NO: 99); (8) TGASYLDNSGLS (SEQ ID NO: 101); (10) TGVMHSQASGLS (SEQ ID NO: 21); (11) TGDGSPAAPGLS (SEQ ID NO: 22); and (12) TGSDMAHGTGLS (SEQ ID NO: 23).

The peptide insert is, in some cases, a peptide of Formula IV:
X$_1$GX$_2$X$_3$X$_4$X$_5$X$_6$X$_7$X$_8$GLSPX$_9$TX$_{10}$X$_{11}$ (SEQ ID NO: 139), where
X$_1$ is T or N;
X$_2$ is L, S, A, or G;
X$_3$ is D or V;
X$_4$ is A, G, or P;
X$_5$ is T or D;
X$_6$ isR or Y;
X$_7$ is D, T, or G;
X$_8$ is H, R, or T;
X$_9$ is V or A;
X$_{10}$ is G or W; and
X$_{11}$ is T or A.

Peptide inserts of Formula IV include, but are not limited to: (13) TGLDATRDHGLSPVTGT (SEQ ID NO: 24); (14) TGSDGTRDHGLSPVTWT (SEQ ID NO: 25); (15) NGAVADYTRGLSPATGT (SEQ ID NO: 26); and (16) TGGDPTRGTGLSPVTGA (SEQ ID NO: 27). In some cases, the peptide insert is (13) TGLDATRDHGLSPVTGT (SEQ ID NO: 24). In some cases, the peptide insert is (14) TGSDGTRDHGLSPVTWT (SEQ ID NO: 25). In some cases, the peptide insert is (15) NGAVADYTRGLSPATGT (SEQ ID NO: 26). In some cases, the peptide insert is (16) TGGDPTRGTGLSPVTGA (SEQ ID NO: 27).

The peptide insert is, in some cases, a peptide of Formula V:
TGX$_1$DX$_2$TRX$_3$X$_4$GLSPVTGT (SEQ ID NO: 140), where
X$_1$ is L, S, A, or G;
X$_2$ is A, G, or P;
X$_3$ is D, T, or G; and
X$_4$ is H, R, or T.

Peptide inserts of Formula V include, but are not limited to: (13) TGLDATRDHGLSPVTGT (SEQ ID NO: 24); (14) TGSDGTRDHGLSPVTWT (SEQ ID NO: 25); and (16) TGGDPTRGTGLSPVTGA (SEQ ID NO: 27).

The peptide insert is, in some cases, a peptide of Formula VI:
LQX$_1$X$_2$X$_3$RX$_4$X$_5$X$_6$X$_7$X$_8$X$_9$VNX$_{10}$Q (SEQ ID NO: 141), where
X$_1$ is K or R;
X$_2$ is N, G, or A;
X$_3$ is A, V, N, or D;
X$_4$ is P, I, or Q;
X$_5$ is A, P, or V;
X$_6$ is S, T, or G;
X$_7$ is T or V;
X$_8$ is E, L, A, or V;
X$_9$ is S, E, D, or V; and
X$_{10}$ is F, G, T, or C.

Peptides of Formula VI include, but are not limited to: (17) LQKNARPASTESVNFQ (SEQ ID NO: 28); (18) LQRGVRIPSVLEVNGQ (SEQ ID NO: 29); (19) LQRGNRPVTTADVNTQ (SEQ ID NO: 30); and (20) LQKADRQPGVVVVNCQ (SEQ ID NO: 31). In some cases, the peptide insert is (17) LQKNARPASTESVNFQ (SEQ ID NO: 28). In some cases, the peptide insert is (18) LQRGVRIPSVLEVNGQ (SEQ ID NO: 29). In some cases, the peptide insert is (19) LQRGNRPVTTADVNTQ (SEQ ID NO: 30). In some cases, the peptide insert is (20) LQKADRQPGVVVVNCQ (SEQ ID NO: 31). Any of the above-described peptide inserts can replace an equal number of contiguous amino acids in the GH loop of an AAV capsid polypeptide. For example, in some cases, a peptide of Formula VI:

$LQX_1X_2X_3l\ RX_4X_5X_6X_7X_8X_9VNX_{10}Q$ (SEQ ID NO: 141), where
$X_1$ is K or R;
$X_2$ is N, G, or A;
$X_3$ is A, V, N, or D;
$X_4$ is P, I, or Q;
$X_5$ is A, P, or V;
$X_6$ is S, T, or G;
$X_7$ is T or V;
$X_8$ is E, L, A, or V;
$X_9$ is S, E, D, or V; and
$X_{10}$ is F, G, T, or C, replaces a contiguous stretch of from 5 amino acids to 20 amino acids in the GH loop of an AAV capsid polypeptide. In other words, in some cases, an "insert peptide" replaces an endogenous peptide (e.g., a contiguous stretch of from 5 amino acids to 20 amino acids) present in in the GH loop of an AAV capsid polypeptide, resulting in a variant AAV capsid comprising a heterologous peptide in the GH loop. In some cases, the "insert peptide" replaces an endogenous contiguous stretch of amino acids of the same length as the insert peptide. Thus, for example, where the "insert peptide" has a length of 16 amino acids, in some cases, an endogenous contiguous stretch of 16 amino acids is replaced by the insert peptide.

Peptides of Formula VI include, but are not limited to: (17) LQKNARPASTESVNFQ (SEQ ID NO: 28); (18) LQRGVRIPSVLEVNGQ (SEQ ID NO: 29); (19) LQRGNRPVTTADVNTQ (SEQ ID NO:30); and (20) LQKADRQPGVVVVNCQ (SEQ ID NO: 31). In some cases, the peptide that replaces an endogenous amino acid sequence in the GH loop of an AAV capsid is (17) LQKNARPASTESVNFQ (SEQ ID NO: 28). In some cases, the peptide insert is (18) LQRGVRIPSVLEVNGQ (SEQ ID NO: 29). In some cases, the peptide that replaces an endogenous amino acid sequence in the GH loop of an AAV capsid is (19) LQRGNRPVTTADVNTQ (SEQ ID NO: 30). In some cases, the peptide that replaces an endogenous amino acid sequence in the GH loop of an AAV capsid is (20) LQKADRQPGVVVVNCQ (SEQ ID NO: 31).

In some cases, a peptide insert of any one of Formulas I-VI further includes one or two linker amino acids at the N-terminus of the peptide and/or one or more amino acids at the C-terminus of the peptide. For example, in some cases, a peptide insert comprises: Thr-Gly-[peptide of any one of Formulas I-VI]-Gly-Leu-Ser (SEQ ID NOs: 142 and 155-159). As another example, in some cases, a peptide insert comprises: Leu-Ala-[peptide of any one of Formulas I-VI]-Ala (SEQ ID NOs: 143-148). As another example, in some cases, a peptide insert comprises: Leu-Gln-[peptide of any one of Formulas I-VI]-Gln (SEQ ID NOs: 149-154). In some cases, a peptide insert does not include any linker amino acids.

In some embodiments, a subject rAAV virion capsid does not include any other amino acid substitutions, insertions, or deletions, other than an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein. In other embodiments, a subject rAAV virion capsid includes from 1 to about 25 amino acid insertions, deletions, or substitutions, compared to the parental AAV capsid protein, in addition to an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein. For example, in some embodiments, a subject rAAV virion capsid includes from 1 to about 5, from about 5 to about 10, from about 10 to about 15, from about 15 to about 20, or from about 20 to about 25 amino acid insertions, deletions, or substitutions, compared to the parental AAV capsid protein, in addition to an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein. In certain embodiments, the deletion of one or more amino acids (e.g., 1, 2, 3, 4, 5, 6, 7, 8, 9, 10, 11, 12, 13, 14, 15, 16, 17, 18, 19, or 20 amino acids) compared to the parental AAV capsid protein occurs at the site of peptide insertion.

In some cases, a variant AAV capsid polypeptide of the present disclosure does not include one, two, three, or four, of the following amino acid substitutions: Y273F, Y444F, Y500F, and Y730F.

In some cases, a variant AAV capsid polypeptide of the present disclosure comprises, in addition to an insertion peptide as described above, one, two, three, or four of the following amino acid substitutions: Y273F, Y444F, Y500F, and Y730F.

In some cases, a variant AAV capsid polypeptide of the present disclosure is a chimeric capsid, e.g., the capsid comprises a portion of an AAV capsid of a first AAV serotype and a portion of an AAV capsid of a second serotype; and comprises an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein.

Recombinant AAV Virions

The present disclosure provides a recombinant AAV (rAAV) virion comprising: i) a variant AAV capsid polypeptide of the present disclosure; and ii) a heterologous nucleic acid comprising a nucleotide sequence encoding a heterologous polypeptide (i.e., a non-AAV polypeptide).

In some cases, an rAAV virion of the present disclosure comprises a capsid protein comprising an amino acid sequence having at least about 85%, at least about 90%, at least about 95%, at least about 98%, or at least about 99%, amino acid sequence identity to the amino acid sequence provided in FIG. 4; and an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein. In some embodiments, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 4; and an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) between amino acids 587 and 588 relative to the amino acid sequence depicted in FIG. 4, or at a corresponding site relative to a corresponding parental AAV capsid protein.

In some cases, an rAAV virion of the present disclosure comprises a capsid protein comprising an amino acid sequence having at least about 85%, at least about 90%, at least about 95%, at least about 98%, or at least about 99%, amino acid sequence identity to the amino acid sequence provided in FIG. 4; and an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein. In some cases, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 4; and an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) between amino acids 585 and 598 relative to the amino acid sequence depicted in FIG. 4, or at a corresponding site relative to a corresponding parental AAV capsid protein.

In some embodiments, a subject rAAV virion comprises a capsid protein that includes a GH loop comprising an amino acid sequence having at least about 85%, at least about 90%, at least about 95%, at least about 98%, at least about 99%, or 100%, amino acid sequence identity to an amino acid sequence set forth in FIG. 5, and comprising an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) between the bolded and underlined amino acids.

In some embodiments, a subject rAAV virion comprises a capsid protein comprising an amino acid sequence having at least about 85%, at least about 90%, at least about 95%, at least about 98%, or at least about 99%, amino acid sequence identity to any one of the amino acid sequences provided in FIG. 6A-6C; and an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) between amino acids 587 and 588 of AAV2, or at a corresponding site relative to another AAV genotype. In some cases, the corresponding insertion site is a site as indicated by bold text and underlining in FIG. 6B.

An rAAV virion of the present disclosure exhibits at least 5-fold, at least 10-fold, at least 15-fold, at least 20-fold, at least 25-fold, at least 50-fold, or more than 50-fold, increased infectivity of a retinal cell, compared to the infectivity of the retinal cell by an AAV virion comprising the corresponding parental AAV capsid protein.

Whether a given rAAV virion exhibits increased infectivity of a retinal cell can be determined by detecting expression in a retinal cell of a heterologous gene product encoded by the rAAV virion, following intravitreal administration of the rAAV virion. For example, an rAAV virion of the present disclosure that comprises: a) a variant capsid of the present disclosure comprising a peptide insert or a peptide replacement, as described above; and b) a heterologous nucleotide sequence encoding a heterologous gene product, when administered intravitreally, results in a level of the heterologous gene product in a retinal cell, that is at least 2-fold, at least 5-fold, at least 10-fold, at least 15-fold, at least 20-fold, at least 25-fold, at least 50-fold, or more than 50-fold, greater than the level of the gene product in the retinal cell that results when a control rAAV virion that comprises: a) a control AAV capsid that does not comprises the peptide insert or the peptide replacement; and b) heterologous nucleotide sequence encoding the heterologous gene product is administered intravitreally.

Whether a given rAAV virion exhibits increased infectivity of a retinal cell can be determined by assessing a therapeutic effect of a therapeutic gene product encoded by the rAAV virion in a retinal cell. Therapeutic effects can include, e.g., a) a decrease in the rate of loss of visual function, e.g. visual field, visual acuity; b) an improvement in visual function, e.g. an improvement in visual field or visual acuity; c) a decrease in sensitivity to light, i.e. photophobia; a decrease in nystagmus; etc. For example, an rAAV virion of the present disclosure that comprises: a) a variant capsid of the present disclosure comprising a peptide insert or a peptide replacement, as described above; and b) a heterologous nucleotide sequence encoding a heterologous therapeutic gene product, when administered intravitreally, results in a therapeutic effect of the therapeutic gene product in a retinal cell, that is at least 2-fold, at least 5-fold, at least 10-fold, at least 15-fold, at least 20-fold, at least 25-fold, at least 50-fold, or more than 50-fold, greater than the therapeutic effect in the retinal cell that results when a control rAAV virion that comprises: a) a control AAV capsid that does not comprises the peptide insert or the peptide replacement; and b) heterologous nucleotide sequence encoding the heterologous therapeutic gene product is administered intravitreally. Tests for visual function are known in the art; and any such test can be used to determine whether an rAAV virion of the present disclosure exhibits increased infectivity of a retinal cell.

An rAAV virion of the present disclosure exhibits at least 5-fold, at least 10-fold, at least 15-fold, at least 20-fold, at least 25-fold, at least 50-fold, or more than 50-fold, increased ability to cross a barrier between the intravitreal fluid and a retinal cell, compared to the ability of a control rAAV virion comprising the corresponding parental AAV capsid protein (i.e., the AAV capsid protein without the insert peptide or replacement peptide).

In some cases, a subject rAAV virion exhibits at least 5-fold, at least 10-fold, at least 15-fold, at least 20-fold, at least 25-fold, at least 50-fold, or more than 50-fold, increased infectivity of a retinal cell, when administered via intravitreal injection, compared to the infectivity of the retinal cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a photoreceptor (rod or cone) cell, compared to the infectivity of the photoreceptor cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a photoreceptor (rod or cone) cell, when administered via intravitreal injection, compared to the infectivity of the photoreceptor cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of an RGC, compared to the infectivity of the RGC by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of an RGC, when administered via intravitreal injection, compared to the infectivity of the RGC by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of an RPE cell, compared to the infectivity of the RPE cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of an RPE cell, when administered via intravitreal injection, compared to the infectivity of the RPE cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a Müller cell, compared to the infectivity of the Müller cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a Müller cell, when administered via intravitreal injection, compared to the infectivity of the Müller cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a bipolar cell, compared to the infectivity of the bipolar cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a bipolar cell, when administered via intravitreal injection, compared to the infectivity of the bipolar cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of an amacrine cell, compared to the infectivity of the amacrine cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of an amacrine cell, when administered via intravitreal injection, compared to the infectivity of the amacrine cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a horizontal cell, compared to the infectivity of the horizontal cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a horizontal cell, when administered via intravitreal injection, compared to the infectivity of the horizontal cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a retinal astrocyte, compared to the infectivity of the retinal astrocyte by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a retinal astrocyte, when administered via intravitreal injection, compared to the infectivity of the retinal astrocyte by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased ability to cross extracellular matrix (ECM) of the retina, compared to the ability of an AAV virion comprising the corresponding parental AAV capsid protein to cross the ECM of the retina.

In some cases, a subject rAAV virion exhibits at least 5-fold, at least 10-fold, at least 15-fold, at least 20-fold, at least 25-fold, at least 50-fold, or more than 50-fold, increased ability, when administered via intravitreal injection, to cross extracellular matrix (ECM) of the retina, compared to the ability of an AAV virion comprising the corresponding parental AAV capsid protein to cross the ECM of the retina when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased ability to cross the internal limiting membrane (ILM), compared to the ability of an AAV virion comprising the corresponding parental AAV capsid protein to cross the ILM.

In some cases, a subject rAAV virion exhibits at least 5-fold, at least 10-fold, at least 15-fold, at least 20-fold, at least 25-fold, at least 50-fold, or more than 50-fold, increased ability, when administered via intravitreal injection, to cross the ILM, compared to the ability of an AAV virion comprising the corresponding parental AAV capsid protein to cross the ILM when administered via intravitreal injection.

A subject rAAV virion can cross the ILM, and can also traverse cell layers, including Müller cells, amacrine cells, etc., to reach the photoreceptor cells and or RPE cells. For example, a subject rAAV virion, when administered via intravitreal injection, can cross the ILM, and can also traverse cell layers, including Müller cells, amacrine cells, etc., to reach the photoreceptor cells and or RPE cells.

In some cases, a subject rAAV virion exhibits at least 5-fold, at least 10-fold, at least 15-fold, at least 20-fold, at least 25-fold, at least 50-fold, or more than 50-fold, increased localization to one or more of the inner nuclear layer, the outer nuclear layer, the photoreceptor layer, the ganglion cell layer, and the retinal pigment epithelium, compared to the extent of localization to the inner nuclear layer, the outer nuclear layer, the photoreceptor layer, the ganglion cell layer, or the retinal pigment epithelium, by an AAV virion comprising the corresponding parental AAV capsid protein.

In some cases, a subject rAAV virion, when injected intravitreally, exhibits at least 5-fold, at least 10-fold, at least 15-fold, at least 20-fold, at least 25-fold, at least 50-fold, or more than 50-fold, increased localization past the ILM, compared to the extent of localization past the ILM by an intravitreally injected control AAV virion comprising the corresponding parental AAV capsid protein. For example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the retinal pigment epithelium (RPE), compared to the extent of localization to the RPE layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the photoreceptor (PR) layer, compared to the extent of localization to the PR layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the inner nuclear layer, compared to the extent of localization to the inner nuclear layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the outer nuclear layer, compared to the extent of localization to the outer nuclear layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the ganglion cell layer, compared to the extent of localization to the ganglion cell layer by an intravitreally injected control AAV virion comprising the corresponding parental AAV capsid protein.

In some embodiments, a subject rAAV virion selectively infects a retinal cell, e.g., a subject rAAV virion infects a retinal cell with 10-fold, 15-fold, 20-fold, 25-fold, 50-fold, or more than 50-fold, specificity than a non-retinal cell, e.g., a cell outside the eye. For example, in some embodiments, a subject rAAV virion selectively infects a retinal cell, e.g., a subject rAAV virion infects a photoreceptor cell with 10-fold, 15-fold, 20-fold, 25-fold, 50-fold, or more than 50-fold, specificity than a non-retinal cell, e.g., a cell outside the eye.

In some embodiments, a subject rAAV virion selectively infects a photoreceptor cell, e.g., a subject rAAV virion infects a photoreceptor cell with 10-fold, 15-fold, 20-fold, 25-fold, 50-fold, or more than 50-fold, specificity than a non-photoreceptor cell present in the eye, e.g., a retinal ganglion cell, a Müller cell, etc.

In some embodiments, a subject rAAV virion exhibits at least 10-fold, at least 15-fold, at least 20-fold, at least 25-fold, at least 50-fold, or more than 50-fold, increased infectivity of a photoreceptor cell, when administered via intravitreal injection, compared to the infectivity of the photoreceptor cell by an AAV virion comprising the corresponding parental AAV capsid protein, when administered via intravitreal injection.

Gene Products

An rAAV virion of the present disclosure comprises a heterologous nucleic acid comprising a nucleotide sequence encoding one or more gene products (one or more heterologous gene products). In some cases, the gene product is a polypeptide. In some cases, the gene product is an RNA. In some cases, an rAAV virion of the present disclosure comprises a heterologous nucleotide sequence encoding both a heterologous nucleic acid gene product and a heterologous polypeptide gene product. Where the gene product is an RNA, in some cases, the RNA gene product encodes a polypeptide. Where the gene product is an RNA, in some cases, the RNA gene product does not encode a polypeptide. In some cases, an rAAV virion of the present disclosure comprises a single heterologous nucleic acid comprising a nucleotide sequence encoding a single heterologous gene product. In some cases, an rAAV virion of the present disclosure comprises a single heterologous nucleic acid comprising a nucleotide sequence encoding two heterologous gene products. Where the single heterologous nucleic acid encodes two heterologous gene products, in some cases, nucleotide sequences encoding the two heterologous gene products are operably linked to the same promoter. Where the single heterologous nucleic acid encodes two heterologous gene products, in some cases, nucleotide sequences encoding the two heterologous gene products are operably linked to two different promoters. In some cases, an rAAV virion of the present disclosure comprises a single heterologous nucleic acid comprising a nucleotide sequence encoding three heterologous gene products. Where the single heterologous nucleic acid encodes three heterologous gene products, in some cases, nucleotide sequences encoding the three heterologous gene products are operably linked to the same promoter. Where the single heterologous nucleic acid encodes three heterologous gene products, in some cases, nucleotide sequences encoding the three heterologous gene products are operably linked to two or three different promoters. In some cases, an rAAV virion of the present disclosure comprises two heterologous nucleic acids, each comprising a nucleotide sequence encoding a heterologous gene product.

In some cases, the gene product is a polypeptide-encoding RNA. In some cases, the gene product is an interfering RNA. In some cases, the gene product is an aptamer. In some cases, the gene product is a polypeptide. In some cases, the gene product is a therapeutic polypeptide, e.g., a polypeptide that provides clinical benefit. In some embodiments, the gene product is a site-specific nuclease that provide for site-specific knock-down of gene function. In some embodiments, the gene product is an RNA-guided endonuclease that provides for modification of a target nucleic acid. In some cases, the gene products are: i) an RNA-guided endonuclease that provides for modification of a target nucleic acid; and ii) a guide RNA that comprises a first segment that binds to a target sequence in a target nucleic acid and a second segment that binds to the RNA-guided endonuclease. In some cases, the gene products are: i) an RNA-guided endonuclease that provides for modification of a target nucleic acid; ii) a first guide RNA that comprises a first segment that binds to a first target sequence in a target nucleic acid and a second segment that binds to the RNA-guided endonuclease; and iii) a first guide RNA that comprises a first segment that binds to a second target sequence in the target nucleic acid and a second segment that binds to the RNA-guided endonuclease.

Interfering RNA

Where the gene product is an interfering RNA (RNAi), suitable RNAi include RNAi that decrease the level of an apoptotic or angiogenic factor in a cell. For example, an RNAi can be an shRNA or siRNA that reduces the level of a gene product that induces or promotes apoptosis in a cell. Genes whose gene products induce or promote apoptosis are referred to herein as "pro-apoptotic genes" and the products of those genes (mRNA; protein) are referred to as "pro-apoptotic gene products." Pro-apoptotic gene products include, e.g., Bax, Bid, Bak, and Bad gene products. See, e.g., U.S. Pat. No. 7,846,730.

Interfering RNAs could also be against an angiogenic product, for example vascular endothelial growth factor (VEGF) (e.g., Cand5; see, e.g., U.S. Patent Publication No. 2011/0143400; U.S. Patent Publication No. 2008/0188437; and Reich et al. (2003) *Mol. Vis.* 9:210); VEGF receptor-1 (VEGFR1) (e.g., Sirna-027; see, e.g., Kaiser et al. (2010) *Am. J. Ophthalmol.* 150:33; and Shen et al. (2006) *Gene Ther.* 13:225); or VEGF receptor-2 (VEGFR2) (Kou et al. (2005) *Biochem.* 44:15064). See also, U.S. Pat. Nos. 6,649, 596, 6,399,586, 5,661,135, 5,639,872, and 5,639,736; and 7,947,659 and 7,919,473.

Aptamers

Where the gene product is an aptamer, exemplary aptamers of interest include an aptamer against VEGF. See, e.g., Ng et al. (2006) *Nat. Rev. Drug Discovery* 5:123; and Lee et al. (2005) *Proc. Natl. Acad. Sci. USA* 102:18902. For example, a VEGF aptamer can comprise the nucleotide sequence 5'-cgcaaucagugaaugcuuauacauccg-3' (SEQ ID NO:3). Also suitable for use is a platelet-derived growth factor (PDGF)-specific aptamer, e.g., E10030; see, e.g., Ni and Hui (2009) *Ophthalmologica* 223:401; and Akiyama et al. (2006) *J. Cell Physiol.* 207:407).

Polypeptides

Where the gene product is a polypeptide, in some cases, the polypeptide is a polypeptide that enhances function of a retinal cell, e.g., the function of a rod or cone photoreceptor cell, a retinal ganglion cell, a Müller cell, a bipolar cell, an amacrine cell, a horizontal cell, or a retinal pigment epithelial cell. Exemplary polypeptides include neuroprotective polypeptides (e.g., glial cell derived neurotrophic factor (GDNF), ciliary neurotrophic factor (CNTF), neurotrophin-4 (NT4), nerve growth factor (NGF), and neurturin (NTN)); anti-angiogenic polypeptides (e.g., a soluble VEGF receptor; a VEGF-binding antibody; a VEGF-binding antibody fragment (e.g., a single chain anti-VEGF antibody); endostatin; tumstatin; angiostatin; a soluble Flt polypeptide (Lai et al. (2005) *Mol. Ther.* 12:659); an Fc fusion protein comprising a soluble Flt polypeptide (see, e.g., Pechan et al. (2009) *Gene Ther.* 16:10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-Xl; XIAP); and the like. Suitable polypeptides include, but are not limited to, glial derived neurotrophic factor (GDNF); fibroblast growth factor; fibroblast growth factor 2; neurturin (NTN); ciliary neurotrophic factor (CNTF); nerve growth factor (NGF); neurotrophin-4 (NT4); brain derived neurotrophic factor (BDNF; e.g., a polypeptide comprising an amino acid sequence having at least about 90%, at least about 95%, at least about 98%, at least about 99%, or 100%, amino acid sequence identity to a contiguous stretch of from about 200 amino acids to 247 amino acids of the amino acid sequence depicted in FIG. 7B (SEQ ID NO:11)); epidermal growth factor; rhodopsin; X-linked inhibitor of apoptosis; and Sonic hedgehog.

Suitable light-responsive opsins include, e.g., a light-responsive opsin as described in U.S. Patent Publication No. 2007/0261127 (e.g., channelrhodopsin-2; ChR2; Chop2); U.S. Patent Publication No. 2001/0086421; U.S. Patent Publication No. 2010/0015095; U.S. Patent Publication No. 2016/0002302; U.S. Patent Publication No. 2013/0347137; U.S. Patent Publication No. 2013/0019325; and Diester et al. (2011) *Nat. Neurosci.* 14:387. See, Thyagarajan et al. (2010) *J Neurosci.* 30(26):8745-8758; Lagali et al. (2008) *Nat Neurosci.* 11(6):667-675; Doroudchi et al. (2011) Mol Ther. 19(7):1220-1229; Henriksen et al. (2014) *J. Ophthalmic Vis. Res.* 9:374; Tomita et al. (2014) *Mol. Ther.* 22:1434.

Suitable polypeptides include light-gated ion channel polypeptides. See, e.g., Gaub et al. (2014) *Proc. Natl. Acad. Sci. USA* 111:E5574. For example, a suitable polypeptide is a light-gated ionotropic glutamate receptor (LiGluR). Expression of LiGluR in retinal ganglion cells and ON-bipolar cells, in the presence of a photoisomerizable compound, renders the cells responsive to light. LiGluR comprises a L439C substitution; see, Caporale et al. (2011) *Mol Ther.* 19:1212-1219; Volgraf et al. (2006) Nat Chem Biol. 2:47-52; and Gorostiza et al. (2007) Proc Natl Acad Sci USA. 104:10865-10870. Photoisomerizable compounds include, e.g., maleimide-azobenzene-glutamate 0 with peak efficiency at 460 nm ($MAG0_{460}$) $MAG0_{460}$ has the following structure:

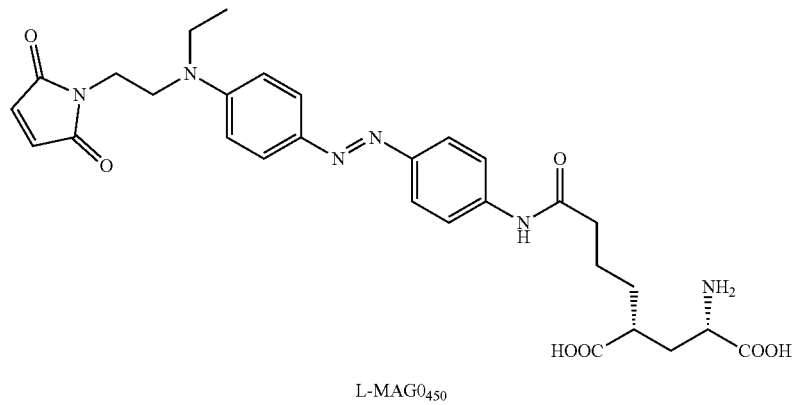 [SMILES: CCN(CCN1C(=O)C=CC1=O)c1ccc(/N=N/c2ccc(NC(=O)CCC[C@H](C[C@H](N)C(=O)O)C(=O)O)cc2)cc1]

L-$MAG0_{450}$

Suitable polypeptides also include retinoschisin (e.g., a polypeptide comprising an amino acid sequence having at least about 90%, at least about 95%, at least about 98%, at least about 99%, or 100%, amino acid sequence identity to a contiguous stretch of from about 200 amino acids to 224 amino acids of the amino acid sequence depicted in FIG. 7A (SEQ ID NO:10). Suitable polypeptides include, e.g., retinitis pigmentosa GTPase regulator (RPGR)-interacting protein-1 (see, e.g., GenBank Accession Nos. Q96KN7, Q9EPQ2, and Q9GLM3) (e.g., a polypeptide comprising an amino acid sequence having at least about 90%, at least about 95%, at least about 98%, at least about 99%, or 100%, amino acid sequence identity to a contiguous stretch of from about 1150 amino acids to about 1200 amino acids, or from about 1200 amino acids to 1286 amino acids, of the amino acid sequence depicted in FIG. 7F (SEQ ID NO:15); peripherin-2 (Prph2) (see, e.g., GenBank Accession No. NP_000313 (e.g., a polypeptide comprising an amino acid sequence having at least about 90%, at least about 95%, at least about 98%, at least about 99%, or 100%, amino acid sequence identity to a contiguous stretch of from about 300 amino acids to 346 amino acids of the amino acid sequence depicted in FIG. 7D (SEQ ID NO:13); and Travis et al. (1991) *Genomics* 10:733); peripherin (e.g., a polypeptide comprising an amino acid sequence having at least about 90%, at least about 95%, at least about 98%, at least about 99%, or 100%, amino acid sequence identity to a contiguous stretch of from about 400 amino acids to about 470 amino acids of the amino acid sequence depicted in FIG. 7E (SEQ ID NO:14); a retinal pigment epithelium-specific protein (RPE65), (e.g., a polypeptide comprising an amino acid sequence having at least about 90%, at least about 95%, at least about 98%, at least about 99%, or 100%, amino acid sequence identity to a contiguous stretch of from about 200 amino acids to 247 amino acids of the amino acid sequence depicted in FIG. 7C (SEQ ID NO:12)) (see, e.g., GenBank AAC39660; and Morimura et al. (1998) *Proc. Natl. Acad. Sci. USA* 95:3088); rod-derived cone viability factor (RdCVF) (e.g., a polypeptide comprising an amino acid sequence having at least about 90%, at least about 95%, at least about 98%, at least about 99%, or 100%, amino acid sequence identity to the amino acid sequence depicted in any one of FIGS. 7H, 7I, and 7J; Rab escort protein 1 (REP1) (e.g., a polypeptide comprising an amino acid sequence having at least about 90%, at least about 95%, at least about 98%, at least about 99%, or 100%, amino acid sequence identity to the amino acid sequence depicted in FIG. 7G); retinitis pigmentosa GTPase regulator (RPGR) (e.g., a polypeptide comprising an amino acid sequence having at least about 90%, at least about 95%, at least about 98%, at least about 99%, or 100%, amino acid sequence identity to the amino acid sequence depicted in one of FIG. 7S-7V); and the like. For example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 7S. As another example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 7T. example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 7U. example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 7V.

Suitable polypeptides also include: CHM (choroideremia (Rab escort protein 1 (REP1))), a polypeptide that, when defective or missing, causes choroideremia (see, e.g., Donnelly et al. (1994) *Hum. Mol. Genet.* 3:1017; and van Bokhoven et al. (1994) *Hum. Mol. Genet.* 3:1041); and Crumbs homolog 1 (CRB1), a polypeptide that, when defective or missing, causes Leber congenital amaurosis and retinitis pigmentosa (see, e.g., den Hollander et al. (1999) *Nat. Genet.* 23:217; and GenBank Accession No. CAM23328). For example, a suitable REP1 polypeptide can comprise an amino acid having at least about 90%, at least about 95%, at least about 98%, at least about 99%, or 100%, amino acid sequence identity to the amino acid sequence set depicted in FIG. 7G.

Suitable polypeptides include Rod cGMP-specific 3',5'-cyclic phosphodiesterase subunit alpha (PDE6a), Rod cGMP-specific 3',5'-cyclic phosphodiesterase subunit beta isoform 1 (PDE6β isoform 1), Rod cGMP-specific 3',5'-cyclic phosphodiesterase subunit beta isoform 2 (PDE6β isoform 2), Rod cGMP-specific 3',5'-cyclic phosphodiesterase subunit beta isoform 3 (PDE6β isoform 3). For example, a suitable PDE6a polypeptide can comprise an amino acid having at least about 90%, at least about 95%, at least about 98%, at least about 99%, or 100%, amino acid sequence identity to the amino acid sequence set depicted in FIG. 7K. As another example, a suitable PDE6β6 isoform 1 polypeptide can comprise an amino acid having at least about 90%, at least about 95%, at least about 98%, at least about 99%, or 100%, amino acid sequence identity to the amino acid sequence set depicted in FIG. 7L. As another example, a suitable PDE6β6 isoform 2 polypeptide can comprise an amino acid having at least about 90%, at least about 95%, at least about 98%, at least about 99%, or 100%, amino acid sequence identity to the amino acid sequence set depicted in FIG. 7M. As another example, a suitable PDE6β6 isoform 3 polypeptide can comprise an amino acid having at least about 90%, at least about 95%, at least about 98%, at least about 99%, or 100%, amino acid sequence identity to the amino acid sequence set depicted in FIG. 7N.

Suitable polypeptides also include polypeptides that, when defective or missing, lead to achromotopsia, where such polypeptides include, e.g., cone photoreceptor cGMP-gated channel subunit alpha (CNGA3) (see, e.g., GenBank Accession No. NP_001289; and Booij et al. (2011) *Ophthalmology* 118:160-167); cone photoreceptor cGMP-gated cation channel beta-subunit (CNGB3) (see, e.g., Kohl et al. (2005) *Eur J Hum Genet.* 13(3):302); guanine nucleotide binding protein (G protein), alpha transducing activity polypeptide 2 (GNAT2) (ACHM4); and ACHM5; and polypeptides that, when defective or lacking, lead to various forms of color blindness (e.g., L-opsin, M-opsin, and S-opsin). See Mancuso et al. (2009) *Nature* 461(7265):784-787.

For example, a suitable CNGA3 (also known as ACHM2) isoform 1 polypeptide can comprise an amino acid having at least about 90%, at least about 95%, at least about 98%, at least about 99%, or 100%, amino acid sequence identity to the amino acid sequence set depicted in FIG. 7O. As another example, a suitable CNGA3 (also known as ACHM2) isoform 2 polypeptide can comprise an amino acid having at least about 90%, at least about 95%, at least about 98%, at least about 99%, or 100%, amino acid sequence identity to the amino acid sequence set depicted in FIG. 7P.

As another example, a suitable CNGB3 (also known as ACHM3) polypeptide can comprise an amino acid having at least about 90%, at least about 95%, at least about 98%, at least about 99%, or 100%, amino acid sequence identity to the amino acid sequence set depicted in FIG. 7Q. As another example, GNAT2 (also known as ACHM4) can comprise an amino acid having at least about 90%, at least about 95%, at least about 98%, at least about 99%, or 100%, amino acid sequence identity to the amino acid sequence set depicted in FIG. 7R.

Site-Specific Endonucleases

In some cases, a gene product of interest is a site-specific endonuclease that provide for site-specific knock-down of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease can be targeted to the defective allele and knock out the defective allele. In some cases, a site-specific endonuclease is an RNA-guided endonuclease.

In addition to knocking out a defective allele, a site-specific nuclease can also be used to stimulate homologous recombination with a donor DNA that encodes a functional copy of the protein encoded by the defective allele. Thus, e.g., a subject rAAV virion can be used to deliver both a site-specific endonuclease that knocks out a defective allele, and can be used to deliver a functional copy of the defective allele, resulting in repair of the defective allele, thereby providing for production of a functional retinal protein (e.g., functional retinoschisin, functional RPE65, functional peripherin, etc.). See, e.g., Li et al. (2011) *Nature* 475:217. In some embodiments, a subject rAAV virion comprises a heterologous nucleotide sequence that encodes a site-specific endonuclease; and a heterologous nucleotide sequence that encodes a functional copy of a defective allele, where the functional copy encodes a functional retinal protein. Functional retinal proteins include, e.g., retinoschisin, RPE65, retinitis pigmentosa GTPase regulator (RGPR)-interacting protein-1, peripherin, peripherin-2, RdCVF, and the like.

Site-specific endonucleases that are suitable for use include, e.g., zinc finger nucleases (ZFNs); meganucleases; and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073. Suitable site-specific endonucleases include engineered meganucleases and re-engineered homing endonucleases. Suitable endonucleases include an I-TevI nuclease. Suitable meganucleases include I-SceI (see, e.g., Bellaiche et al. (1999) *Genetics* 152:1037); and I-CreI (see, e.g., Heath et al. (1997) *Nature Structural Biology* 4:468).

RNA-Guided Endonucleases

In some cases, the gene product is an RNA-guided endonuclease. In some cases, the gene product is an RNA comprising a nucleotide sequence encoding an RNA-guided endonuclease. In some cases, the gene product is a guide RNA, e.g., a single-guide RNA. In some cases, the gene products are: 1) a guide RNA; and 2) an RNA-guided endonuclease. The guide RNA can comprise: a) a protein-binding region that binds to the RNA-guided endonuclease; and b) a region that binds to a target nucleic acid. An RNA-guided endonuclease is also referred to herein as a "genome editing nuclease."

Examples of suitable genome editing nucleases are CRISPR/Cas endonucleases (e.g., class 2 CRISPR/Cas endonucleases such as a type II, type V, or type VI CRISPR/Cas endonucleases). A suitable genome editing nuclease is a CRISPR/Cas endonuclease (e.g., a class 2 CRISPR/Cas endonuclease such as a type II, type V, or type VI CRISPR/Cas endonuclease). In some cases, a genome targeting composition includes a class 2 CRISPR/Cas endonuclease. In some cases, a genome targeting composition includes a class 2 type II CRISPR/Cas endonuclease (e.g., a Cas9 protein). In some cases, a genome targeting composition includes a class 2 type V CRISPR/Cas endonuclease (e.g., a Cpf1 protein, a C2c1 protein, or a C2c3 protein). In some cases, a genome targeting composition includes a class 2 type VI CRISPR/Cas endonuclease (e.g., a C2c2 protein; also referred to as a "Cas13a" protein). Also suitable for use is a CasX protein. Also suitable for use is a CasY protein.

In some cases, a genome editing nuclease is a fusion protein that is fused to a heterologous polypeptide (also referred to as a "fusion partner"). In some cases, a genome editing nuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.).

In some cases, the genome-editing endonuclease is a Type II CRISPR/Cas endonuclease. In some cases, the genome-editing endonuclease is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 3A. In some cases, the Cas9 polypeptide used in a composition or method of the present disclosure is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 3B.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 3A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 3A, where amino acids N497, R661, Q695, and Q926 are substituted, e.g., with alanine.

In some cases, a suitable Cas9 polypeptide exhibits altered PAM specificity. See, e.g., Kleinstiver et al. (2015) *Nature* 523:481.

In some cases, the genome-editing endonuclease is a type V CRISPR/Cas endonuclease.

In some cases a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 3C.

In some cases, the genome-editing endonuclease is a CasX or a CasY polypeptide. CasX and CasY polypeptides are described in Burstein et al. (2017) *Nature* 542:237.

Enzymatically Inactive RNA-Guided Endonucleases

Also suitable for use is an RNA-guided endonuclease with reduced enzymatic activity. Such an RNA-guided endonuclease is referred to as a "dead" RNA-guided endonuclease; for example, a Cas9 polypeptide that comprises certain amino acid substitutions such that it exhibits substantially no endonuclease activity, but such that it still binds to a target nucleic acid when complexed with a guide RNA, is referred to as a "dead" Cas9 or "dCas9." In some cases, a "dead" Cas9 protein has a reduced ability to cleave both the complementary and the non-complementary strands of a double stranded target nucleic acid. For example, a "nuclease defective" Cas9 lacks a functioning RuvC domain (i.e., does not cleave the non-complementary strand of a double stranded target DNA) and lacks a functioning HNH domain (i.e., does not cleave the complementary strand of a double stranded target DNA). As a non-limiting example, in some cases, the nuclease defective Cas9 protein harbors mutations at amino acid positions corresponding to residues D10 and H840 (e.g., D10A and H840A) of SEQ ID NO: 15 (or the corresponding residues of a homolog of Cas9) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "nuclease defective Cas9", "dead Cas9" or simply "dCas9." Other residues can be mutated to achieve the above effects (i.e. inactivate one or the other nuclease portions). As non-limiting examples, residues D10, G12, G17, E762, H840, N854, N863, H982, H983, A984, D986, and/or A987 of *Streptococcus pyogenes* Cas9 (or the corresponding amino acids of a Cas9 homolog) can be altered (i.e., substituted). In some cases, two or more of D10, E762, H840, N854, N863, and D986 of *Streptococcus pyogenes* Cas9 (or the corresponding amino acids of a Cas9 homolog) are substituted. In some cases, D10 and N863 of *Streptococcus pyogenes* Cas9 (or the corresponding amino acids of a Cas9 homolog) are substituted with Ala. Also, mutations other than alanine substitutions are suitable.

In some cases, the genome-editing endonuclease is an RNA-guided endonuclease (and it corresponding guide RNA) known as Cas9-synergistic activation mediator (Cas9-SAM). The RNA-guided endonuclease (e.g., Cas9) of the Cas9-SAM system is a "dead" Cas9 fused to a transcriptional activation domain (wherein suitable transcriptional activation domains include, e.g., VP64, p65, MyoD1, HSF1, RTA, and SET7/9) or a transcriptional repressor domain (where suitable transcriptional repressor domains include, e.g., a KRAB domain, a NuE domain, an NcoR domain, a SID domain, and a SID4X domain) The guide RNA of the Cas9-SAM system comprises a loop that binds an adapter protein fused to a transcriptional activator domain (e.g., VP64, p65, MyoD1, HSF1, RTA, or SET7/9) or a transcriptional repressor domain (e.g., a KRAB domain, a NuE domain, an NcoR domain, a SID domain, or a SID4X domain). For example, in some cases, the guide RNA is a single-guide RNA comprising an MS2 RNA aptamer inserted into one or two loops of the sgRNA; the dCas9 is a fusion polypeptide comprising dCas9 fused to VP64; and the adaptor/functional protein is a fusion polypeptide comprising: i) MS2; ii) p65; and iii) HSF1. See, e.g., U.S. Patent Publication No. 2016/0355797.

Also suitable for use is a chimeric polypeptide comprising: a) a dead RNA-guided endonuclease; and b) a heterologous fusion polypeptide. Examples of suitable heterologous fusion polypeptides include a polypeptide having, e.g., methylase activity, demethylase activity, transcription activation activity, transcription repression activity, transcription release factor activity, histone modification activity, RNA cleavage activity, DNA cleavage activity, DNA integration activity, or nucleic acid binding activity.

Guide RNA

A nucleic acid that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Where the gene product is an RNA-guided endonuclease, or is both an RNA-guided endonuclease and a guide RNA, the gene product can modify a target nucleic acid. In some cases, e.g., where a target nucleic acid comprises a deleterious mutation in a defective allele (e.g., a deleterious mutation in a retinal cell target nucleic acid), the RNA-guided endonuclease/guide RNA complex, together with a donor nucleic acid comprising a nucleotide sequence that corrects the deleterious mutation (e.g., a donor nucleic acid comprising a nucleotide sequence that encodes a functional copy of the protein encoded by the defective allele), can be used to correct the deleterious mutation, e.g., via homology-directed repair (HDR).

In some cases, the gene products are an RNA-guided endonuclease and 2 separate sgRNAs, where the 2 separate sgRNAs provide for deletion of a target nucleic acid via non-homologous end joining (NHEJ).

In some cases, the gene products are: i) an RNA-guided endonuclease; and ii) one guide RNA. In some cases, the guide RNA is a single-molecule (or "single guide") guide RNA (an "sgRNA"). In some cases, the guide RNA is a dual-molecule (or "dual-guide") guide RNA ("dgRNA").

In some cases, the gene products are: i) an RNA-guided endonuclease; and ii) 2 separate sgRNAs, where the 2 separate sgRNAs provide for deletion of a target nucleic acid via non-homologous end joining (NHEJ). In some cases, the guide RNAs are sgRNAs. In some cases, the guide RNAs are dgRNAs.

In some cases, the gene products are: i) a Cpf1 polypeptide; and ii) a guide RNA precursor; in these cases, the precursor can be cleaved by the Cpf1 polypeptide to generate 2 or more guide RNAs.

The present disclosure provides a method of modifying a target nucleic acid in a retinal cell in an individual, where the target nucleic acid comprises a deleterious mutation, the method comprising administering to the individual (e.g., by intraocular; intravitreal; etc. administration) an rAAV virion of the present disclosure, where the rAAV virion comprises a heterologous nucleic acid comprising: i) a nucleotide sequence encoding an RNA-guided endonuclease (e.g., a Cas9 endonuclease); ii) a nucleotide sequence encoding a sgRNA that comprises a nucleotide sequence that is complementary to the target nucleic acid; and iii) a nucleotide sequence encoding a donor DNA template that comprises a nucleotide sequence that corrects the deleterious mutation. Administration of the rAAV virion results in correction of the deleterious mutation in the target nucleic acid by HDR.

The present disclosure provides a method of modifying a target nucleic acid in a retinal cell in an individual, where the target nucleic acid comprises a deleterious mutation, the method comprising administering to the individual (e.g., by intraocular; intravitreal; etc. administration) an rAAV virion of the present disclosure, where the rAAV virion comprises a heterologous nucleic acid comprising: i) a nucleotide sequence encoding an RNA-guided endonuclease (e.g., a Cas9 endonuclease); ii) a nucleotide sequence encoding a first sgRNA that comprises a nucleotide sequence that is complementary to a first sequence in the target nucleic acid; and iii) a nucleotide sequence encoding a second sgRNA that comprises a nucleotide sequence that is complementary to a second sequence in the target nucleic acid. Administration of the rAAV virion results in excision of the deleterious mutation in the target nucleic acid by NHEJ.

Regulatory Sequences

In some cases, a nucleotide sequence encoding a gene product of interest is operably linked to a transcriptional control element. For example, in some cases, a nucleotide sequence encoding a gene product of interest is operably linked to a constitutive promoter. In other cases, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a retinal cell-specific promoter. For example, in some instances, a nucleotide sequence encoding a gene product of interest is operably linked to a photoreceptor-specific regulatory element (e.g., a photoreceptor-specific promoter), e.g., a regulatory element that confers selective expression of the operably linked gene in a photoreceptor cell. Suitable photoreceptor-specific regulatory elements include, e.g., a rhodopsin promoter; a rhodopsin kinase promoter (Young et al. (2003) *Ophthalmol. Vis. Sci.* 44:4076); a beta phosphodiesterase gene promoter (Nicoud et al. (2007) *J. Gene Med.* 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) *Exp Eye Res.* 55:225).

Pharmaceutical Compositions

The present disclosure provides a pharmaceutical composition comprising: a) a subject rAAV virion, as described above; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

Methods of Delivering a Gene Product to a Retinal Cell and Treatment Methods

The present disclosure provides a method of delivering a gene product to a retinal cell in an individual, the method comprising administering to the individual a subject rAAV virion as described above. The gene product can be a polypeptide or an interfering RNA (e.g., an shRNA, an siRNA, and the like), an aptamer, or a site-specific endonuclease (e.g., an RNA-guided endonuclease), as described above. Delivering a gene product to a retinal cell can provide for treatment of a retinal disease. The retinal cell can be a photoreceptor, a retinal ganglion cell, a Müller cell, a bipolar cell, an amacrine cell, a horizontal cell, or a retinal pigmented epithelial cell. In some cases, the retinal cell is a photoreceptor cell, e.g., a rod or cone cell.

The present disclosure provides a method modifying a target nucleic acid in a retinal cell, the method comprising contacting the retinal cell with: 1) an rAAV virion of the present disclosure, wherein the rAAV virion comprises a heterologous nucleic acid comprising a nucleotide sequence encoding an RNA-guided endonuclease that binds a guide RNA; and 2) the guide RNA. The present disclosure provides a method modifying a target nucleic acid in a retinal cell, the method comprising contacting the retinal cell with an rAAV virion of the present disclosure, wherein the rAAV virion comprises a heterologous nucleic acid comprising a nucleotide sequence encoding: i) an RNA-guided endonuclease that binds a guide RNA; and ii) the guide RNA. In some cases, the method comprises contacting the retinal cell with a donor DNA template. In some cases, the RNA-guided endonuclease is a Cas9 polypeptide. In some cases, the guide RNA is a single-guide RNA.

The present disclosure provides a method of treating an ocular disease (e.g., a retinal disease), the method comprising administering to an individual in need thereof an effective amount of a subject rAAV virion as described above. A subject rAAV virion can be administered via intraocular injection, e.g. by intravitreal injection, by subretinal injection, by suprachoroidal injection, or by any other convenient mode or route of administration. Other convenient modes or routes of administration include, e.g., intravenous, intranasal, etc.

A "therapeutically effective amount" will fall in a relatively broad range that can be determined through experimentation and/or clinical trials. For example, for in vivo injection, i.e., injection directly into the eye, a therapeutically effective dose will be on the order of from about $10^6$ to about $10^{15}$ of the rAAV virions, e.g., from about $10^8$ to $10^{12}$ rAAV virions. For example, for in vivo injection, i.e., injection directly into the eye, a therapeutically effective dose will be on the order of from about $10^6$ viral genomes (vg) to about $10^{15}$ vg of the rAAV virions, e.g., from about $10^8$ vg to $10^{12}$ vg. For in vitro transduction, an effective amount of rAAV virions to be delivered to cells will be on the order of from about $10^8$ to about $10^{13}$ of the rAAV virions. For example, for in vitro transduction, an effective amount of rAAV virions to be delivered to cells will be on the order of from about $10^8$ to about $10^{13}$ vg of the rAAV virions. As another example, for in vitro transduction, an effective amount of rAAV virions to be delivered to cells will be on the order of from about 10 vg/cell to about $10^4$ vg/cell. Other effective dosages can be readily established by one of ordinary skill in the art through routine trials establishing dose response curves.

In some embodiments, more than one administration (e.g., two, three, four or more administrations) may be employed to achieve the desired level of gene expression. In some cases, the more than one administration is administered at various intervals, e.g., daily, weekly, twice monthly, monthly, every 3 months, every 6 months, yearly, etc. In some cases, multiple administrations are administered over a period of time of from 1 month to 2 months, from 2 months to 4 months, from 4 months to 8 months, from 8 months to 12 months, from 1 year to 2 years, from 2 years to 5 years, or more than 5 years.

Ocular diseases that can be treated using a subject method include, but are not limited to, acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; disorders of color vision, including achromatopsia, protanopia, deuteranopia, and tritanopia; and Bietti's crystalline dystrophy.

The present disclosure provides methods of treating retinal disease. The methods generally involve administering an rAAV virion of the present disclosure, or a composition comprising an rAAV virion of the present disclosure, to an eye of an individual in need thereof. Non-limiting methods for assessing treatment of retinal diseases include measuring functional changes, e.g. changes in visual acuity (e.g. BCVA), visual field (e.g. visual field perimetry), electrophysiological responsiveness to light and dark (e.g. ERG, VEP), color vision, and/or contrast sensitivity; measuring changes in anatomy or health using anatomical and/or photographic measures, e.g. OCT, fundus photography, and/or autofluorescence; and measuring ocular motility (e.g. nystagmus, fixation preference, and stability).

For example, one of ordinary skill in the art could readily determine an effective amount of rAAV virions by testing for an effect on one or more parameters, e.g. visual acuity, visual field, electrophysiological responsiveness to light and dark, color vision, contrast sensitivity, anatomy, retinal health and vasculature, ocular motility, fixation preference, and stability. In some cases, administering an effective amount of an rAAV virion of the present disclosure results in a decrease in the rate of loss of retinal function, anatomical integrity, or retinal health, e.g. a 2-fold, 3-fold, 4-fold, or 5-fold or more decrease in the rate of loss and hence progression of disease, e.g. a 10-fold decrease or more in the rate of loss and hence progression of disease. In some cases, administering an effective amount of an rAAV virion of the present disclosure results in a gain in retinal function, an improvement in retinal anatomy or health, and/or a stabilization in ocular motility, e.g. a 2-fold, 3-fold, 4-fold or 5-fold improvement or more in retinal function, retinal anatomy or health, and/or stability of the orbital, e.g. a 10-fold improvement or more in retinal function, retinal anatomy or health, and/or stability of the orbital.

Nucleic Acids and Host Cells

The present disclosure provides an isolated nucleic acid comprising a nucleotide sequence that encodes a subject variant adeno-associated virus (AAV) capsid protein as described above, where the variant AAV capsid protein comprises an insertion of from about 5 amino acids to about 20 amino acids in the GH loop or loop IV relative to a corresponding parental AAV capsid protein, or where the variant AAV capsid protein comprises a replacement of from about 5 amino acids to about 20 amino acids in the GH loop or loop IV relative to a corresponding parental AAV capsid protein with a heterologous peptide of from about 5 amino acids to about 20 amino acids; and where the variant capsid protein, when present in an AAV virion, provides for increased infectivity of a retinal cell compared to the infectivity of the retinal cell by an AAV virion comprising the corresponding parental AAV capsid protein. A subject isolated nucleic acid can be an AAV vector, e.g., a recombinant AAV vector.

Insertion Peptides

A variant AAV capsid protein encoded by a subject nucleic acid has an insertion peptide of from about 5 amino acids to about 20 amino acids in length is inserted into the GH loop of an AAV capsid. The insertion peptide has a length of 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, or 20 amino acids. Suitable insertion peptides are as described above. Suitable insertion peptides include a peptide of any one of Formulas I-VI, as described above. The insertion of the insertion peptide into a parental AAV capsid will in some cases replace an endogenous stretch of from about 5 amino acids to about 20 amino acids in the GH loop or loop IV. Thus, in some cases, a variant AAV capsid protein encoded by a subject nucleic acid comprises a replacement of from about 5 amino acids to about 20 amino acids in the GH loop or loop IV relative to a corresponding parental AAV capsid protein with a heterologous peptide of from about 5 amino acids to about 20 amino acids, where suitable heterologous peptides include a peptide of any one of Formulas I-VI, as described above.

A subject recombinant AAV vector can be used to generate a subject recombinant AAV virion, as described above. Thus, the present disclosure provides a recombinant AAV vector that, when introduced into a suitable cell, can provide for production of a subject recombinant AAV virion.

The present invention further provides host cells, e.g., isolated (genetically modified) host cells, comprising a subject nucleic acid. A subject host cell can be an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified with a subject nucleic acid. In other embodiments, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, 293T cells, COS cells, HeLa cells, Vero cells, 3T3 mouse fibroblasts, C3H10T1/2 fibroblasts, CHO cells, and the like. Non-limiting examples of suitable host cells include, e.g., HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. A subject host cell can also be made using a baculovirus to infect insect cells such as Sf9 cells, which produce AAV (see, e.g., U.S. Pat. No. 7,271,002; U.S. patent application Ser. No. 12/297,958)

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a subject host cell further comprises an rAAV vector. An rAAV virion can be generated using a subject host cell. Methods of generating an rAAV virion are described in, e.g., U.S. Patent Publication No. 2005/0053922 and U.S. Patent Publication No. 2009/0202490.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-63 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A recombinant adeno-associated virus (rAAV) virion comprising: a) a variant AAV capsid protein, wherein the variant AAV capsid protein comprises an insertion of a heterologous peptide of any one of Formulas I-VI, and wherein the variant capsid protein confers increased infectivity of a retinal cell compared to the infectivity of the retinal cell by a control AAV virion comprising the corresponding parental AAV capsid protein; and b) a heterologous nucleic acid comprising a nucleotide sequence encoding a heterologous gene product.

Aspect 2. The rAAV virion of aspect 1, wherein the rAAV virion exhibits at least 5-fold increased infectivity of a retinal cell compared to the infectivity of the retinal cell by a control AAV virion comprising the corresponding parental AAV capsid protein.

Aspect 3. The rAAV virion of aspect 1, wherein the rAAV virion exhibits at least 10-fold increased infectivity of a retinal cell compared to the infectivity of the retinal cell by an AAV virion comprising the corresponding parental AAV capsid protein.

Aspect 4. The rAAV virion of aspect 1, wherein the insertion of the heterologous peptide replaces a contiguous stretch of from 5 amino acids to 20 amino acids of the parental AAV capsid protein.

Aspect 5. The rAAV virion of aspect 1, wherein the insertion site is between amino acids corresponding to amino acids 570 and 611 of VP1 of AAV2, or the corresponding position in the capsid protein of another AAV serotype.

Aspect 6. The rAAV virion of aspect 4, wherein the insertion site is located between amino acids corresponding to amino acids 587 and 588 of VP1 of AAV2, or the corresponding position in the capsid protein of another AAV serotype; or wherein the insertion site is located between amino acids corresponding to amino acids 585 and 598 of VP1 of AAV2, or the corresponding position in the capsid protein of another AAV serotype.

Aspect 7. The rAAV virion of any one of aspects 1-6, wherein gene product is an interfering RNA or an aptamer.

Aspect 8. The rAAV virion of any one of aspects 1-6, wherein the gene product is a polypeptide.

Aspect 9. The rAAV virion of aspect 8, wherein the polypeptide is a neuroprotective polypeptide, an anti-angiogenic polypeptide, or a polypeptide that enhances function of a retinal cell.

Aspect 10. The rAAV virion of aspect 8, wherein the polypeptide is an RNA-guided endonuclease selected from a type II CRISPR/Cas polypeptide, a type V CRISPR/Cas polypeptide, and a type VI CRISPR/Cas polypeptide.

Aspect 11. The rAAV virion of aspect 10, wherein the RNA-guided endonuclease is an enzymatically inactive type II CRISPR/Cas polypeptide.

Aspect 12. The rAAV virion of aspect 10, wherein the gene product is an RNA-guided endonuclease and a guide RNA.

Aspect 13. The rAAV virion of any one of aspects 1-12, wherein the heterologous peptide is a peptide of Formula I: LA(L/N)(I/Q)(Q/E)(D/H)(S/V)(M/K)(R/N)A (SEQ ID NO: 136).

Aspect 14. The rAAV virion of any one of aspects 1-12, wherein the heterologous peptide comprises (21) LALIQDSMRA (SEQ ID NO: 35) or (22) LANQEHVKNA (SEQ ID NO: 2).

Aspect 15. The rAAV virion of any one of aspects 1-12, wherein the heterologous peptide is a peptide of Formula II: $TX_1X_2X_3X_4X_5X_6X_7X_8GLX_9$ (SEQ ID NO: 137), where:
$X_1$ is G, V, or S;
$X_2$ is V, E, P, G, D, M, A, or S;
$X_3$ is M, V, Y, H, G, S, or D;
$X_4$ is R, D, S, G, V, Y, T, H, or M;
$X_5$ is S, L, G, T, Q, P, or A;
$X_6$ is T, A, S, M, D, Q, or H;
$X_7$ is N, G, S, L, M, P, G, or A;
$X_8$ is S, G, D, N, A, I, P, or T; and
$X_9$ is S or N.

Aspect 16. The rAAV virion of any one of aspects 1-12, wherein the heterologous peptide comprises: (1) TGVMRSTNSGLN (SEQ ID NO: 6); (2) TGEVDLAGGGLS (SEQ ID No: 7); (3) TSPYSGSSDGLS (SEQ ID NO: 8); (4) TGGHDSSLDGLS (SEQ ID NO: 9); (5) TGDGGTTMNGLS (SEQ ID NO: 98); (6) TGGHGSAPDGLS (SEQ ID NO: 99); (7) TGMHVTMMAGLN (SEQ ID NO: 100); (8) TGASYLDNSGLS (SEQ ID NO: 101); (9) TVVSTQAGIGLS (SEQ ID NO: 135); (10)

TGVMHSQASGLS (SEQ ID NO: 21); (11) TGDGSPAAPGLS (SEQ ID NO: 22); or (12) TGSDMAHGTGLS (SEQ ID NO: 23)

Aspect 17. The rAAV virion of any one of aspects 1-12, wherein the heterologous peptide is a peptide of Formula III: TGX$_1$X$_2$X$_3$X$_4$X$_5$X$_6$X$_7$GLS (SEQ ID NO: 138), where:
X$_1$ is V, E, P, G, D, M, A, or S;
X$_2$ is M, V, Y, H, G, S, or D;
X$_3$ is R, D, S, G, V, Y, T, H, or M;
X$_4$ is S, L, G, T, Q, P, or A;
X$_5$ is T, A, S, M, D, Q, or H;
X$_6$ is N, G, S, L, M, P, G, or A; and
X$_7$ is 5, G, D, N, A, I, P, or T.

Aspect 18. The rAAV virion of any one of aspects 1-12, wherein the heterologous peptide comprises: (2) TGEVDLAGGGLS (SEQ ID NO: 7); (4) TGGHDSSLDGLS (SEQ ID NO: 9); (5) TGDGGTTMNGLS (SEQ ID NO: 98); (6) TGGHGSAPDGLS (SEQ ID NO: 99); (8) TGASYLDNSGLS (SEQ ID NO: 101); (10) TGVMHSQASGLS (SEQ ID NO: 21); (11) TGDGSPAAPGLS (SEQ ID NO: 22); or (12) TGSDMAHGTGLS (SEQ ID NO: 23).

Aspect 19. The rAAV virion of any one of aspects 1-12, wherein the heterologous peptide is a peptide of Formula IV: X$_1$GX$_2$X$_3$X$_4$X$_5$X$_6$X$_7$X$_8$GLSPX$_9$TX$_{10}$X$_{11}$ (SEQ ID NO: 139), where
X$_1$ is T or N;
X$_2$ is L, S, A, or G;
X$_3$ is D or V;
X$_4$ is A, G, or P;
X$_5$ is T or D;
X$_6$ is R or Y;
X$_7$ is D, T, or G;
X$_8$ is H, R, or T;
X$_9$ is V or A;
X$_{10}$ is G or W; and
X$_{11}$ is T or A.

Aspect 20. The rAAV virion of any one of aspects 1-12, wherein the heterologous peptide comprises: (13) TGLDATRDHGLSPVTGT (SEQ ID NO: 24); (14) TGSDGTRDHGLSPVTWT (SEQ ID NO: 25); (15) NGAVADYTRGLSPATGT (SEQ ID NO: 26); or (16) TGGDPTRGTGLSPVTGA (SEQ ID NO: 27).

Aspect 21. The rAAV virion of any one of aspects 1-12, wherein the heterologous peptide is a peptide of Formula V: TGX$_1$DX$_2$TRX$_3$X$_4$GLSPVTGT (SEQ ID NO: 140), where
X$_1$ is L, S, A, or G;
X$_2$ is A, G, or P;
X$_3$ is D, T, or G; and
X$_4$ is H, R, or T Aspect 22. The rAAV virion of any one of aspects 1-12, wherein the heterologous peptide is a peptide of Formula VI: LQX$_1$X$_2$X$_3$RX$_4$X$_5$X$_6$X$_7$X$_8$X$_9$VNX$_{10}$Q (SEQ ID NO: 141), where
X$_1$ is K or R;
X$_2$ is N, G, or A;
X$_3$ is A, V, N, or D;
X$_4$ is P, I, or Q;
X$_5$ is A, P, or V;
X$_6$ is S, T, or G;
X$_7$ is T or V;
X$_8$ is E, L, A, or V;
X$_9$ is S, E, D, or V; and
X$_{10}$ is F, G, T, or C.

Aspect 23. The rAAV virion of any one of aspects 1-12, wherein the heterologous peptide comprises: (17) LQKNARPASTESVNFQ (SEQ ID NO: 28); (18) LQRGVRIPSVLEVNGQ (SEQ ID NO: 29); (19) LQRGNRPVTTADVNTQ (SEQ ID NO: 30); or (20) LQKADRQPGVVVVNCQ (SEQ ID NO: 31).

Aspect 24. A pharmaceutical composition comprising:
a) a recombinant adeno-associated virus virion of any one of aspects 1-23; and
b) a pharmaceutically acceptable excipient.

Aspect 25. A method of delivering a gene product to a retinal cell in an individual, the method comprising administering to the individual a recombinant adeno-associated virus (rAAV) virion according any one of aspects 1-23 or the composition of aspect 24.

Aspect 26. The method of aspect 25, wherein the gene product is a polypeptide.

Aspect 27. The method of aspect 25, wherein the gene product is a short interfering RNA or an aptamer.

Aspect 28. The method of aspect 26, wherein the polypeptide is a neuroprotective factor, an anti-angiogenic polypeptide, an anti-apoptotic factor, or a polypeptide that enhances function of a retinal cell.

Aspect 29. The method of aspect 26, wherein the polypeptide is glial derived neurotrophic factor, fibroblast growth factor 2, neurturin, ciliary neurotrophic factor, nerve growth factor, brain derived neurotrophic factor, epidermal growth factor, rhodopsin, X-linked inhibitor of apoptosis, retinoschisin, RPE65, retinitis pigmentosa GTPase-interacting protein-1, peripherin, peripherin-2, a rhodopsin, RdCVF, retinitis pigmentosa GTPase regulator (RPGR), or Sonic hedgehog.

Aspect 30. The method of aspect 26, wherein the polypeptide is an RNA-guided endonuclease.

Aspect 31. A method of treating an ocular disease, the method comprising administering to an individual in need thereof an effective amount of a recombinant adeno-associated virus (rAAV) virion according to any one of aspects 1-23 or the composition of aspect 24.

Aspect 32. The method of aspect 31, wherein said administering is by intraocular injection.

Aspect 33. The method of aspect 31, wherein said administering is by intravitreal injection or by suprachoroidal injection.

Aspect 34. The method of any one of aspects 31-33, wherein the ocular disease is glaucoma, retinitis pigmentosa, macular degeneration, retinoschisis, Leber's Congenital Amaurosis, diabetic retinopathy, achromotopsia, or color blindness.

Aspect 35. An isolated nucleic acid comprising a nucleotide sequence that encodes a variant adeno-associated virus (AAV) capsid protein, wherein the variant AAV capsid protein comprises an insertion of from about 5 amino acids to about 20 amino acids in the capsid protein GH loop relative to a corresponding parental AAV capsid protein, and wherein the variant capsid protein, when present in an AAV virion, provides for increased infectivity of the AAV virion of a retinal cell, and wherein the amino acid insertion is in the GH loop of a native AAV capsid, wherein the insertion is a peptide of any one of Formulas I-VI.

Aspect 36. The isolated nucleic acid of aspect 35, wherein the insertion site is between amino acids 587 and 588 of AAV2, between amino acids 585 and 598 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

Aspect 37. An isolated, genetically modified host cell comprising the nucleic acid of aspect 35 or aspect 36.

Aspect 38. A variant adeno-associated virus (AAV) capsid protein, wherein the variant AAV capsid protein comprises an insertion of from about 5 amino acids to about 20 amino acids wherein the amino acid insertion is in the GH loop of a native AAV capsid, wherein the insertion is a peptide of any one of Formulas I-VI.

Aspect 39. A recombinant adeno-associated virus (rAAV) virion comprising:
  a) a variant AAV capsid protein, wherein the variant AAV capsid protein comprises an insertion of a heterologous peptide of Formula VI, and wherein the variant capsid protein confers increased infectivity of a retinal cell compared to the infectivity of the retinal cell by a control AAV virion comprising the corresponding parental AAV capsid protein; and
  b) a heterologous nucleic acid comprising a nucleotide sequence encoding a heterologous gene product.

Aspect 40. The rAAV virion of aspect 39, wherein the rAAV virion exhibits at least 5-fold increased infectivity of a retinal cell compared to the infectivity of the retinal cell by a control AAV virion comprising the corresponding parental AAV capsid protein.

Aspect 41. The rAAV virion of aspect 39, wherein the rAAV virion exhibits at least 10-fold increased infectivity of a retinal cell compared to the infectivity of the retinal cell by an AAV virion comprising the corresponding parental AAV capsid protein.

Aspect 42. The rAAV virion of any one of aspects 39-41, wherein the insertion of the heterologous peptide replaces a contiguous stretch of from 5 amino acids to 20 amino acids of the parental AAV capsid protein.

Aspect 43. The rAAV virion of any one of aspects 39-42, wherein the insertion site is between amino acids corresponding to amino acids 570 and 611 of VP1 of AAV2, or the corresponding position in the capsid protein of another AAV serotype.

Aspect 44. The rAAV virion of aspect 43, wherein the insertion site is located between amino acids corresponding to amino acids 587 and 588 of VP1 of AAV2, or the corresponding position in the capsid protein of another AAV serotype; or wherein the insertion site is located between amino acids corresponding to amino acids 585 and 598 of VP1 of AAV2, or the corresponding position in the capsid protein of another AAV serotype.

Aspect 45. The rAAV virion of any one of aspects 39-44, wherein gene product is an interfering RNA.

Aspect 46. The rAAV virion of any one of aspects 39-44, wherein gene product is an aptamer.

Aspect 47. The rAAV virion of any one of aspects 39-44, wherein the gene product is a polypeptide.

Aspect 48. The rAAV virion of aspect 47, wherein the polypeptide is a neuroprotective polypeptide, an anti-angiogenic polypeptide, or a polypeptide that enhances function of a retinal cell.

Aspect 49. The rAAV virion of aspect 47, wherein the polypeptide is an RNA-guided endonuclease selected from a type II CRISPR/Cas polypeptide, a type V CRISPR/Cas polypeptide, and a type VI CRISPR/Cas polypeptide.

Aspect 50. The rAAV virion of aspect 49, wherein the RNA-guided endonuclease is an enzymatically inactive type II CRISPR/Cas polypeptide.

Aspect 51. The rAAV virion of one of aspects 39-44, wherein the gene product is an RNA-guided endonuclease and a guide RNA.

Aspect 52. The rAAV virion of any one of aspects 39-51, wherein the heterologous peptide comprises: (17) LQKNARPASTESVNFQ (SEQ ID NO: 28); (18) LQRGVRIPSVLEVNGQ (SEQ ID NO: 29); (19) LQRGNRPVTTADVNTQ (SEQ ID NO: 30); or (20) LQKADRQPGVVVVNCQ (SEQ ID NO: 31).

Aspect 53. A pharmaceutical composition comprising:
  a) a recombinant adeno-associated virus virion of any one of aspects 39-52; and
  b) a pharmaceutically acceptable excipient.

Aspect 54. A method of delivering a gene product to a retinal cell in an individual, the method comprising administering to the individual a recombinant adeno-associated virus (rAAV) virion according any one of aspects 39-52 or the composition of aspect 53.

Aspect 55. The method of aspect 54, wherein the gene product is a polypeptide.

Aspect 56. The method of aspect 54, wherein the gene product is a short interfering RNA or an aptamer.

Aspect 57. The method of aspect 55, wherein the polypeptide is a neuroprotective factor, an anti-angiogenic polypeptide, an anti-apoptotic factor, or a polypeptide that enhances function of a retinal cell.

Aspect 58. The method of aspect 57, wherein the polypeptide is glial derived neurotrophic factor, fibroblast growth factor 2, neurturin, ciliary neurotrophic factor, nerve growth factor, brain derived neurotrophic factor, epidermal growth factor, rhodopsin, X-linked inhibitor of apoptosis, retinoschisin, RPE65, retinitis pigmentosa GTPase-interacting protein-1, peripherin, peripherin-2, a rhodopsin, RdCVF, retinitis pigmentosa GTPase regulator (RPGR), or Sonic hedgehog.

Aspect 59. The method of aspect 55, wherein the polypeptide is an RNA-guided endonuclease.

Aspect 60. A method of treating an ocular disease, the method comprising administering to an individual in need thereof an effective amount of a recombinant adeno-associated virus (rAAV) virion according to any one of aspects 39-52 or the composition of aspect 53.

Aspect 61. The method of aspect 60, wherein said administering is by intraocular injection.

Aspect 62. The method of aspect 60, wherein said administering is by intravitreal injection or by suprachoroidal injection.

Aspect 63. The method of any one of aspects 60-62, wherein the ocular disease is glaucoma, retinitis pigmentosa, macular degeneration, retinoschisis, Leber's Congenital Amaurosis, diabetic retinopathy, achromotopsia, or color blindness.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s);

nt, nucleotide(s); i.m., intramuscular(ly); i.p., intraperitoneal (ly); s.c., subcutaneous(ly); and the like.

Example 1: AAV Virions Comprising Variant AAV Capsids

A number of variants of AAV capsids were derived through a directed evolution approach; AAV virions comprising the variant AAV capsids infect the primate retina, e.g., when administered via intravitreal injection. Primates are an important preclinical model for human retinal disease, with a fovea for high acuity vision, similar to humans.

AAV Packaging

AAV virions comprising variant AAV capsids were identified by screening. Five libraries were used for this screen: 1) a 7mer peptide display library based on AAV2, containing a 7mer peptide insertion at amino acid ~588, and surrounded by a 5' LA linker and a 3'A linker; 2) a 7mer peptide display library based on AAV4, with a 7mer peptide insertion at amino acid ~584, with a 5'TG linker and a 3'GLS linker; 3) a 7mer peptide display library based on AAV5 with a 7mer peptide insertion at amino acid ~575 with 5'TG linker and a 3'GLS linker; 4) a library based on an ancestral AAV sequence (Santiago-Ortiz et al., 2015) and containing a 7mer peptide display library at position amino acid ~591 with a 5'TG linker and a 3'GLS linker; and 5) an AAV2-based library with semi-random mutations at surface exposed position amino acid ~588 (Koerber, Jang, & Schaffer, 2008). Virus was packaged such that each viral genome was encapsidated within the capsid protein shell that that genome encoded, as previously described Koerber et al. (2008) supra; Fowler et al. *Nat Protoc* 9, 2267-2284 (2014). Therefore functional improvements identified through selection can be linked to the genome sequence contained within the viral capsid. Briefly, AAV vectors were produced by triple transient transfection of HEK293T cells, purified via iodixanol density centrifugation, and buffer exchanged into PBS by Amicon filtration. DNase-resistant viral genomic titers were measured by quantitative real time PCR using a BioRad iCycler. From this library, an iterative in vivo screening selection process was used to identify variants with the ability to infect the primate retina from the vitreous (FIG. 1). Primate eyes were injected in each round with ~250 µL of 1×10^13 (1E13)–1×10^14 (1E14) vg/mL titer virus. Three weeks after injection, eyes were enucleated, and retinal punches were taken from central and peripheral regions of the retina (FIG. 1). DNA from various retinal layers was assayed, and the capsid inserts were identified. After each round of injection, capsid sequences were recovered by PCR from harvested cells using primers HindIII_F1 and NotI_R1, AscI_R1, or SpeI_R1, with reverse primers being specific to unique AAV backbones, in order to maintain separation of groups of libraries. PCR amplicons were then digested, and recloned into the backbone. RPE cells were separated from retinal tissue, and tissue was frozen. Retinal tissue was embedded and sectioned on a cryostat to isolate photoreceptors in the outer nuclear layer. DNA was then collected from the isolated photoreceptors or RPE, and cap genes were PCR amplified. Recovered cap genes were used for subsequent AAV packaging.

FIG. 1. Illustration of the directed evolution methodology used to develop primate retinal AAV variants. Peptide display libraries were created, packaged into AAV vectors, and injected into the primate eye via intravitreal injections. Iterative round of selection were used to positively select AAV variants from the pool of vectors. Three rounds of selection were followed by a round of error prone PCR, followed by additional selection rounds.

Deep Sequencing of AAV Libraries from Rounds of Selection

Following 5 rounds of selection, Illumina deep sequencing was used to identify variants that increased over the rounds in relative representation in the library of AAV variants. An increase of representation in the viral library indicates positive selection and ability to infect the primate retina from the vitreous. A ~75-85 base pair region containing the 7mer insertion or Loop Swap mutation site was PCR amplified from harvested DNA. Primers included Illumina adapter sequences containing unique barcodes to allow for multiplexing of amplicons from multiple rounds of selection. PCR amplicons were purified and sequenced with a 100-cycle single-read run on an Illumina HiSeq 2500. Custom Python code was written to translate DNA sequences into amino acid sequences, and to identify and count reads containing unique 7mer insert sequences. Read counts were normalized by the total number of reads in the run. Python and Pandas were used to analyze dynamics of directed evolution and create plots.

Deep Sequencing Analysis

Out of a library of ~$1\times10^7$ (~1E7) variants per library, top variants were selected. Best performing variants were chosen as ones with the greatest fold increase in the final round of selection relative to the initial plasmid library (# reads in final round, normalized to total number of reads in the round/# of reads in library, normalized to total number of reads in the round). A pseudo-count of 1 was added before normalization to each individual variant to allow analysis of variants not appearing in sequencing of the plasmid library. Fowler et al. (2014) supra Amino acid sequences of the peptide insertions are shown in FIG. 2.

The variants generated through this approach enable non-invasive panretinal gene therapy strategies in the primate retina using intravitreal injections. These AAV vectors can be used for gene augmentation therapies for retinal degenerative diseases including retinitis pigmentosa, Leber Congenital Amaurosis, Rod-cone dystrophy, cone dystrophy, achromatopsia, X-linked retinoschisis, CRB1, optogenetic therapies, expression of trophic and survival factors such as GDNF, BDNF, FGF, RdCVF, RdCVFL, XIAP, and expression of blockers of neovascularization such as sFLT. The vectors can also be used to deliver gene editing tools such as CRISPR/Cas9 for gene correction or the creation of additional models of retinal disease.

REFERENCES

Dalkara, D., Byrne, L. C., Klimczak, R. R., Visel, M., Yin, L., Merigan, W. H., et al. (2013). In vivo-directed evolution of a new adeno-associated virus for therapeutic outer retinal gene delivery from the vitreous. *Science Translational Medicine*, 5(189), 189ra76. http://doi.org/10.1126/scitranslmed.3005708

Dalkara, D., Goureau, O., Marazova, K., & Sahel, J.-A. (2016). Let there be light: gene and cell therapy for blindness. *Human Gene Therapy*, hum.2015.147. http://doi.org/10.1089/hum.2015.147

Dalkara, D., Kolstad, K. D., Caporale, N., Visel, M., Klimczak, R. R., Schaffer, D. V., & Flannery, J. G. (2009). Inner limiting membrane barriers to AAV-mediated retinal transduction from the vitreous. *Molecular Therapy: the Journal of the American Society of Gene Therapy*, 17(12), 2096-2102. http://doi.org/10.1038/mt.2009.181

Koerber, J. T., Jang, J.-H., & Schaffer, D. V. (2008). DNA Shuffling of Adeno-associated Virus Yields Functionally Diverse Viral Progeny. *Molecular Therapy: the Journal of the American Society of Gene Therapy*, 16(10), 1703-1709. http://doi.org/10.1038/mt.2008.167

Maguire, A. M., Simonelli, F., Pierce, E. A., Pugh, E. N., Jr., Mingozzi, F., Bennicelli, J., et al. (2008). Safety and Efficacy of Gene Transfer for Leber's Congenital Amaurosis. *N Engl J Med*, 358(21), 2240-2248. http://doi.org/10.1056/NEJMoa0802315

Nakazawa, T., Matsubara, A., Noda, K., Hisatomi, T., She, H., Skondra, D., et al. (2006). Characterization of cytokine responses to retinal detachment in rats. *Molecular Vision*, 12, 867-878.

Nakazawa, T., Takeda, M., Lewis, G. P., Cho, K.-S., Jiao, J., Wilhelmsson, U., et al. (2007). Attenuated glial reactions and photoreceptor degeneration after retinal detachment in mice deficient in glial fibrillary acidic protein and vimentin. *Investigative Ophthalmology & Visual Science*, 48(6), 2760-2768. http://doi.org/10.1167/iovs.06-1398

Petrs-Silva, H., Dinculescu, A., Li, Q., Min, S.-H., Chiodo, V., Pang, J. J., et al. (2009). High-efficiency transduction of the mouse retina by tyrosine-mutant AAV serotype vectors. *Molecular Therapy: the Journal of the American Society of Gene Therapy*, 17(3), 463-471. http://doi.org/10.1038/mt.2008.269

Santiago-Ortiz, J., Ojala, D. S., Westesson, O., Weinstein, J. R., Wong, S. Y., Steinsapir, A., et al. (2015). AAV ancestral reconstruction library enables selection of broadly infectious viral variants. *Gene Therapy*, 22(12), 934-946. http://doi.org/10.1038/gt.2015.74

Example 2: Methods for Construction and Sequencing of GFP-Barcode Libraries

GFP Barcode Library Construction

Unique 25 bp DNA barcodes were cloned behind an AAV ITR construct containing a self-complementary CAG promoter driving eGFP (CAG-GFP-Barcode-pA). Individual variants were packaged separately with constructs containing different barcodes. Variants were then titer matched and mixed in equal ratios before injection into mice, dogs, and primates.

Deep Sequencing of GFP-Barcode Libraries

Barcodes were PCR amplified directly from DNA or cDNA (created from mRNA using Superscript III reverse transcriptase), which was harvested from dog or primate retinal tissue. Samples were collected from areas across the retina, and from ONL or RPE. Primers amplified a ~50 bp region surrounding the GFP barcode and contained Illumina adapter sequences and secondary barcodes to allow for multiplexing of multiple samples. PCR amplicons were purified and sequenced with a 100-cycle single-read run on a MiSeq. Read counts were normalized by total number of reads in the run. Analysis of barcode abundance was performed using custom code written in Python, followed by creation of plots in Pandas. Best performing variants were selected based on the fold increase in the percent of total library, relative to the injected library (% of total in recovered sample/% of total in injected library). Analysis was performed on n=1 primate.

FIG. 9 provides Table 1; FIG. 10 provides Table 2.

Table 1 provides a ranking of primate-derived variants and controls recovered from photoreceptors following injection of a GFP-Barcode library. Table 2 provides a ranking of primate-derived variants and controls recovered from RPE cells following injection of a GFP-Barcode library. The library contained individual variants packaged with GFP fused to a unique DNA barcode. Polymerase chain reaction (PCR) was used to amplify barcodes from DNA recovered from specific cell types in the retina. "Region" in Tables 1 and 2 indicates the region from which the DNA was recovered. The fold increase of reads of each of the variants was calculated by dividing number of reads for each unique barcode in the recovered cells (corresponding to each unique variant), by the number of reads for each variant in the injected library. This table indicates the average of the fold increase across multiple locations in the retina. Variants were ranked by fold increase of the barcode.

Figure 11:
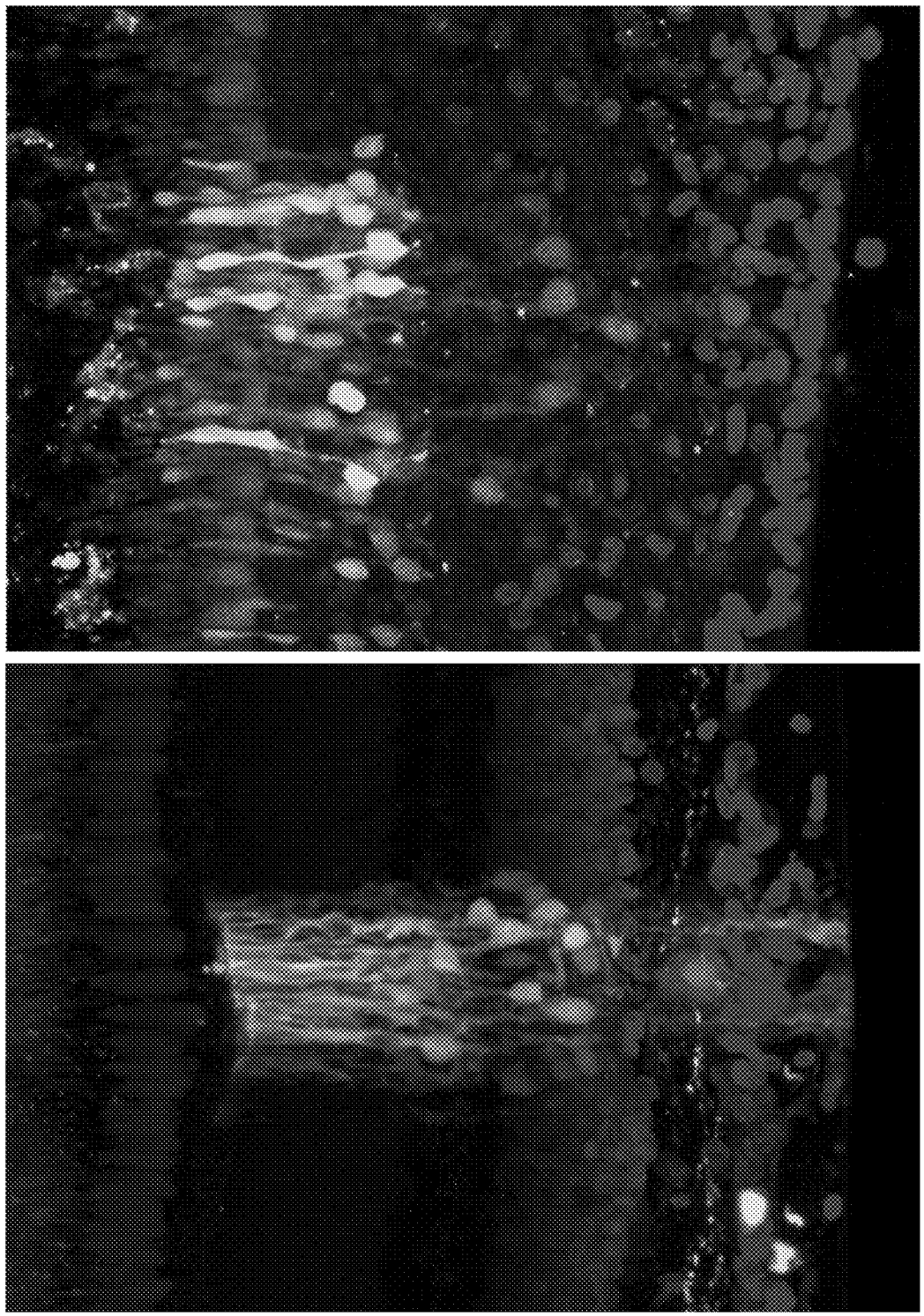
FIG. 11 depicts GFP expression of GFP-barcoded libraries in primate retina.

FIG. 11. GFP expression of GFP-barcoded libraries in primate retina. GFP expression resulting from intravitreal injection of pooled, GFP-barcoded library (which contains all the tested viruses) was located primarily in the outer retina, with a tropism that was directed more toward the outer retina than expression of AAV24YF.

Example 3

Primate Studies

Cynomolgous monkeys between 4-10 years old were used for all studies, and intravitreal injections were made. The monkey used for fluorophore expression received daily subcutaneous injections of cyclosporine at a dose of 6 mg/kg for immune suppression, and adjusted based on blood trough levels to within a 150-200 ng/ml target range. Confocal scanning laser ophthalmoscopic images (Spectralis HRA, Heidelberg Engineering) were obtained from the two retinas at 3 weeks after injection, with autofluorescence settings, which leads to effective tdTomato and GFP visualization. For histology, the monkey was euthanized, both retinas were lightly fixed in 4% paraformaldehyde, and tissue was examined by confocal microscopy. At the conclusion of the experiment, euthanasia was achieved by administering an IV overdose of sodium pentobarbital (75 mg kg−1), as recommended by the Panel on Euthanasia of the American Veterinary Medical Association. Pieces of primate retina were then prepared in 30% sucrose, embedded in OCT media, flash frozen, and sectioned at 20 µm for confocal microscopy imaging of native fluorophore expression. Antibodies for labeling were: anti-GFP (A11122, Thermo, 1:250) anti-vimentin (Dako, 1:1000), peanut agglutinin (PNA) (Molecular Probes, 1:200), and anti-cone arrestin (7G6, 1:50). The procedures were conducted according to the ARVO Statement for the Use of Animals and the guidelines of the Office of Laboratory Animal Care at the University of Rochester.

Results

Directed Evolution of AAV in Primate Retina

In addition to canine, the nonhuman primate is a critical preclinical model for human therapeutic development, as it is most closely related to, and has a retinal anatomy similar to that of humans. In particular, primates are the only large animal model that possesses a fovea, the specialized high acuity area of the retina that is most important for daily activities such as reading, is critical to quality of life, and is lost in numerous retinal degenerations. The species specificity observed in the canine study motivated us to pursue an additional course of directed evolution in primate retina. Nine libraries were packaged and included in the primate screen: EP2, EP5, EP6, EP8, EP9, EP-Ancestral, AAV2-7mer, Ancestral-7mer (Santiago-Ortiz et al. *Gene Ther* 22, 934-946 (2015)) and LoopSwap (Koerber et al. *Mol Ther* 17, 2088-2095 (2009)). Libraries were injected, harvested, and repackaged for 5 sequential rounds of selection, with one round of error prone PCR performed after round 3. AAV cap genes were PCR amplified from ONL, and in parallel from overlying RPE. EP libraries were abandoned at round 3, as no variants from these libraries were recovered from retinal tissue. At round 4, additional libraries (AAV4-7mer and AAV5-7mer) were added to the selection, using a separate backbone that was isolated from other libraries by separate PCR annealing sites and restriction sites.

Figure 12A:
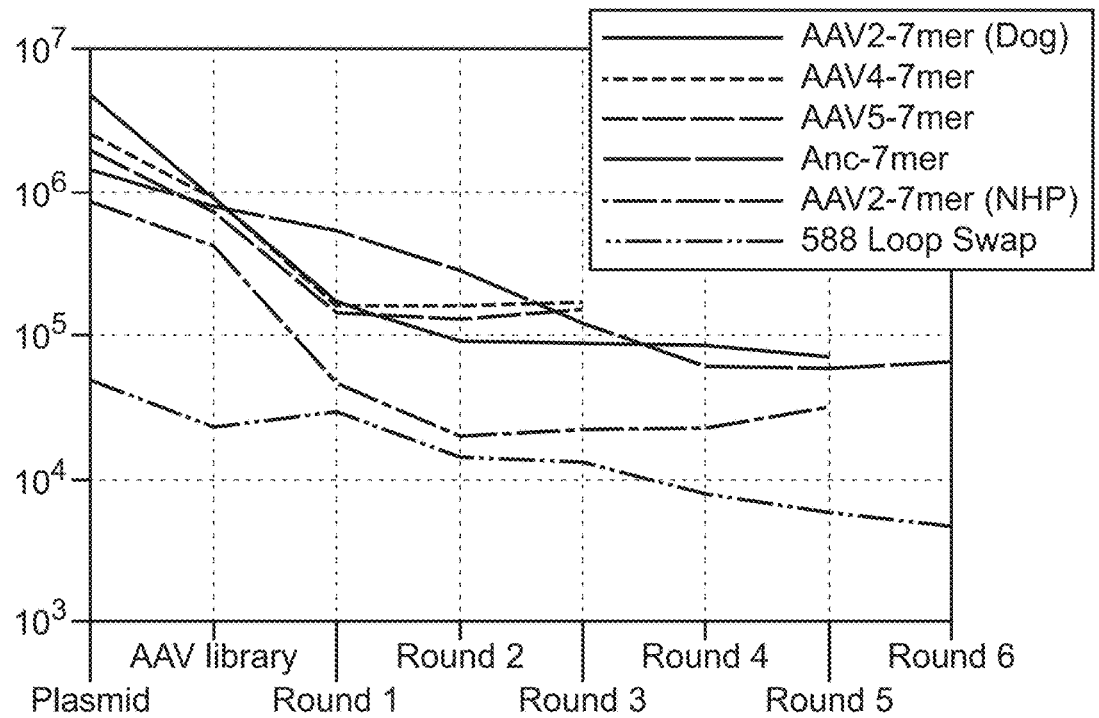
FIG. 12A-12F depict directed evolution of AAV in primate retina. The sequences in FIG. 12F from top to bottom are set forth in SEQ ID NOs:117-135.
Figure 12B:
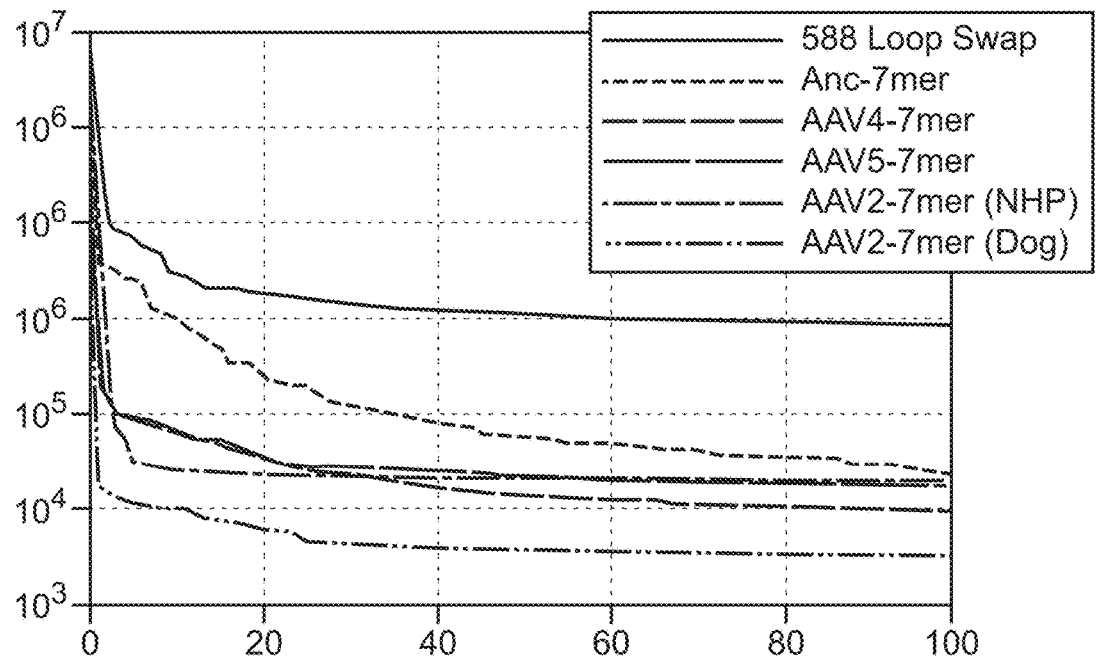
Figure 12C:
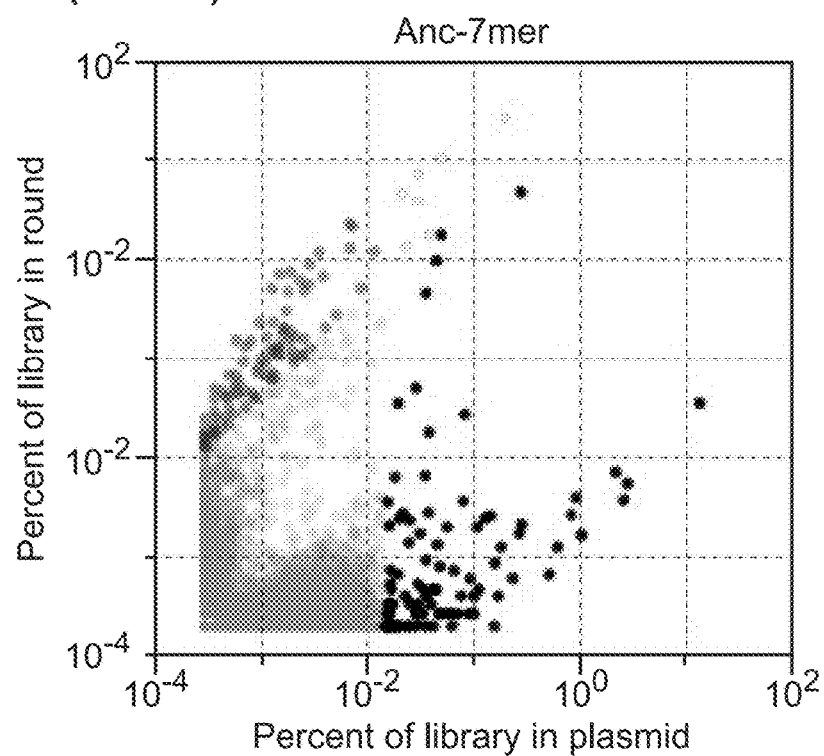

Deep sequencing revealed that, similar to observations from the canine screen, libraries contained ~1E+6-~1E+7 individual variants, which converged to ~1E+4-~1E+5 variants over 6 rounds of selection, a diversity not possible to observe through Sanger sequencing (FIG. 12A). As observed in the canine screen, in each of the libraries analyzed, a small portion of library members were overrepresented in the initial plasmid library (FIG. 12B). Analysis of results from high throughput sequencing over the rounds of selection revealed, for each of the libraries, a subset of variants that increased significantly in their representation during rounds of selection (FIG. 12C).

Secondary Barcoded-GFP Library Screening in Primate Retina

Figure 12D:
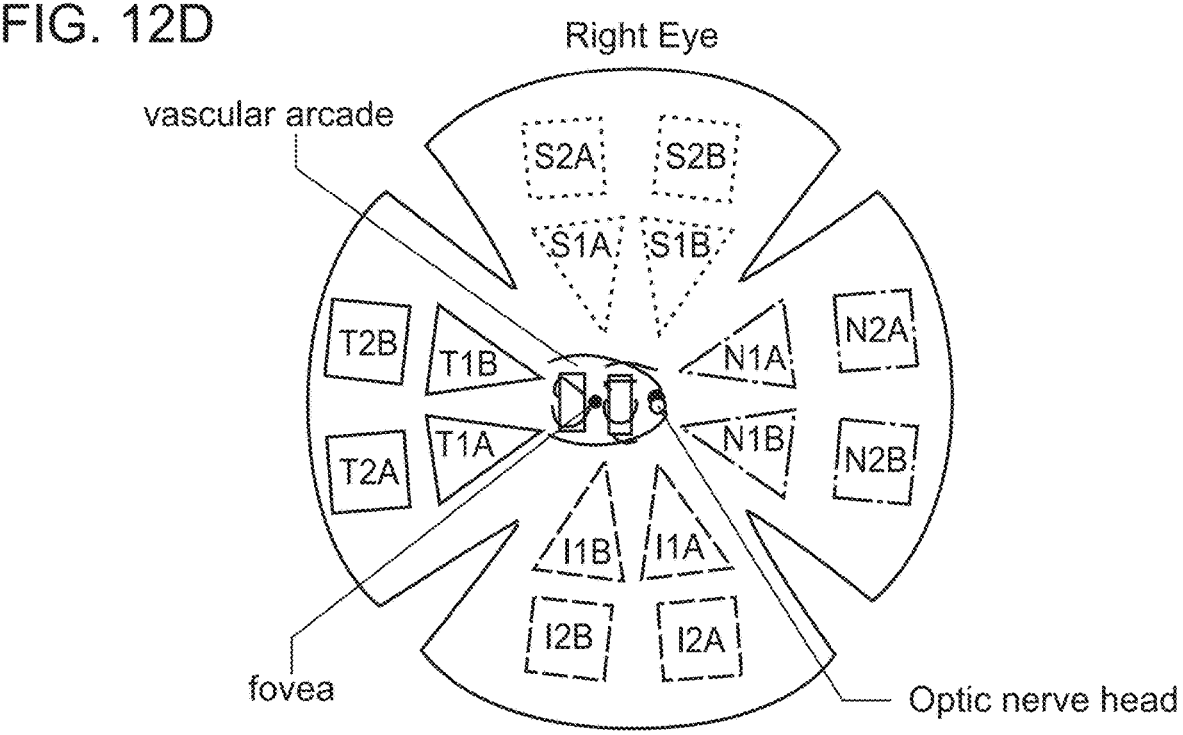
Figures 12E, 12F:
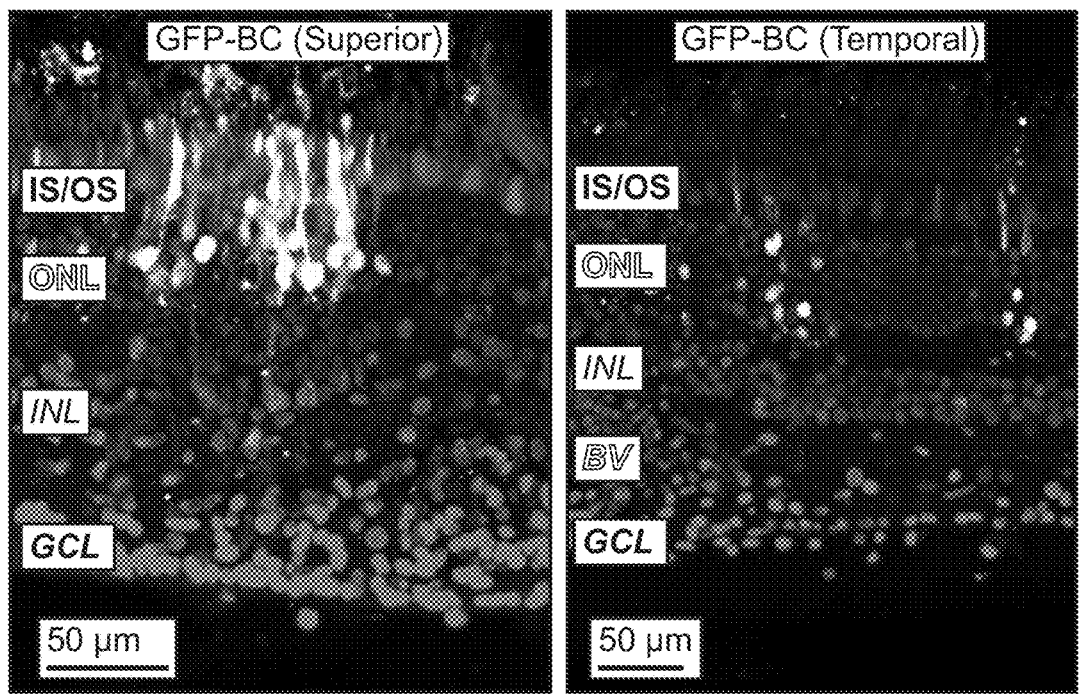

Sixteen variants, from these 5 libraries (FIG. 12C), were selected to be included in a secondary round of selection with GFP-barcoded libraries, along with AAV2, AAV2-4YF+TV, AAV4 and AAV5 as controls. This new library was injected in both eyes of a primate, and 3 weeks after injection, biopsies were collected from locations across the retina (FIG. 12D). GFP expression resulting from injection of the GFP-barcode libraries was primarily found in photoreceptors, as well as some inner retinal cells, a tropism that is shifted from AAV2 or 7m8, which yielded stronger inner retinal expression (FIG. 12E).

FIG. 12A-12F. Directed evolution of AAV in primate retina. (A) Deep sequencing of variant libraries revealed convergence of variants over rounds of selection. (B) In each of the libraries evaluated, a small proportion of variants are overrepresented in the plasmid library. (C) Scatterplots illustrate the behavior of individual variants at the final round of selection for each of the libraries injected in primate retinas. Variants overrepresented in the original library are colored blue. Variants that had the greatest fold increase in representation in the final round of selection are shown in magenta. Variants that were overrepresented in the original library and increased significantly in representation over rounds of selection are colored orange. (D) A map of the primate retina shows the distribution of samples that were collected for rounds of selection and the GFP-barcode library. Color coding of variants is the same as in FIG. 2. (E) GFP expression resulting from the barcoded library revealed that expression was shifted to an outer retinal tropism in selected variants. (F) GFP-barcode library injection results, for primate outer retina. The lists of variants are ordered from best (top) to worst (bottom) performing vectors, along with a value indicating the extent to which the variant competed with other vectors, expressed as: % of total in AAV library/% of total in recovered library.

Validation of the Top-Performing Primate Variants

Quantification of vector performance in outer retina revealed that AAV2-based variants outperformed viruses based on other serotypes. One vector, Loop Swap variant AAV2 588~LQRGVRIPSVLEVNGQ (SEQ ID NO:116), outperformed other variants, though it yielded lower viral titers (~5E+11 vg/mL).

AAV2-LALIQDSMRA (SEQ ID NO:117; designated NHP #9), the second ranking variant from the GFP-barcode screen, which packaged at high titers (~5E+13 vg/mL), was therefore selected for a first round of validation studies focusing on ganglion cells of the inner retina and cones of the outer retina. Cone photoreceptors are involved in adult macular degeneration (AMD), the most common cause of blindness in developed countries that are predicted to affect 288 million people worldwide by the year 2040, and are therefore a primary target for retinal gene therapy. NHP #9 was packaged with an SNCG promoter driving tdTomato in RGCs and the pR1.7 promoter driving expression of GFP in cones. Vectors encoding both these constructs were mixed in equal ratios (~1.5E+12 vg/construct/eye, and injected intravitreally in a cynomolgus monkey. A previously described variant, 7m8 (Dalkara et al. (2013) supra), packaged with equal titers of the same constructs was injected into the vitreous of the contralateral eye. Expression of tdTomato reporter in RGC's was lower in NHP #9-injected eyes compared to 7m8, which infected ganglion cells across the expanse of the retina efficiently; however, expression in foveal cones was greatly increased relative to 7m8, indicating a shift in tropism away from the inner retina towards photoreceptors in the outer retina. qRT-PCR, performed using the ddCT method, revealed an 11.71 (10.37-13.22) fold increase of GFP expression in foveal cones relative to 7m8. Counting of labeled cells, performed with Imaris software on images collected from flatmounted retinas, also confirmed a substantial decrease in numbers of transduced ganglion cells and an increase in the number of cones targeted with NHP #9.

Next, the top-ranking variant from the GFP barcode screen, Loopswap variant ~588-LQRGVRIPSVLEVNGQ (SEQ ID NO:118; designated NHP #26) was also tested for validation, although low numbers of viral particles were produced. ~5E+10 particles of NHP #26-scCAG-eGFP were injected intravitreally into one eye of a cynomolgous monkey. Although the number of particles injected was low, efficient expression of GFP was observed in the fovea and across the retina (FIG. 13G). In contrast to the foveal-spot-and-ring pattern of expression that was observed with 7m8, NHP #9 (FIG. 13A), and other naturally occurring serotypes, fundus imaging of NHP #26 resulted in a disc of GFP expression centered on the foveola (FIG. 13G). Confocal imaging of the flatmounted retina confirmed this disc pattern of expression around the fovea (FIG. 13H), with very few GFP positive ganglion cell axons. Punctate regions of GFP expression were often strongest around retinal blood vessels (FIG. 13I), and were located across the expanse of the retina. Imaging of cryostat sections taken from the retina confirmed that there was little GFP expression in ganglion cells, as indicated by the lack of GFP+ ganglion cell axons, while high levels of GFP expression were found in Müller cells, additional cells in the inner nuclear layer, foveal cones and rods across the retina (FIG. 13J-13Q).

Figure 13A:
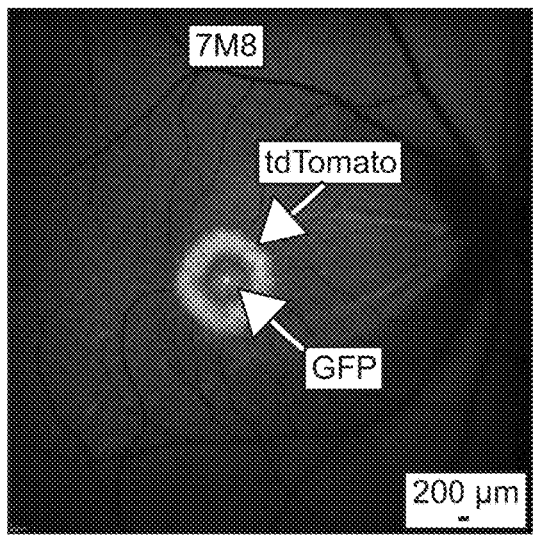
FIG. 13A-13Q depict validation of evolved AAV variants in primate retina.
Figure 13B:
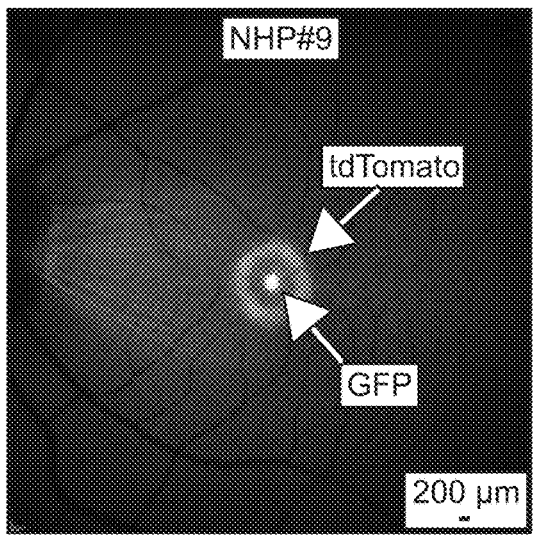
Figure 13C:
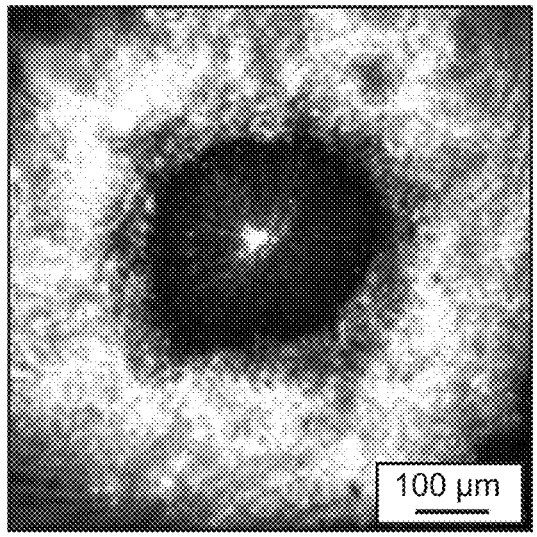
Figure 13D:
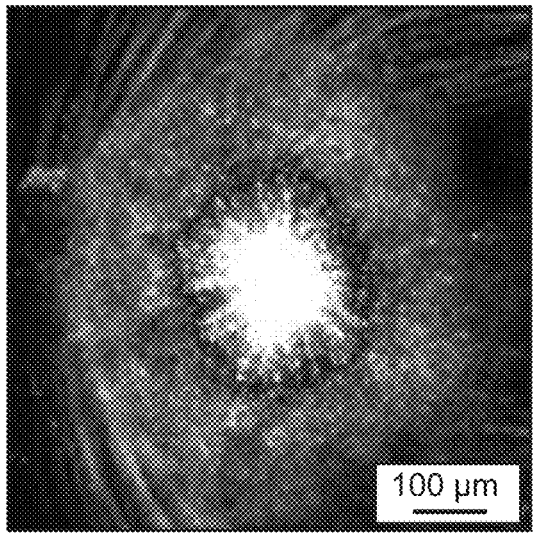
Figure 13E:
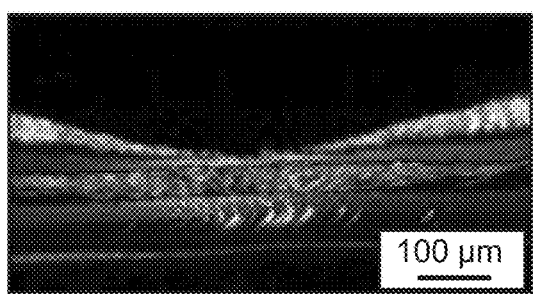
Figure 13F:
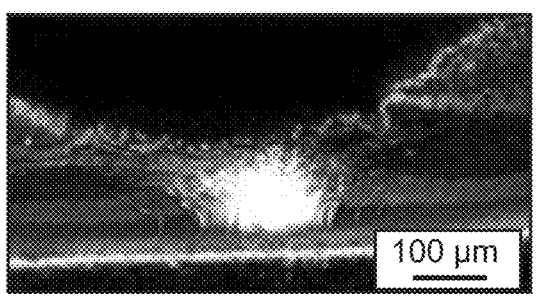
Figure 13G:
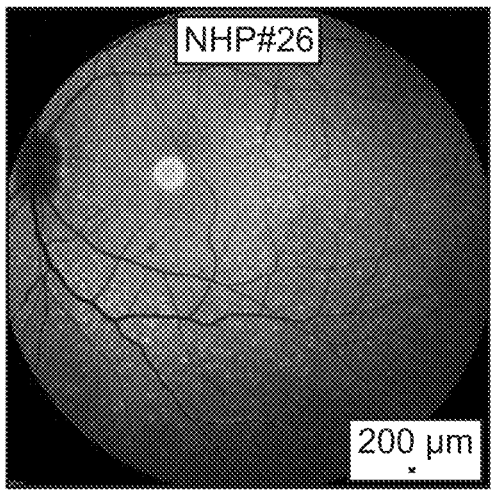
Figure 13H:
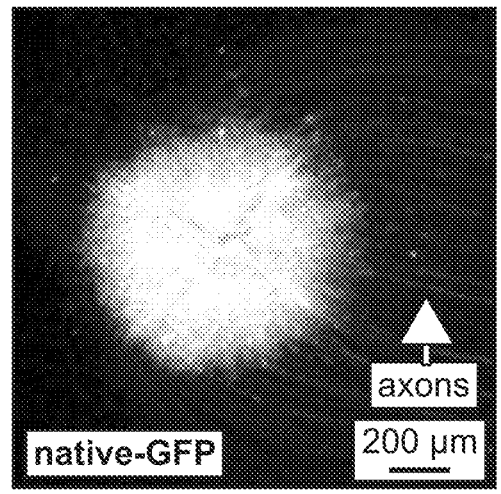
Figure 13I:
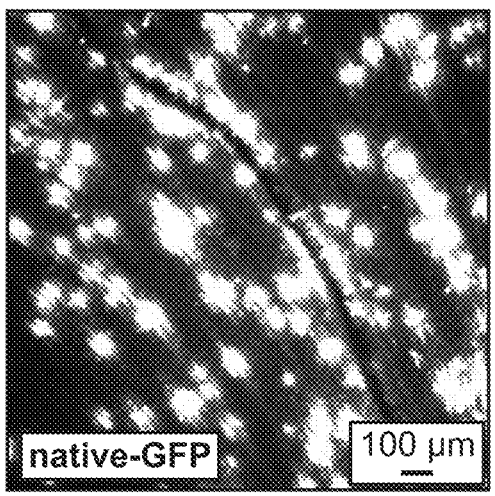
Figure 13J:
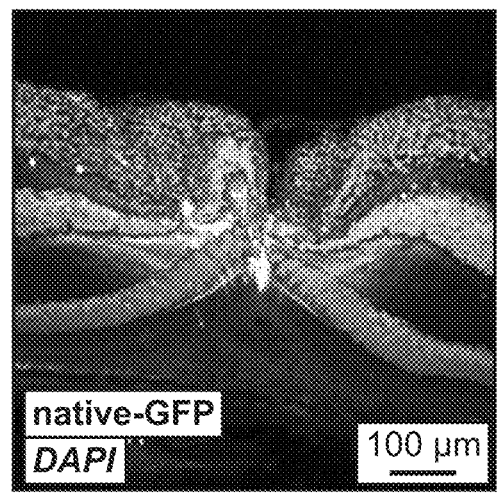
Figure 13K:
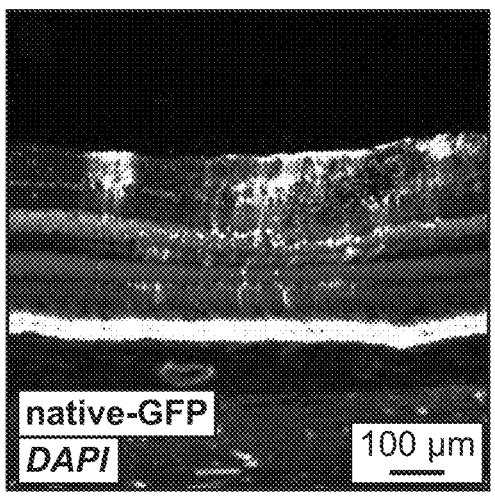
Figure 13L:
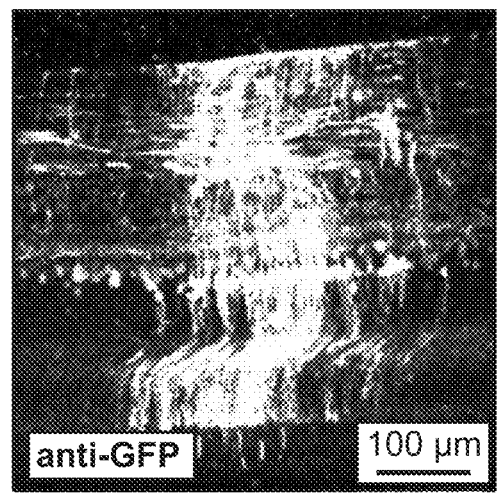
Figure 13M:
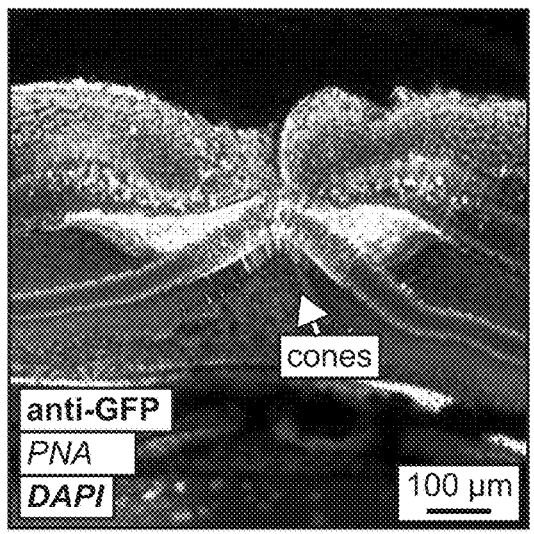
Figure 13N:
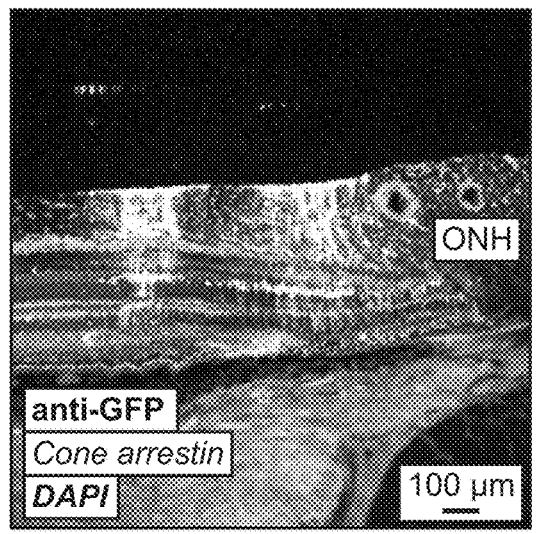
Figure 13O:
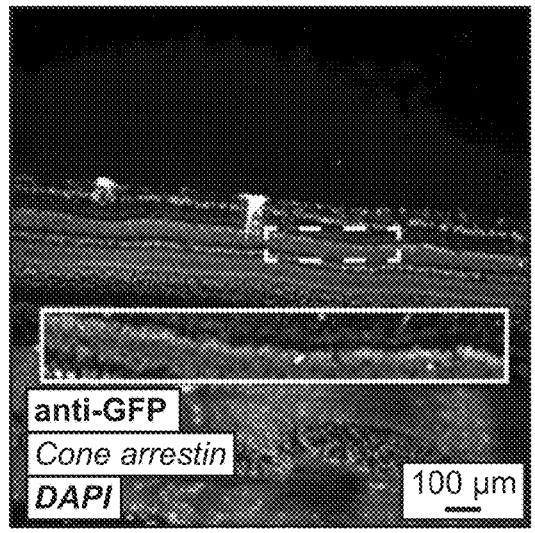

FIG. 13A-13Q. Validation of evolved AAV variants in primate retina. (A-F) Co-injection of ~1.5E+12 particles of SCNG-tdTomato and ~1.5E+12 pR1.7-eGFP packaged in 7m8 and variant NHP #9 in primate retina. Intravitreal injection of 7m8 (A,C,E) resulted in robust tdTomato expression in ganglion cells and expression of GFP in foveal cones. In contrast, injection of equal number of particles of NHP #9 resulted in reduced ganglion cell expression, and increased GFP expression in cones relative to 7m8 (B,D,F). (G) Fundus imaging in a primate eye following injection of 5E+10 particles of NHP #26-scCAG-GFP resulted in a disc of GFP expression centered on the fovea, and a punctate pattern of GFP expression across the retina. (H) Confocal imaging of native GFP expression in the flatmounted fovea. (I) Confocal imaging of native GFP expression in the area outside of the vascular arcade. (J) Confocal imaging of native GFP expression in a cryostat section through the fovea. (K) Native GFP expression in inferior retina, outside the vascular arcade, shows little GFP expression in ganglion cells, but high levels of expression in Müller cells and in photoreceptors in outer retina. Autofluorescence was also observed in RPE. (L) Anti-GFP labeling in a cryostat section revealed GFP expression in photoreceptors, evident by their outer segments, Müller cells, evident by their retina-spanning processes, as well as cells in the inner nuclear layer with horizontal processes that are likely interneurons. (M) Anti-GFP labeling in a foveal section reveals additional transfected cones, Müller glia and interneurons. (N) Co-labeling with anti-cone arrestin and anti-GFP reveals GFP expression in rod photoreceptors, as well as cells in the inner nuclear layer, in a section taken next to the optic nerve head. (O) Co-labeling with anti-cone arrestin and anti-GFP antibodies in an area of low expression reveals GFP expression in inner nuclear layer cells. (P,Q) Montages of confocal images from cryostat sections collected outside the vascular arcade show efficient expression of GFP in the inner nuclear layer and outer retina.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant adeno-associated virus (rAAV) comprising:
   a) a variant AAV capsid protein, wherein the variant AAV capsid protein comprises an insertion of a heterologous peptide between amino acids 570 and 611 of VP1 of AAV2 according to SEQ ID NO:1, wherein the heterologous peptide comprises the sequence of LQRGVRIPSVLEVNGQ (SEQ ID NO: 29) or LALIQDSMRA (SEQ ID NO: 35); and
   b) a heterologous nucleic acid comprising a nucleotide sequence encoding a heterologous gene product.

2. The rAAV of claim 1, wherein the variant capsid protein confers increased infectivity of a retinal cell compared to the infectivity of the retinal cell by a control AAV comprising the corresponding parental AAV capsid protein.

3. The rAAV of claim 1, wherein the heterologous peptide comprises the sequence of LALIQDSMRA (SEQ ID NO: 35).

4. The rAAV of claim 1, wherein the heterologous peptide comprises the sequence of LQRGVRIPSVLEVNGQ (SEQ ID NO: 29).

5. The rAAV of claim 1, wherein the insertion site is located between amino acids corresponding to amino acids 587 and 588 of the VP1 of AAV2 according to SEQ ID NO:1.

6. The rAAV of claim 1, wherein the insertion site is located between amino acids corresponding to amino acids 585 and 598 of the VP1 of AAV2 according to SEQ ID NO:1.

7. The rAAV of claim 1, wherein gene product is a polypeptide, an interfering RNA or an aptamer.

8. The rAAV of claim 7, wherein the polypeptide is a neuroprotective polypeptide or an anti-angiogenic polypeptide.

9. The rAAV of claim 7, wherein the polypeptide is an RNA-guided endonuclease selected from a type II CRISPR/Cas polypeptide, a type V CRISPR/Cas polypeptide, and a type VI CRISPR/Cas polypeptide.

10. The rAAV of claim 9, wherein the RNA-guided endonuclease is an enzymatically inactive type II CRISPR/Cas polypeptide.

11. The rAAV of claim 1, wherein the gene product is an RNA-guided endonuclease and a guide RNA.

12. A pharmaceutical composition comprising:
a) the rAAV according to claim 1; and
b) a pharmaceutically acceptable excipient.

13. The pharmaceutical composition of claim 12, comprising from $10^6$ to $10^{15}$ rAAV.

14. An isolated nucleic acid comprising a nucleotide sequence that encodes a variant adeno-associated virus (AAV) capsid protein comprising an insertion of a heterologous peptide between amino acids 570 and 611 of VP1 of AAV2 according to SEQ ID NO:1, wherein the heterologous peptide comprises the sequence of LQRGVRIPSVLEVNGQ (SEQ ID NO: 29) or LALIQDSMRA (SEQ ID NO: 35).

15. An isolated host cell comprising the nucleic acid of claim 14.

16. A method of delivering a gene product to a retinal cell in an individual, the method comprising administering to the individual the recombinant adeno-associated virus (rAAV) of claim 1.

* * * * *

```
                           SEQUENCE LISTING

Sequence total quantity: 159
SEQ ID NO: 1              moltype = AA   length = 733
FEATURE                   Location/Qualifiers
source                    1..733
                          mol_type = protein
                          organism = Adeno-associated virus 2
SEQUENCE: 1
MAADGYLPDW LEDTLSEGIR QWWKLKPGPP PPKPAERHKD DSRGLVLPGY KYLGPFNGLD   60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTR                                                    733

SEQ ID NO: 2              moltype = AA   length = 10
FEATURE                   Location/Qualifiers
source                    1..10
                          mol_type = protein
                          organism = synthetic construct
SEQUENCE: 2
LANQEHVKNA                                                         10

SEQ ID NO: 3              moltype = DNA  length = 20
FEATURE                   Location/Qualifiers
source                    1..20
                          mol_type = other DNA
                          organism = synthetic construct
SEQUENCE: 3
cgcaacagga agcaacaccg                                              20

SEQ ID NO: 4              moltype = AA   length = 10
FEATURE                   Location/Qualifiers
source                    1..10
                          mol_type = protein
                          organism = synthetic construct
SEQUENCE: 4
LTHQDTTKNA                                                         10

SEQ ID NO: 5              moltype = AA   length = 10
FEATURE                   Location/Qualifiers
source                    1..10
                          mol_type = protein
                          organism = synthetic construct
SEQUENCE: 5
QAHQDTTKNA                                                         10

SEQ ID NO: 6              moltype = AA   length = 12
FEATURE                   Location/Qualifiers
source                    1..12
                          mol_type = protein
```

```
                              -continued organism = synthetic construct
SEQUENCE: 6
TGVMRSTNSG LN                                                            12

SEQ ID NO: 7           moltype = AA  length = 12
FEATURE                Location/Qualifiers
source                 1..12
                       mol_type = protein
                       organism = synthetic construct
SEQUENCE: 7
TGEVDLAGGG LS                                                            12

SEQ ID NO: 8           moltype = AA  length = 12
FEATURE                Location/Qualifiers
source                 1..12
                       mol_type = protein
                       organism = synthetic construct
SEQUENCE: 8
TSPYGSSDG LS                                                             12

SEQ ID NO: 9           moltype = AA  length = 12
FEATURE                Location/Qualifiers
source                 1..12
                       mol_type = protein
                       organism = synthetic construct
SEQUENCE: 9
TGGHDSSLDG LS                                                            12

SEQ ID NO: 10          moltype = AA  length = 224
FEATURE                Location/Qualifiers
source                 1..224
                       mol_type = protein
                       organism = Homo sapiens
SEQUENCE: 10
MSRKIEGFLL LLLFGYEATL GLSSTEDEGE DPWYQKACKC DCQGGPNALW SAGATSLDCI         60
PECPYHKPLG FESGEVTPDQ ITCSNPEQYV GWYSSWTANK ARLNSQGFGC AWLSKFQDSS        120
QWLQIDLKEI KVISGILTQG RCDIDEWMTK YSVQYRTDER LNWIYYKDQT GNNRVFYGNS        180
DRTSTVQNLL RPPIISRFIR LIPLGWHVRI AIRMELLECV SKCA                         224

SEQ ID NO: 11          moltype = AA  length = 247
FEATURE                Location/Qualifiers
source                 1..247
                       mol_type = protein
                       organism = Homo sapiens
SEQUENCE: 11
MTILFLTMVI SYFGCMKAAP MKEANIRGQG GLAYPGVRTH GTLESVNGPK AGSRGLTSLA         60
DTFEHVIEEL LDEDHKVRPN EENNKDADLY TSRVMLSSQV PLEPPLLFLL EEYKNYLDAA        120
NMSMMVLRHS DPARRGELSV CDSISEWVTA ADKKTAVDMS GGTVTVLEKV PVSKGQLKQY        180
FYETKCNPMG YTKEGCRGID KRHWNSQCRT TQSYVRALTM DSKKRIGWRF IRIDTSCVCT        240
LTIKRGR                                                                  247

SEQ ID NO: 12          moltype = AA  length = 533
FEATURE                Location/Qualifiers
source                 1..533
                       mol_type = protein
                       organism = Homo sapiens
SEQUENCE: 12
MSIQVEHPAG GYKKLFETVE ELSSPLTAHV TGRIPLWLTG SLLRCGPGLF EVGSEPFYHL         60
FDGQALLHKF DFKEGHVIYH RRFIRTDAYV RAMTEKRIVI TEFGTCAFPD PCKNIFSRFF        120
SYFRGVEVTD NALVNVYPVG EDYYACTETN FITKINPETL ETIKQVDLCN YVSVNGATAH        180
PHIENDGTVY NIGNCFGKNF SIAYNIVKIP PLQADKEDPI SKSEIVVQFP CSDRFKPSYV        240
HSFGLTPNYI VFVETPVKIN LFKFLSSWSL WGANYMDCFE SNETMGVWLH IADKKRKKYL        300
NNKYRTSPFN LFHHINTYED NGFLIVDLCC WKGFEFVYNY LYLANLRENW EEVKKNARKA        360
PQPEVRRYVL PLNIDKADTG KNLVTLPNTT ATAILCSDET IWLEPEVLFS GPRQAFEFPQ        420
INYQKYCGKP YTYAYGLGLN HFVPDRLCKL NVKTKETWVW QEPDSYPSEP IFVSHPDALE        480
EDDGVVLSVV VSPGAGQKPA YLLILNAKDL SEVARAEVEI NIPVTFHGLF KKS               533

SEQ ID NO: 13          moltype = AA  length = 346
FEATURE                Location/Qualifiers
source                 1..346
                       mol_type = protein
                       organism = Homo sapiens
SEQUENCE: 13
MALLKVKFDQ KKRVKLAQGL WLMNWFSVLA GIIIFSLGLF LKIELRKRSD VMNNSESHFV         60
PNSLIGMGVL SCVFNSLAGK ICYDALDPAK YARWKPWLKP YLAICVLFNI ILFLVALCCF        120
LLRGSLENTL GQGLKNGMKY YRDTDTPGRC FMKKTIDMLQ IEFKCCGNNG FRDWFEIQWI        180
SNRYLDFSSK EVKDRIKSNV DGRYLVDGVP FSCCNPSSPR PCIQYQITNN SAHYSYDHQT        240
EELNLWVRGC RAALLSYYSS LMNSMGVVTL LIWLFEVTIT IGLRYLQTSL DGVSNPEESE        300
SESQGWLLER SVPETWKAFL ESVKKLGKGN QVEAEGADAG QAPEAG                       346
```

```
SEQ ID NO: 14           moltype = AA  length = 470
FEATURE                 Location/Qualifiers
source                  1..470
                        mol_type = protein
                        organism = Homo sapiens
SEQUENCE: 14
MSHHPSGLRA GFSSTSYRRT FGPPPSLSPG AFSYSSSSRF SSSRLLGSAS PSSSVRLGSF    60
RSPRAGAGAL LRLPSERLDF SMAEALNQEF LATRSNEKQE LQELNDRFAN FIEKVRFLEQ   120
QNAALRGELS QARGQEPARA DQLCQQELRE LRRELELLGR ERDRVQVERD GLAEDLAALK   180
QRLEEETRKR EDAEHNLVLF RKDVDDATLS RLELERKIES LMDEIEFLKK LHEEELRDLQ   240
VSVESQQVQQ VEVEATVKPE LTAALRDIRA QYESIAAKNL QEAEEWYKSK YADLSDAANR   300
NHEALRQAKQ EMNESRRQIQ SLTCEVDGLR GTNEALLRQL RELEEQFALE AGGYQAGAAR   360
LEEELRQLKE EMARHLREYQ ELLNVKMALD IEIATYRKLL EGEESRISVP VHSFASLNIK   420
TTVPEVEPPQ DSHSRKTVLI KTIETRNGEV VTESQKEQRS ELDKSSAHSY              470

SEQ ID NO: 15           moltype = AA  length = 1286
FEATURE                 Location/Qualifiers
source                  1..1286
                        mol_type = protein
                        organism = Homo sapiens
SEQUENCE: 15
MSHLVDPTSG DLPVRDIDAI PLVLPASKGK NMKTQPPLSR MNREELEDSF FRLREDHMLV    60
KELSWKQQDE IKRLRTTLLR LTAAGRDLRV AEEAAPLSET ARRGQKAGWR QRLSMHQRPQ   120
MHRLQGHFHC VGPASPRRAQ PRVQVGHRQL HTAGAPVPEK PKRGPRDRLS YTAPPSFKEH   180
ATNENRGEVA SKPSELVSGS NSIISFSSVI SMAKPIGLCM PNSAHIMASN TMQVEEPPKS   240
PEKMWPKDEN FEQRSSLECA QKAAELRASI KEKVELIRLK KLLHERNASL VMTKAQLTEV   300
QEAYETLLQK NQGILSAAHE ALLKQVNELR AELKEESKKA VSLKSQLEDV SILQMTLKEF   360
QERVEDLEKE RKLLNDNYDK LLESMLDSSD SSSQPHWSNE LIAEQLQQQV SQLQDQLDAE   420
LEDKRKVLLE LSREKAQNED LKLEVTNILQ KHKQEVELLQ NAATISQPPD RQSEPATHPA   480
VLQENTQIEP SEPKNQEEKK LSQVLNELQV SHAETTLELE KTRDMLILQR KINVCYQEEL   540
EAMMTKADND NRDHKEKLER LTRLLDLKNN RIKQLEGILR SHDLPTSEQL KDVAYGTRPL   600
SLCLETLPAH GDEDKVDISL LHQGENLFEL HIHQAFLTSA ALAQAGDTQP TTFCTYSFYD   660
FETHCTPLSV GPQPLYDFTS QYVMETDSLF LHYLQEASAR LDIHQAMASE HSTLAAGWIC   720
FDRVLETVEK VHGLATLIGA GGEEFGVLEY WMRLRFPIKP SLQACNKRKK AQVYLSTDVL   780
GGRKAQEEEF RSESWEPQNE LWIEITKCCG LRSRWLGTQP SPYAVYRFFT FSDHDTAIIP   840
ASNNPYFRDQ ARFPVLVTSD LDHYLRREAL SIHVFDDEDL EPGSYLGRAR VPLLPLAKNE   900
SIKGDFNLTD PAEKPNGSIQ VQLDWKFPYI PPESFLKPEA QTKGKDTKDS SKISSEEEKA   960
SFPSQDQMAS PEVPIEAGQY RSKRKPPHGG ERKEKEHQVV SYSRRKHGKR IGVQGKNRME  1020
YLSLNILNGN TPEQVNYTEW KFSETNSFIG DGFKNQHEEE EMTLSHSALK QKEPLHPVND  1080
KESSEQGSEV SEAQTTDSDD VIVPPMSQKY PKADSEKMCI EIVSLAFYPE AEVMSDENIK  1140
QVYVEYKFYD LPLSETETPV SLRKPRAGEE IHFHFSKVID LDPQEQQGRR RFLFDMLNGQ  1200
DPDQGHLKFT VVSDPLDEEK KECEEVGYAY LQLWQILESG RDILEQELDI VSPEDLATPI  1260
GRLKVSLQAA AVLHAIYKEM TEDLFS                                      1286

SEQ ID NO: 16           moltype = AA  length = 653
FEATURE                 Location/Qualifiers
source                  1..653
                        mol_type = protein
                        organism = Homo sapiens
SEQUENCE: 16
MADTLPSEFD VIVIGTGLPE SIIAAACSRS GRRVLHVDSR SYYGGNWASF SFSGLLSWLK    60
EYQENSDIVS DSPVWQDQIL ENEEAIALSR KDKTIQHVEV FCYASQDLHE DVEEAGALQK   120
NHALVTSANS TEAADSAFLP TEDESLSTMS CEMLTEQTPS SDPENALEVN GAEVTGEKEN   180
HCDDKTCVPS TSAEDMSENV PIAEDTTEQP KKNRITYSQI IKEGRRFNID LVSKLLYSRG   240
LLIDLLIKSN VSRYAEFKNI TRILAFREGR VEQVPCSRAD VFNSKQLTMV EKRMLMKFLT   300
FCMEYEKYPD EYKGYEEITF YEYLKTQKLT PNLQYIVMHS IAMTSETASS TIDGLKATKN   360
FLHCLGRYGN TPFLFPLYGQ GELPQCFCRM CAVFGGIYCL RHSVQCLVVD KESRKCKAII   420
DQFGQRIISE HFLVEDSYFP ENMCSRVQYR QISRAVLITD RSVLKTDSDQ QISILTVPAE   480
EPGTFAVRVI ELCSSTMTCM KGTYLVHLTC TSSKTAREDL ESVVQKLFVP YTEMEIENEQ   540
VEKPRILWAL YFNMRDSSDI SRSCYNDLPS NVYVCSGPDC GLGNDNAVKQ AETLFQEICP   600
NEDFCPPPPN PEDIILDGDS LQPEASESSA IPEANSETFK ESTNLGNLEE SSE          653

SEQ ID NO: 17           moltype = AA  length = 212
FEATURE                 Location/Qualifiers
source                  1..212
                        mol_type = protein
                        organism = Homo sapiens
SEQUENCE: 17
MASLFSGRIL IRNNSDQDEL DTEAEVSRRL ENRLVLLFFG AGACPQCQAF VPILKDFFVR    60
LTDEFYVLRA AQLALVYVSQ DSTEEQQDLF LKDMPKKWLF LPFEDDLRRD LGRQFSVERL   120
PAVVVLKPDG DVLTRDGADE IQRLGTACFA NWQEAAEVLD RNFQLPEDLE DQEPRSLTEC   180
LRRHKYRVEK AARGGRDPGG GGGEEGGAGG LF                                 212

SEQ ID NO: 18           moltype = AA  length = 156
FEATURE                 Location/Qualifiers
source                  1..156
                        mol_type = protein
                        organism = Homo sapiens
```

```
SEQUENCE: 18
MVDILGERHL VTCKGATVEA EAALQNKVVA LYFAAARCAP SRDFTPLLCD FYTALVAEAR    60
RPAPFEVVFV SADGSSQEML DFMRELHGAW LALPFHDPYR HELRKRYNVT AIPKLVIVKQ   120
NGEVITNKGR KQIRERGLAC FQDWVEAADI FQNFSV                            156

SEQ ID NO: 19          moltype = AA   length = 135
FEATURE                Location/Qualifiers
source                 1..135
                       mol_type = protein
                       organism = Homo sapiens
SEQUENCE: 19
MVDILGERHL VTCKGATVEA EAALQNKVVA LYFAAARCAP SRDFTPLLCD FYTALVAEAR    60
RPAPFEVVFV SADGSSQEML DFMRELHGAW LALPFHDPYR QRSLALLPRL ECSGVILAHC   120
NLCLLGSSDS LALAS                                                   135

SEQ ID NO: 20          moltype = AA   length = 12
FEATURE                Location/Qualifiers
source                 1..12
                       mol_type = protein
                       organism = synthetic construct
SEQUENCE: 20
TVVSTQAGIG LS                                                       12

SEQ ID NO: 21          moltype = AA   length = 12
FEATURE                Location/Qualifiers
source                 1..12
                       mol_type = protein
                       organism = synthetic construct
SEQUENCE: 21
TGVMHSQASG LS                                                       12

SEQ ID NO: 22          moltype = AA   length = 12
FEATURE                Location/Qualifiers
source                 1..12
                       mol_type = protein
                       organism = synthetic construct
SEQUENCE: 22
TGDGSPAAPG LS                                                       12

SEQ ID NO: 23          moltype = AA   length = 12
FEATURE                Location/Qualifiers
source                 1..12
                       mol_type = protein
                       organism = synthetic construct
SEQUENCE: 23
TGSDMAHGTG LS                                                       12

SEQ ID NO: 24          moltype = AA   length = 17
FEATURE                Location/Qualifiers
source                 1..17
                       mol_type = protein
                       organism = synthetic construct
SEQUENCE: 24
TGLDATRDHG LSPVTGT                                                  17

SEQ ID NO: 25          moltype = AA   length = 17
FEATURE                Location/Qualifiers
source                 1..17
                       mol_type = protein
                       organism = synthetic construct
SEQUENCE: 25
TGSDGTRDHG LSPVTWT                                                  17

SEQ ID NO: 26          moltype = AA   length = 17
FEATURE                Location/Qualifiers
source                 1..17
                       mol_type = protein
                       organism = synthetic construct
SEQUENCE: 26
NGAVADYTRG LSPATGT                                                  17

SEQ ID NO: 27          moltype = AA   length = 17
FEATURE                Location/Qualifiers
source                 1..17
                       mol_type = protein
                       organism = synthetic construct
SEQUENCE: 27
TGGDPTRGTG LSPVTGA                                                  17
```

| | | |
|---|---|---|
| SEQ ID NO: 28 | moltype = AA length = 16 | |
| FEATURE | Location/Qualifiers | |
| source | 1..16 | |
| | mol_type = protein | |
| | organism = synthetic construct | |
| SEQUENCE: 28 | | |
| LQKNARPAST ESVNFQ | | 16 |
| | | |
| SEQ ID NO: 29 | moltype = AA length = 16 | |
| FEATURE | Location/Qualifiers | |
| source | 1..16 | |
| | mol_type = protein | |
| | organism = synthetic construct | |
| SEQUENCE: 29 | | |
| LQRGVRIPSV LEVNGQ | | 16 |
| | | |
| SEQ ID NO: 30 | moltype = AA length = 16 | |
| FEATURE | Location/Qualifiers | |
| source | 1..16 | |
| | mol_type = protein | |
| | organism = synthetic construct | |
| SEQUENCE: 30 | | |
| LQRGNRPVTT ADVNTQ | | 16 |
| | | |
| SEQ ID NO: 31 | moltype = AA length = 16 | |
| FEATURE | Location/Qualifiers | |
| source | 1..16 | |
| | mol_type = protein | |
| | organism = synthetic construct | |
| SEQUENCE: 31 | | |
| LQKADRQPGV VVVNCQ | | 16 |
| | | |
| SEQ ID NO: 32 | moltype = AA length = 1368 | |
| FEATURE | Location/Qualifiers | |
| source | 1..1368 | |
| | mol_type = protein | |
| | organism = Streptococcus pyogenes | |
| SEQUENCE: 32 | | |
| MDKKYSIGLD IGTNSVGWAV ITDEYKVPSK KFKVLGNTDR HSIKKNLIGA LLFDSGETAE | | 60 |
| ATRLKRTARR RYTRRKNRIC YLQEIFSNEM AKVDDSFFHR LEESFLVEED KKHERHPIFG | | 120 |
| NIVDEVAYHE KYPTIYHLRK KLVDSTDKAD LRLIYLALAH MIKFRGHFLI EGDLNPDNSD | | 180 |
| VDKLFIQLVQ TYNQLFEENP INASGVDAKA ILSARLSKSR RLENLIAQLP GEKKNGLFGN | | 240 |
| LIALSLGLTP NFKSNFDLAE DAKLQLSKDT YDDDLDNLLA QIGDQYADLF LAAKNLSDAI | | 300 |
| LLSDILRVNT EITKAPLSAS MIKRYDEHHQ DLTLLKALVR QQLPEKYKEI FFDQSKNGYA | | 360 |
| GYIDGGASQE EFYKFIKPIL EKMDGTEELL VKLNREDLLR KQRTFDNGSI PHQIHLGELH | | 420 |
| AILRRQEDFY PFLKDNREKI EKILTFRIPY YVGPLARGNS RFAWMTRKSE ETITPWNFEE | | 480 |
| VVDKGASAQS FIERMTNFDK NLPNEKVLPK HSLLYEYFTV YNELTKVKYV TEGMRKPAFL | | 540 |
| SGEQKKAIVD LLFKTNRKVT VKQLKEDYFK KIECFDSVEI SGVEDRFNAS LGTYHDLLKI | | 600 |
| IKDKDFLDNE ENEDILEDIV LTLTLFEDRE MIEERLKTYA HLFDDKVMKQ LKRRRYTGWG | | 660 |
| RLSRKLINGI RDKQSGKTIL DFLKSDGFAN RNFMQLIHDD SLTFKEDIQK AQVSGQGDSL | | 720 |
| HEHIANLAGS PAIKKGILQT VKVVDELVKV MGRHKPENIV IEMARENQTT QKGQKNSRER | | 780 |
| MKRIEEGIKE LGSQILKEHP VENTQLQNEK LYLYYLQNGR DMYVDQELDI NRLSDYDVDH | | 840 |
| IVPQSFLKDD SIDNKVLTRS DKNRGKSDNV PSEEVVKKMK NYWRQLLNAK LITQRKFDNL | | 900 |
| TKAERGGLSE LDKAGFIKRQ LVETRQITKH VAQILDSRMN TKYDENDKLI REVKVITLKS | | 960 |
| KLVSDFRKDF QFYKVREINN YHHAHDAYLN AVVGTALIKK YPKLESEFVY GDYKVYDVRK | | 1020 |
| MIAKSEQEIG KATAKYFFYS NIMNFFKTEI TLANGEIRKR PLIETNGETG EIVWDKGRDF | | 1080 |
| ATVRKVLSMP QVNIVKKTEV QTGGFSKESI LPKRNSDKLI ARKKDWDPKK YGGFDSPTVA | | 1140 |
| YSVLVVAKVE KGKSKKLKSV KELLGITIME RSSFEKNPID FLEAKGYKEV KKDLIIKLPK | | 1200 |
| YSLFELENGR KRMLASAGEL QKGNELALPS KYVNFLYLAS HYEKLKGSPE DNEQKQLFVE | | 1260 |
| QHKHYLDEII EQISEFSKRV ILADANLDKV LSAYNKHRDK PIREQAENII HLFTLTNLGA | | 1320 |
| PAAFKYFDTT IDRKRYTSTK EVLDATLIHQ SITGLYETRI DLSQLGGD | | 1368 |
| | | |
| SEQ ID NO: 33 | moltype = AA length = 1053 | |
| FEATURE | Location/Qualifiers | |
| source | 1..1053 | |
| | mol_type = protein | |
| | organism = Staphylococcus aureus | |
| SEQUENCE: 33 | | |
| MKRNYILGLD IGITSVGYGI IDYETRDVID AGVRLFKEAN VENNEGRRSK RGARRLKRRR | | 60 |
| RHRIQRVKKL LFDYNLLTDH SELSGINPYE ARVKGLSQKL SEEEFSAALL HLAKRRGVHN | | 120 |
| VNEVEEDTGN ELSTKEQISR NSKALEEKYV AELQLERLKK DGEVRGSINR FKTSDYVKEA | | 180 |
| KQLLKVQKAY HQLDQSFIDT YIDLLETRRT YYEGPGEGSP FGWKDIKEWY EMLMGHCTYF | | 240 |
| PEELRSVKYA YNADLYNALN DLNNLVITRD ENEKLEYYEK FQIIENVFKQ KKKPTLKQIA | | 300 |
| KEILVNEEDI KGYRVTSTGK PEFTNLKVYH DIKDITARKE IIENAELLDQ IAKILTIYQS | | 360 |
| SEDIQEELTN LNSELTQEEI EQISNLKGYT GTHNLSLKAI NLILDELWHT NDNQIAIFNR | | 420 |
| LKLVPKKVDL SQQKEIPTTL VDDFILSPVV KRSFIQSIKV INAIIKKYGL PNDIIIELAR | | 480 |
| EKNSKDAQKM INEMQKRNRQ TNERIEEIIR TTGKENAKYL IEKIKLHDMQ EGKCLYSLEA | | 540 |
| IPLEDLLNNP FNYEVDHIIP RSVSFDNSFN NKVLVKQEEN SKKGNRTPFQ YLSSSDSKIS | | 600 |
| YETFKKHILN LAKGKGRISK TKKEYLLEER DINRFSVQKD FINRNLVDTR YATRGLMNLL | | 660 |

```
RSYFRVNNLD VKVKSINGGF TSFLRRKWKF KKERNKGYKH HAEDALIIAN ADFIFKEWKK   720
LDKAKKVMEN QMFEEKQAES MPEIETEQEY KEIFITPHQI KHIKDFKDYK YSHRVDKKPN   780
RELINDTLYS TRKDDKGNTL IVNNLNGLYD KDNDKLKKLI NKSPEKLLMY HHDPQTYQKL   840
KLIMEQYGDE KNPLYKYYEE TGNYLTKYSK KDNGPVIKKI KYYGNKLNAH LDITDDYPNS   900
RNKVVKLSLK PYRFDVYLDN GVYKFVTVKN LDVIKKENYY EVNSKCYEEA KKLKKISNQA   960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                              1053

SEQ ID NO: 34            moltype = AA   length = 1300
FEATURE                  Location/Qualifiers
source                   1..1300
                         mol_type = protein
                         organism = Francisella tularensis
SEQUENCE: 34
MSIYQEFVNK YSLSKTLRFE LIPQGKTLEN IKARGLILDD EKRAKDYKKA KQIIDKYHQF    60
FIEEILSSVC ISEDLLQNYS DVYFKLKKSD DDNLQKDFKS AKDTIKKQIS EYIKDSEKFK   120
NLFNQNLIDA KKGQESDLIL WLKQSKDNGI ELFKANSDIT DIDEALEIIK SFKGWTTYFK   180
GFHENRKNVY SSNDIPTSII YRIVDDNLPK FLENKAKYES LKDKAPEAIN YEQIKKDLAE   240
ELTFDIDYKT SEVNQRVFSL DEVFEIANFN NYLNQSGITK FNTIIGGKFV NGENTKRKGI   300
NEYINLYSQQ INDKTLKKYK MSVLFKQILS DTESKSFVID KLEDDSDVVT TMQSFYEQIA   360
AFKTVEEKSI KETLSLLFDD LKAQKLDLSK IYFKNDKSLT DLSQQVFDDY SVIGTAVLEY   420
ITQQIAPKNL DNPSKKEQEL IAKKTEKAKY LSLETIKLAL EEFNKHRDID KQCRFEEILA   480
NFAAIPMIFD EIAQNKDNLA QISIKYQNQG KKDLLQASAE DDVKAIKDLL DQTNNLLHKL   540
KIFHISQSED KANILDKDEH FYLVFEECYF ELANIVPLYN KIRNYITQKP YSDEKFKLNF   600
ENSTLANGWD KNKEPDNTAI LFIKDDKYYL GVMNKKNNKI FDDKAIKENK GEGYKKIVYK   660
LLPGANKMLP KVFFSAKSIK FYNPSEDILR IRNHSTHTKN GSPQKGYEKF EFNIEDCRKF   720
IDFYKQSISK HPEWKDFGFR FSDTQRYNSI DEFYREVENQ GYKLTFENIS ESYIDSVVNQ   780
GKLYLFQIYN KDFSAYSKGR PNLHTLYWKA LFDERNLQDV VYKLNGEAEL FYRKQSIPKK   840
ITHPAKEAIA NKNKDNPKKE SVFEYDLIKD KRFTEDKFFF HCPITINFKS SGANKFNDEI   900
NLLLKEKAND VHILSIDRGE RHLAYYTLVD GKGNIIKQST FNIIGNDRMK TNYHDKLAAI   960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 35            moltype = AA   length = 10
FEATURE                  Location/Qualifiers
source                   1..10
                         mol_type = protein
                         organism = synthetic construct
SEQUENCE: 35
LALIQDSMRA                                                           10

SEQ ID NO: 36            moltype = AA   length = 42
FEATURE                  Location/Qualifiers
source                   1..42
                         mol_type = protein
                         organism = synthetic construct
SEQUENCE: 36
PVATEQYGSV STNLQRGNRQ AATADVNTQG VLPGMVWQDR DV                        42

SEQ ID NO: 37            moltype = AA   length = 42
FEATURE                  Location/Qualifiers
source                   1..42
                         mol_type = protein
                         organism = synthetic construct
SEQUENCE: 37
PVATERFGTV AVNFQSSSTD PATGDVHAMG ALPGMVWQDR DV                        42

SEQ ID NO: 38            moltype = AA   length = 42
FEATURE                  Location/Qualifiers
source                   1..42
                         mol_type = protein
                         organism = synthetic construct
SEQUENCE: 38
RVAYNVGGQM ATNNQSSTTA PATGTYNLQE IVPGSVWMER DV                        42

SEQ ID NO: 39            moltype = AA   length = 42
FEATURE                  Location/Qualifiers
source                   1..42
                         mol_type = protein
                         organism = synthetic construct
SEQUENCE: 39
PVATERFGTV AVNLQSSSTD PATGDVHVMG ALPGMVWQDR DV                        42

SEQ ID NO: 40            moltype = AA   length = 42
FEATURE                  Location/Qualifiers
```

```
                              -continued source                   1..42
                         mol_type = protein
                         organism = synthetic construct
SEQUENCE: 40
PVATEEYGIV SSNLQAANTA AQTQVVNNQG ALPGMVWQNR DV                    42

SEQ ID NO: 41            moltype = AA  length = 42
FEATURE                  Location/Qualifiers
source                   1..42
                         mol_type = protein
                         organism = synthetic construct
SEQUENCE: 41
PVATEEYGIV ADNLQQQNTA PQIGTVNSQG ALPGMVWQNR DV                    42

SEQ ID NO: 42            moltype = AA  length = 42
FEATURE                  Location/Qualifiers
source                   1..42
                         mol_type = protein
                         organism = synthetic construct
SEQUENCE: 42
PVATESYGQV ATNHQSAQAQ AQTGWVQNQG ILPGMVWQDR DV                    42

SEQ ID NO: 43            moltype = AA  length = 42
FEATURE                  Location/Qualifiers
source                   1..42
                         mol_type = protein
                         organism = synthetic construct
SEQUENCE: 43
PVATEQYGVV ADNLQQANTG PIVGNVNSQG ALPGMVWQNR DV                    42

SEQ ID NO: 44            moltype = AA  length = 42
FEATURE                  Location/Qualifiers
source                   1..42
                         mol_type = protein
                         organism = synthetic construct
SEQUENCE: 44
ATDTDMWGNL PGGDQSNSNL PTVDRLTALG AVPGMVWQNR DI                    42

SEQ ID NO: 45            moltype = AA  length = 42
FEATURE                  Location/Qualifiers
VARIANT                  6
                         note = Xaa can be any naturally occurring amino acid
VARIANT                  12
                         note = Xaa can be any naturally occurring amino acid
VARIANT                  22
                         note = Xaa can be any naturally occurring amino acid
VARIANT                  25
                         note = Xaa can be any naturally occurring amino acid
source                   1..42
                         mol_type = protein
                         organism = synthetic construct
SEQUENCE: 45
PVATEXYGVV AXNLQSSNTA PXTGXVNSQG ALPGMVWQNR DV                    42

SEQ ID NO: 46            moltype = AA  length = 60
FEATURE                  Location/Qualifiers
VARIANT                  1..2
                         note = Xaa can be any naturally occurring amino acid
VARIANT                  43
                         note = Xaa can be any naturally occurring amino acid
source                   1..60
                         mol_type = protein
                         organism = synthetic construct
SEQUENCE: 46
XXTFSYTFEE VPFHSSYAHS QSLDRLMNPL IDQYLYYLNR TQXNQSGSAQ NKDLLFSRGS  60

SEQ ID NO: 47            moltype = AA  length = 60
FEATURE                  Location/Qualifiers
VARIANT                  1..2
                         note = Xaa can be any naturally occurring amino acid
VARIANT                  43
                         note = Xaa can be any naturally occurring amino acid
source                   1..60
                         mol_type = protein
                         organism = synthetic construct
SEQUENCE: 47
XXTFSYTFED VPFHSSYAHS QSLDRLMNPL IDQYLYYLNR TQXNQSGSAQ NKDLLFSRGS  60

SEQ ID NO: 48            moltype = AA  length = 60
```

```
FEATURE                     Location/Qualifiers
VARIANT                     1..3
                            note = Xaa can be any naturally occurring amino acid
source                      1..60
                            mol_type = protein
                            organism = synthetic construct
SEQUENCE: 48
XXXFSYTFED VPFHSSYAHS QSLDRLMNPL IDQYLYYLNR TQGTTSGTTN QSRLLFSQAG    60

SEQ ID NO: 49               moltype = AA   length = 60
FEATURE                     Location/Qualifiers
VARIANT                     1..3
                            note = Xaa can be any naturally occurring amino acid
VARIANT                     43
                            note = Xaa can be any naturally occurring amino acid
source                      1..60
                            mol_type = protein
                            organism = synthetic construct
SEQUENCE: 49
XXXFSYTFED VPFHSSYAHS QSLDRLMNPL IDQYLYYLSR TNXTPSGTTT QSRLQFSQAG    60

SEQ ID NO: 50               moltype = AA   length = 60
FEATURE                     Location/Qualifiers
VARIANT                     45
                            note = Xaa can be any naturally occurring amino acid
source                      1..60
                            mol_type = protein
                            organism = synthetic construct
SEQUENCE: 50
NFQFTYTFED VPFHSSYAHS QSLDRLMNPL IDQYLYYLSR TQTTXGGTAN TQTLGFSQGG    60

SEQ ID NO: 51               moltype = AA   length = 60
FEATURE                     Location/Qualifiers
VARIANT                     45
                            note = Xaa can be any naturally occurring amino acid
source                      1..60
                            mol_type = protein
                            organism = synthetic construct
SEQUENCE: 51
NFQFTYTFED VPFHSSYAHS QSLDRLMNPL IDQYLYYLSR TQTTXGGTAN TQTLGFSQGG    60

SEQ ID NO: 52               moltype = AA   length = 59
FEATURE                     Location/Qualifiers
source                      1..59
                            mol_type = protein
                            organism = synthetic construct
SEQUENCE: 52
FQFSYTFEDV PFHSSYAHSQ SLDRLMNPLI DQYLYYLVRT QTTGTGGTQT LAFSQAGPS     59

SEQ ID NO: 53               moltype = AA   length = 60
FEATURE                     Location/Qualifiers
VARIANT                     45
                            note = Xaa can be any naturally occurring amino acid
source                      1..60
                            mol_type = protein
                            organism = synthetic construct
SEQUENCE: 53
NFEFSYTFED VPFHSSYAHS QSLDRLMNPL IDQYLYYLSR TQSTXGGTQG TQQLLFSQAG    60

SEQ ID NO: 54               moltype = AA   length = 60
FEATURE                     Location/Qualifiers
VARIANT                     1
                            note = Xaa can be any naturally occurring amino acid
source                      1..60
                            mol_type = protein
                            organism = synthetic construct
SEQUENCE: 54
XFEFSYSFED VPFHSSYAHS QSLDRLMNPL IDQYLYYLAR TQSNPGGTAG NRELQFYQGG    60

SEQ ID NO: 55               moltype = AA   length = 60
FEATURE                     Location/Qualifiers
VARIANT                     1
                            note = Xaa can be any naturally occurring amino acid
VARIANT                     43..44
                            note = Xaa can be any naturally occurring amino acid
source                      1..60
                            mol_type = protein
                            organism = synthetic construct
SEQUENCE: 55
```

```
XFQFSYEFEN VPFHSSYAHS QSLDRLMNPL IDQYLYYLSK TIXXNGSGQN QQTLKFSVAG   60

SEQ ID NO: 56           moltype = AA  length = 60
FEATURE                 Location/Qualifiers
VARIANT                 1
                        note = Xaa can be any naturally occurring amino acid
VARIANT                 43..44
                        note = Xaa can be any naturally occurring amino acid
source                  1..60
                        mol_type = protein
                        organism = synthetic construct
SEQUENCE: 56
XFQFSYEFEN VPFHSSYAHS QSLDRLMNPL IDQYLYYLSK TIXXNGSGQN QQTLKFSVAG   60

SEQ ID NO: 57           moltype = AA  length = 60
FEATURE                 Location/Qualifiers
VARIANT                 43..49
                        note = Xaa can be any naturally occurring amino acid
source                  1..60
                        mol_type = protein
                        organism = synthetic construct
SEQUENCE: 57
NFEFTYNFEE VPFHSSFAPS QNLFKLANPL VDQYLYRFVS TNXXXXXXXN TGGVQFNKNL   60

SEQ ID NO: 58           moltype = AA  length = 60
FEATURE                 Location/Qualifiers
source                  1..60
                        mol_type = protein
                        organism = synthetic construct
SEQUENCE: 58
PAGMSVQPKN WLPGPCYRQQ RVSKTKTDNN NSNFTWTGAS KYNLNGRESI INPGTAMASH   60

SEQ ID NO: 59           moltype = AA  length = 60
FEATURE                 Location/Qualifiers
source                  1..60
                        mol_type = protein
                        organism = synthetic construct
SEQUENCE: 59
PAGMSVQPKN WLPGPCYRQQ RVSKTKTDNN NSNFTWTGAS KYNLNGRESI INPGTAMASH   60

SEQ ID NO: 60           moltype = AA  length = 60
FEATURE                 Location/Qualifiers
source                  1..60
                        mol_type = protein
                        organism = synthetic construct
SEQUENCE: 60
PQSMSLQARN WLPGPCYRQQ RLSKTANDNN NSNFPWTAAS KYHLNGRDSL VNPGPAMASH   60

SEQ ID NO: 61           moltype = AA  length = 60
FEATURE                 Location/Qualifiers
source                  1..60
                        mol_type = protein
                        organism = synthetic construct
SEQUENCE: 61
ASDIRDQSRN WLPGPCYRQQ RVSKTSADNN NSEYSWTGAT KYHLNGRDSL VNPGPAMASH   60

SEQ ID NO: 62           moltype = AA  length = 60
FEATURE                 Location/Qualifiers
source                  1..60
                        mol_type = protein
                        organism = synthetic construct
SEQUENCE: 62
PNTMANQAKN WLPGPCYRQQ RVSTTTGQNN NSNFAWTAGT KYHLNGRNSL ANPGIAMATH   60

SEQ ID NO: 63           moltype = AA  length = 60
FEATURE                 Location/Qualifiers
source                  1..60
                        mol_type = protein
                        organism = synthetic construct
SEQUENCE: 63
PNTMANQAKN WLPGPCYRQQ RVSTTTGQNN NSNFAWTAGT KYHLNGRNSL ANPGIAMATH   60

SEQ ID NO: 64           moltype = AA  length = 60
FEATURE                 Location/Qualifiers
VARIANT                 2..3
                        note = Xaa can be any naturally occurring amino acid
source                  1..60
                        mol_type = protein
                        organism = synthetic construct
```

```
SEQUENCE: 64
SXXMANQARN WVPGPCYRQQ RVSTTTNQNN NSNFAWTGAA KFKLNGRDSL MNPGVAMASH      60

SEQ ID NO: 65           moltype = AA  length = 60
FEATURE                 Location/Qualifiers
source                  1..60
                        mol_type = protein
                        organism = synthetic construct
SEQUENCE: 65
PANMSAQAKN WLPGPCYRQQ RVSTTLSQNN NSNFAWTGAT KYHLNGRDSL VNPGVAMATH      60

SEQ ID NO: 66           moltype = AA  length = 60
FEATURE                 Location/Qualifiers
source                  1..60
                        mol_type = protein
                        organism = synthetic construct
SEQUENCE: 66
PSTMAEQAKN WLPGPCFRQQ RVSKTLDQNN NSNFAWTGAT KYHLNGRNSL VNPGVAMATH      60

SEQ ID NO: 67           moltype = AA  length = 60
FEATURE                 Location/Qualifiers
source                  1..60
                        mol_type = protein
                        organism = synthetic construct
SEQUENCE: 67
PSNMAVQGRN YIPGPSYRQQ RVSTTVTQNN NSEFAWPGAS SWALNGRNSL MNPGPAMASH      60

SEQ ID NO: 68           moltype = AA  length = 60
FEATURE                 Location/Qualifiers
source                  1..60
                        mol_type = protein
                        organism = synthetic construct
SEQUENCE: 68
PSNMAVQGRN YIPGPSYRQQ RVSTTVTQNN NSEFAWPGAS SWALNGRNSL MNPGPAMASH      60

SEQ ID NO: 69           moltype = AA  length = 60
FEATURE                 Location/Qualifiers
source                  1..60
                        mol_type = protein
                        organism = synthetic construct
SEQUENCE: 69
AGRYANTYKN WFPGPMGRTQ GWNLGSGVNR ASVSAFATTN RMELEGASYQ VPPQPNGMTN      60

SEQ ID NO: 70           moltype = AA  length = 60
FEATURE                 Location/Qualifiers
VARIANT                 19..20
                        note = Xaa can be any naturally occurring amino acid
VARIANT                 32
                        note = Xaa can be any naturally occurring amino acid
source                  1..60
                        mol_type = protein
                        organism = synthetic construct
SEQUENCE: 70
KDDEDKFFPM SGVMIFGKXX ESAGASNTAL DXNVMITDEE EIKATNPVAT ERFGTVAVNF      60

SEQ ID NO: 71           moltype = AA  length = 60
FEATURE                 Location/Qualifiers
VARIANT                 19..20
                        note = Xaa can be any naturally occurring amino acid
VARIANT                 32
                        note = Xaa can be any naturally occurring amino acid
source                  1..60
                        mol_type = protein
                        organism = synthetic construct
SEQUENCE: 71
KDDKDKFFPM SGVMIFGKXX ESAGASNTAL DXNVMITDEE EIKATNPVAT ERFGTVAVNL      60

SEQ ID NO: 72           moltype = AA  length = 60
FEATURE                 Location/Qualifiers
VARIANT                 19..20
                        note = Xaa can be any naturally occurring amino acid
VARIANT                 32
                        note = Xaa can be any naturally occurring amino acid
source                  1..60
                        mol_type = protein
                        organism = synthetic construct
SEQUENCE: 72
KDDEEKFFPM HGNLIFGKXX EGTTASNAEL DXNVMITDEE EIRTTNPVAT EQYGTVANNL      60
```

```
SEQ ID NO: 73            moltype = AA   length = 60
FEATURE                  Location/Qualifiers
VARIANT                  19..20
                         note = Xaa can be any naturally occurring amino acid
VARIANT                  32
                         note = Xaa can be any naturally occurring amino acid
source                   1..60
                         mol_type = protein
                         organism = synthetic construct
SEQUENCE: 73
KDDEEKFFPQ SGVLIFGKXX QGSEKTNVDI EXKVMITDEE EIRTTNPVAT EQYGSVSTNL    60

SEQ ID NO: 74            moltype = AA   length = 60
FEATURE                  Location/Qualifiers
VARIANT                  19..20
                         note = Xaa can be any naturally occurring amino acid
VARIANT                  32
                         note = Xaa can be any naturally occurring amino acid
source                   1..60
                         mol_type = protein
                         organism = synthetic construct
SEQUENCE: 74
KDDEERFFPS NGILIFGKXX QNAARDNADY SXDVMLTSEE EIKTTNPVAT EEYGIVADNL    60

SEQ ID NO: 75            moltype = AA   length = 60
FEATURE                  Location/Qualifiers
VARIANT                  19..20
                         note = Xaa can be any naturally occurring amino acid
VARIANT                  32
                         note = Xaa can be any naturally occurring amino acid
source                   1..60
                         mol_type = protein
                         organism = synthetic construct
SEQUENCE: 75
KDDEERFFPS NGILIFGKXX QNAARDNADY SXDVMLTSEE EIKTTNPVAT EEYGIVADNL    60

SEQ ID NO: 76            moltype = AA   length = 60
FEATURE                  Location/Qualifiers
VARIANT                  19..20
                         note = Xaa can be any naturally occurring amino acid
VARIANT                  32
                         note = Xaa can be any naturally occurring amino acid
source                   1..60
                         mol_type = protein
                         organism = synthetic construct
SEQUENCE: 76
KDDDDRFFPS SGVLIFGKXX QGAGNDGVDY SXQVLITDEE EIKATNPVAT EEYGAVAINN    60

SEQ ID NO: 77            moltype = AA   length = 60
FEATURE                  Location/Qualifiers
VARIANT                  19..20
                         note = Xaa can be any naturally occurring amino acid
VARIANT                  32
                         note = Xaa can be any naturally occurring amino acid
source                   1..60
                         mol_type = protein
                         organism = synthetic construct
SEQUENCE: 77
KDDEERFFPS SGVLMFGKXX QGAGRDNVDY SXSVMLTSEE EIKTTNPVAT EQYGVVADNL    60

SEQ ID NO: 78            moltype = AA   length = 60
FEATURE                  Location/Qualifiers
VARIANT                  19..20
                         note = Xaa can be any naturally occurring amino acid
VARIANT                  25
                         note = Xaa can be any naturally occurring amino acid
VARIANT                  32
                         note = Xaa can be any naturally occurring amino acid
source                   1..60
                         mol_type = protein
                         organism = synthetic construct
SEQUENCE: 78
KDDEDRFFPS SGVLIFGKXX TGATXNKTTL EXNVLMTNEE EIRPTNPVAT EEYGIVSSNL    60

SEQ ID NO: 79            moltype = AA   length = 60
FEATURE                  Location/Qualifiers
VARIANT                  19..20
                         note = Xaa can be any naturally occurring amino acid
VARIANT                  32
```

```
                    note = Xaa can be any naturally occurring amino acid
source              1..60
                    mol_type = protein
                    organism = synthetic construct
SEQUENCE: 79
KEGEDRFFPL SGSLIFGKXX QGTGRDNVDA DXKVMITNEE EIKTTNPVAT ESYGQVATNH    60

SEQ ID NO: 80       moltype = AA  length = 60
FEATURE             Location/Qualifiers
VARIANT             19..20
                    note = Xaa can be any naturally occurring amino acid
VARIANT             32
                    note = Xaa can be any naturally occurring amino acid
source              1..60
                    mol_type = protein
                    organism = synthetic construct
SEQUENCE: 80
KEGEDRFFPL SGSLIFGKXX QGTGRDNVDA DXKVMITNEE EIKTTNPVAT ESYGQVATNH    60

SEQ ID NO: 81       moltype = AA  length = 60
FEATURE             Location/Qualifiers
source              1..60
                    mol_type = protein
                    organism = synthetic construct
SEQUENCE: 81
NLQGSNTYAL ENTMIFNSQP ANPGTTATYL EGNMLITSES ETQPVNRVAY NVGGQMATNN    60

SEQ ID NO: 82       moltype = AA  length = 60
FEATURE             Location/Qualifiers
source              1..60
                    mol_type = protein
                    organism = synthetic construct
SEQUENCE: 82
QSSSTDPATG DVHAMGALPG MVWQDRDVYL QGPIWAKIPH TDGHFHPSPL MGGFGLKNPP    60

SEQ ID NO: 83       moltype = AA  length = 60
FEATURE             Location/Qualifiers
source              1..60
                    mol_type = protein
                    organism = synthetic construct
SEQUENCE: 83
QSSSTDPATG DVHVMGALPG MVWQDRDVYL QGPIWAKIPH TDGHFHPSPL MGGFGLKHPP    60

SEQ ID NO: 84       moltype = AA  length = 60
FEATURE             Location/Qualifiers
source              1..60
                    mol_type = protein
                    organism = synthetic construct
SEQUENCE: 84
QSSNTAPTTG TVNHQGALPG MVWQDRDVYL QGPIWAKIPH TDGHFHPSPL MGGFGLKHPP    60

SEQ ID NO: 85       moltype = AA  length = 60
FEATURE             Location/Qualifiers
source              1..60
                    mol_type = protein
                    organism = synthetic construct
SEQUENCE: 85
QRGNRQAATA DVNTQGVLPG MVWQDRDVYL QGPIWAKIPH TDGHFHPSPL MGGFGLKHPP    60

SEQ ID NO: 86       moltype = AA  length = 60
FEATURE             Location/Qualifiers
source              1..60
                    mol_type = protein
                    organism = synthetic construct
SEQUENCE: 86
QQQNTAPQIG TVNSQGALPG MVWQNRDVYL QGPIWAKIPH TDGNFHPSPL MGGFGLKHPP    60

SEQ ID NO: 87       moltype = AA  length = 60
FEATURE             Location/Qualifiers
source              1..60
                    mol_type = protein
                    organism = synthetic construct
SEQUENCE: 87
QGQRQAAQIG TVNSQGALPG MVWQNRDVYL QGPIWAKIPH TDGNFHPSPL MGGFGLKHPP    60

SEQ ID NO: 88       moltype = AA  length = 60
FEATURE             Location/Qualifiers
source              1..60
                    mol_type = protein
```

```
                                              -continued
                                    organism = synthetic construct
SEQUENCE: 88
QAANTQAQTG LVHNQGVIPG MVWQNRDVYL QGPIWAKIPH TDGNFHPSPL MGGFGLKHPP      60

SEQ ID NO: 89           moltype = AA  length = 60
FEATURE                 Location/Qualifiers
source                  1..60
                        mol_type = protein
                        organism = synthetic construct
SEQUENCE: 89
QQANTGPIVG NVNSQGALPG MVWQNRDVYL QGPIWAKIPH TDGNFHPSPL MGGFGLKHPP      60

SEQ ID NO: 90           moltype = AA  length = 60
FEATURE                 Location/Qualifiers
source                  1..60
                        mol_type = protein
                        organism = synthetic construct
SEQUENCE: 90
QAANTAAQTQ VVNNQGALPG MVWQNRDVYL QGPIWAKIPH TDGNFHPSPL MGGFGLKHPP      60

SEQ ID NO: 91           moltype = AA  length = 60
FEATURE                 Location/Qualifiers
source                  1..60
                        mol_type = protein
                        organism = synthetic construct
SEQUENCE: 91
QSAQAQAQTG WVQNQGILPG MVWQDRDVYL QGPIWAKIPH TDGNFHPSPL MGGFGMKHPP      60

SEQ ID NO: 92           moltype = AA  length = 60
FEATURE                 Location/Qualifiers
source                  1..60
                        mol_type = protein
                        organism = synthetic construct
SEQUENCE: 92
QSGQAQAATG WVQNQGILPG MVWQDRDVYL QGPIWAKIPH TDGNFHPSPL MGGFGMKHPP      60

SEQ ID NO: 93           moltype = AA  length = 60
FEATURE                 Location/Qualifiers
source                  1..60
                        mol_type = protein
                        organism = synthetic construct
SEQUENCE: 93
QSSTTAPATG TYNLQEIVPG SVWMERDVYL QGPIWAKIPE TGAHFHPSPA MGGFGLKHPP      60

SEQ ID NO: 94           moltype = AA  length = 7
FEATURE                 Location/Qualifiers
VARIANT                 7
                        note = Xaa can be any naturally occurring amino acid
source                  1..7
                        mol_type = protein
                        organism = synthetic construct
SEQUENCE: 94
PQILIKX                                                                 7

SEQ ID NO: 95           moltype = AA  length = 7
FEATURE                 Location/Qualifiers
VARIANT                 7
                        note = Xaa can be any naturally occurring amino acid
source                  1..7
                        mol_type = protein
                        organism = synthetic construct
SEQUENCE: 95
PQIMIKX                                                                 7

SEQ ID NO: 96           moltype = AA  length = 7
FEATURE                 Location/Qualifiers
source                  1..7
                        mol_type = protein
                        organism = synthetic construct
SEQUENCE: 96
PQILIKN                                                                 7

SEQ ID NO: 97           moltype = AA  length = 7
FEATURE                 Location/Qualifiers
source                  1..7
                        mol_type = protein
                        organism = synthetic construct
SEQUENCE: 97
PMMLIKN                                                                 7
```

| SEQ ID NO: 98 | moltype = AA  length = 12 |
| --- | --- |
| FEATURE | Location/Qualifiers |
| source | 1..12 |
| | mol_type = protein |
| | organism = synthetic construct |

SEQUENCE: 98
TGDGGTTMNG LS                                                              12

| SEQ ID NO: 99 | moltype = AA  length = 12 |
| --- | --- |
| FEATURE | Location/Qualifiers |
| source | 1..12 |
| | mol_type = protein |
| | organism = synthetic construct |

SEQUENCE: 99
TGGHGSAPDG LS                                                              12

| SEQ ID NO: 100 | moltype = AA  length = 12 |
| --- | --- |
| FEATURE | Location/Qualifiers |
| source | 1..12 |
| | mol_type = protein |
| | organism = synthetic construct |

SEQUENCE: 100
TGMHVTMMAG LN                                                              12

| SEQ ID NO: 101 | moltype = AA  length = 12 |
| --- | --- |
| FEATURE | Location/Qualifiers |
| source | 1..12 |
| | mol_type = protein |
| | organism = synthetic construct |

SEQUENCE: 101
TGASYLDNSG LS                                                              12

| SEQ ID NO: 102 | moltype = AA  length = 860 |
| --- | --- |
| FEATURE | Location/Qualifiers |
| source | 1..860 |
| | mol_type = protein |
| | organism = Homo sapiens |

SEQUENCE: 102
MGEVTAEEVE KFLDSNIGFA KQYYNLHYRA KLISDLLGAK EAAVDFSNYH SPSSMEESEI    60
IFDLLRDFQE NLQTEKCIFN VMKKLCFLLQ ADRMSLFMYR TRNGIAELAT RLFNVHKDAV   120
LEDCLVMPDQ EIVFPLDMGI VGHVAHSKKI ANVPNTEEDE HFCDFVDILT EYKTKNILAS   180
PIMNGKDVVA IIMAVNKVDG SHFTKRDEEI LLKYLNFANL IMKVYHLSYL HNCETRRGQI   240
LLWSGSKVFE ELTDIERQFH KALYTVRAFL NCDRYSVGLL DMTKQKEFFD VWPVLMGEVP   300
PYSGPRTPDG REINFYKVID YILHGKEDIK VIPNPPPDHW ALVSGLPAYV AQNGLICNIM   360
NAPAEDFFAF QKEPLDESGW MIKNVLSMPI VNKKEEIVGV ATFYNRKDGK PFDEMDETLM   420
ESLTQFLGWS VLNPDTYESM NKLENRKDIF QDIVKYHVKC DNEEIQKILK TREVYGKEPW   480
ECEEEELAEI LQAELPDADK YEINKFHFSD LPLTELELVK CGIQMYYELK VVDKFHIPQE   540
ALVRFMYSLS KGYRKITYHN WRHGFNVGQT MFSLLVTGKL KRYFTDLEAL AMVTAAFCHD   600
IDHRGTNNLY QMKSQNPLAK LHGSSILERH HLEFGKTLLR DESLNIFQNL NRRQHEHAIH   660
MMDIAIIATD LALYFKKRTM FQKIVDQSKT YESEQEWTYV MMLEQTRKEI VMAMMMTACD   720
LSAITKPWEV QSQVALLVAA EFWEQGDLER TVLQQNPIPM MDRNKADELP KLQVGFIDFV   780
CTFVYKEFSR FHEEITPMLD GITNNRKEWK ALADEYDAKM KVQEEKKQKQ QSAKSAAAGN   840
QPGGNPSPGG ATTSKSCCIQ                                              860

| SEQ ID NO: 103 | moltype = AA  length = 854 |
| --- | --- |
| FEATURE | Location/Qualifiers |
| source | 1..854 |
| | mol_type = protein |
| | organism = Homo sapiens |

SEQUENCE: 103
MSLSEEQARS FLDQNPDFAR QYFGKKLSPE NVAAACEDGC PPDCDSLRDL CQVEESTALL    60
ELVQDMQESI NMERVVFKVL RRLCTLLQAD RCSLFMYRQR NGVAELATRL FSVQPDSVLE   120
DCLVPPDSEI VFPLDIGVVG HVAQTKKMVN VEDVAECPHF SSFADELTDY KTKNMLATPI   180
MNGKDVVAVI MAVNKLNGPF FTSEDEDVFL KYLNFATLYL KIYHLSYLHN CETRRGQVLL   240
WSANKVFEEL TDIERQFHKA FYTVRAYLNC ERYSVGLLDM TKEKEFFDVW SVLMGESQPY   300
SGPRTPDGRE IVFYKVIDYI LHGKEEIKVI PTPSADHWAL ASGLPSYVAE SGFICNIMNA   360
SADEMPKFQE GALDDSGWLI KNVLSMPIVN KKEEIVGVAT FYNRKDGKPF DEQDEVLMES   420
LTQFLGWSVM NTDTYDKMNK LENRKDIAQD MVLYHVKCDR DEIQLILPTR ARLGKEPADC   480
DEDEDELGEILK EELPGPTTFD IYEFHFSDLE CTELDLVKCG IQMYYELGVV RKFQIPQEVL   540
VRFLFSISKG YRRITYHNWR HGFNVAQTMF TLLMTGKLKS YYTDLEAFAM VTAGLCHDID   600
HRGTNNLYQM KSQNPLAKLH GSSILERHHL EFGKFLLSEE TLNIYQNLNR RQHEHVIHLM   660
DIAIIATDLA LYFKKRAMFQ KIVDESKNYQ DKKSWVEYLS LETTRKEIVM AMMMTACDLS   720
AITKPWEVQS KVALLVAAEF WEQGDLERTV LDQQPIPMMD RNKAAELPKL QVGFIDFVCT   780
FVYKEFSRFH EEILPMFDRL QNNRKEWKAL ADEYEAKVKA LEEKEEEERV AAKKVGTEIC   840
NGGPAPKSST CCIL                                                    854

| SEQ ID NO: 104 | moltype = AA  length = 853 |
| --- | --- |
| FEATURE | Location/Qualifiers |

```
source                  1..853
                        mol_type = protein
                        organism = Homo sapiens
SEQUENCE: 104
MSLSEEQARS FLDQNPDFAR QYFGKKLSPE NVAAACEDGC PPDCDSLRDL CQVEESTALL    60
ELVQDMQESI NMERVVFKVL RRLCTLLQAD RCSLFMYRQR NGVAELATRL FSVQPDSVLE   120
DCLVPPDSEI VFPLDIGVVG HVAQTKKMVN VEDVAECPHF SSFADELTDY KTKNMLATPI   180
MNGKDVVAVI MAVNKLNGPF FTSEDEDVFL KYLNFATLYL KIYHLSYLHN CETRRGQVLL   240
WSANKVFEEL TDIERQFHKA FYTVRAYLNC ERYSVGLLDM TKEKEFFDVW SVLMGESQPY   300
SGPRTPDGRE IVFYKVIDYI LHGKEEIKVI PTPSADHWAL ASGLPSYVAE SGFICNIMNA   360
SADEMFKFQE GALDDSGWLI KNVLSMPIVN KKEEIVGVAT FYNRKDGKPF DEQDEVLMES   420
LTQFLGWSVM NTDTYDKMNK LENRKDIAQD MVLYHVKCDR DEIQLILPTR ARLGKEPADC   480
DEDELGEILK EELPGPTTFD IYEFHFSDLE CTELDLVKCG IQMYYELGVV RKFQIPQEVL   540
VRFLFSISKG YRRITYHNWR HGFNVAQTMF TLLMTGKLKS YYTDLEAFAM VTAGLCHDID   600
HRGTNNLYQM KSQNPLAKLH GSSILERHHL EFGKFLLSEE TLNIYQNLNR RQHEHVIHLM   660
DIAIIATDLA LYFKKRAMFQ KIVDESKNYQ DKKSWVEYLS LETTRKEIVM AMMMTACDLS   720
AITKPWEVQS KVALLVAAEF WEQGDLERTV LDQQPIPMMD RNKAAELPKL QVGFIDFVCT   780
FVYKEFSRFH EEILPMFDRL QNNRKEWKAL ADEYEAKVKA LEEKEEEERV AAKKGTEICN   840
GGPAPKSSTC CIL                                                    853

SEQ ID NO: 105          moltype = AA   length = 575
FEATURE                 Location/Qualifiers
source                  1..575
                        mol_type = protein
                        organism = Homo sapiens
SEQUENCE: 105
MTKEKEFFDV WSVLMGESQP YSGPRTPDGR EIVFYKVIDY ILHGKEEIKV IPTPSADHWA    60
LASGLPSYVA ESGFICNIMN ASADEMFKFQ EGALDDSGWL IKNVLSMPIV NKKEEIVGVA   120
TFYNRKDGKP FDEQDEVLME SLTQFLGWSV MNTDTYDKMN KLENRKDIAQ DMVLYHVKCD   180
RDEIQLILPT RARLGKEPAD CDEDELGEIL KEELPGPTTF DIYEFHFSDL ECTELDLVKC   240
GIQMYYELGV VRKFQIPQEV LVRFLFSISK GYRRITYHNW RHGFNVAQTM FTLLMTGKLK   300
SYYTDLEAFA MVTAGLCHDI DHRGTNNLYQ MKSQNPLAKL HGSSILERHH LEFGKFLLSE   360
ETLNIYQNLN RRQHEHVIHL MDIAIIATDL ALYFKKRAMF QKIVDESKNY QDKKSWVEYL   420
SLETTRKEIV MAMMMTACDL SAITKPWEVQ SKVALLVAAE FWEQGDLERT VLDQQPIPMM   480
DRNKAAELPK LQVGFIDFVC TFVYKEFSRF HEEILPMFDR LQNNRKEWKA LADEYEAKVK   540
ALEEKEEEER VAAKKVGTEI CNGGPAPKSS TCCIL                             575

SEQ ID NO: 106          moltype = AA   length = 694
FEATURE                 Location/Qualifiers
source                  1..694
                        mol_type = protein
                        organism = Homo sapiens
SEQUENCE: 106
MAKINTQYSH PSRTHLKVKT SDRDLNRAEN GLSRAHSSSE ETSSVLQPGI AMETRGLADS    60
GQGSFTGQGI ARLSRLIFLL RRWAARHVHH QDQGPDSFPD RFRGAELKEV SSQESNAQAN   120
VGSQEPADRG RSAWPLAKCN TNTSNNTEEE KKTKKKDAIV VDPSSNLYYR WLTAIALPVF   180
YNWYLLICRA CFDELQSEYL MLWLVLDYSA DVLYVLDVLV RARTGFLEQG LMVSDTNRLW   240
QHYKTTTQFK LDVLSLVPTD LAYLKVGTNY PEVRFNRLLK FSRLFEFFDR TETRTNYPNM   300
FRIGNLVLYI LIIIHWNACI YFAISKFIGF GTDSWVYPNI SIPEHGRLSR KYIYSLYWST   360
LTLTTIGETP PPVKDEEYLF VVVDFLVGVL IFATIVGNVG SMISNMNASR AEFQAKIDSI   420
KQYMQFRKVT KDLETRVIRW FDYLWANKKT VDEKEVLKSL PDKLKAEIAI NVHLDTLKKV   480
RIFQDCEAGL LVELVLKLRP TVFSPGDYIC KKGDIGKEMY IINEGKLAVV ADDGVTQFVV   540
LSDGSYFGEI SILNIKGSKS GNRRTANIRS IGYSDLFCLS KDDLMEALTE YPEAKKALEE   600
KGRQILMKDN LIDEELARAG ADPKDLEEKV EQLGSSLDTL QTRFARLLAE YNATQMKMKQ   660
RLSQLESQVK GGGDKPLADG EVPGDATKTE DKQQ                              694

SEQ ID NO: 107          moltype = AA   length = 676
FEATURE                 Location/Qualifiers
source                  1..676
                        mol_type = protein
                        organism = Homo sapiens
SEQUENCE: 107
MAKINTQYSH PSRTHLKVKT SDRDLNRAEN GLSRAHSSSE ETSSVLQPGI AMETRGLADS    60
GQGSFTGQGI ARLSRLIFLL RRWAARHVHH QDQGPDSFPD RFRGAELKEV SSQESNAQAN   120
VGSQEPADRG RRKKTKKKDA IVVDPSSNLY YRWLTAIALP VFYNWYLLIC RACFDELQSE   180
YLMLWLVLDY SADVLYVLDV LVRARTGFLE QGLMVSDTNR LWQHYKTTTQ FKLDVLSLVP   240
TDLAYLKVGT NYPEVRFNRL LKFSRLFEFF DRTETRTNYP NMFRIGNLVL YILIIIHWNA   300
CIYFAISKFI GFGTDSWVYP NISIPEHGRL SRKYIYSLYW STLTLTTIGE TPPPVKDEEY   360
LFVVVDFLVG VLIFATIVGN VGSMISNMNA SRAEFQAKID SIKQYMQFRK VTKDLETRVI   420
RWFDYLWANK KTVDEKEVLK SLPDKLKAEI AINVHLDTLK KVRIFQDCEA GLLVELVLKL   480
RPTVFSPGDY ICKKGDIGKE MYIINEGKLA VVADDGVTQF VVLSDGSYFG EISILNIKGS   540
KSGNRRTANI RSIGYSDLFC LSKDDLMEAL TEYPEAKKAL EEKGRQILMK DNLIDEELAR   600
AGADPKDLEE KVEQLGSSLD TLQTRFARLL AEYNATQMKM KQRLSQLESQ VKGGGDKPLA   660
DGEVPGDATK TEDKQQ                                                  676

SEQ ID NO: 108          moltype = AA   length = 809
FEATURE                 Location/Qualifiers
source                  1..809
                        mol_type = protein
```

```
                    organism = Homo sapiens
SEQUENCE: 108
MPKSLTKVNK VKPIGENNEN EQSSRRNEEG SHPSNQSQQT TAQEENKGEE KSLKTKSTPV    60
TSEEPHTNIQ DKLSKKNSSG DLTTNPDPQN AAEPTGTVPE QKEMDPGKEG PNSPQNKPPA   120
APVINEYADA QLHNLVKRMR QRTALYKKKL VEGDLSSPEA SPQTAKPTAV PPVKESDDKP   180
TEHYYRLLWF KVKKMPLTEY LKRIKLPNSI DSYTDRLYLL WLLLVTLAYN WNCCFIPLRL   240
VFPYQTADNI HYWLIADIIC DIIYLYDMLF IQPRLQFVRG GDIIVDSNEL RKHYRTSTKF   300
QLDVASIIPF DICYLFFGFN PMFRANRMLK YTSFFEFNHH LESIMDKAYI YRVIRTTGYL   360
LFILHINACV YYWASNYEGI GTTRWVYDGE GNEYLRCYYW AVRTLITIGG LPEPQTLFEI   420
VFQLLNFFSG VFVFSSLIGQ MRDVIGAATA NQNYFRACMD DTIAYMNNYS IPKLVQKRVR   480
TWYEYTWDSQ RMLDESDLLK TLPTTVQLAL AIDVNFSIIS KVDLFKGCDT QMIYDMLLRL   540
KSVLYLPGDF VCKKGEIGKE MYIIKHGEVQ VLGGPDGTKV LVTLKAGSVF GEISLLAAGG   600
GNRRTANVVA HGFANLLTLD KKTLQEILVH YPDSERILMK KARVLLKQKA KTAEATPPRK   660
DLALLFPPKE ETPKLFKTLL GGTGKASLAR LLKLKREQAA QKKENSEGGE EEGKENEDKQ   720
KENEDKQKEN EDKGKENEDK DKGREPEEKP LDRPECTASP IAVEEEPHSV RRTVLPRGTS   780
RQSLIISMAP SAEGGEEVLT IEVKEKAKQ                                    809

SEQ ID NO: 109          moltype = AA  length = 354
FEATURE                 Location/Qualifiers
source                  1..354
                        mol_type = protein
                        organism = Homo sapiens
SEQUENCE: 109
MGSGASAEDK ELAKRSKELE KKLQEDADKE AKTVKLLLLG AGESGKSTIV KQMKIIHQDG    60
YSPEECLEFK AIIYGNVLQS ILAIIRAMTT LGIDYAEPSC ADDGRQLNNL ADSIEEGTMP   120
PELVEVIRRL WKDGGVQACF ERAAEYQLND SASYYLNQLE RITDPEYLPS EQDVLRSRVK   180
TTGIIETKFS VKDLNFRMFD VGGQRSERKK WIHCFEGVTC IIFCAALSAY DMVLVEDDEV   240
NRMHESLHLF NSICNHKFFA ATSIVLFLNK KDLFEEKIKK VHLSICFPEY DGNNSYDDAG   300
NYIKSQFLDL NMRKDVKEIY SHMTCATDTQ NVKFVFDAVT DIIIKENLKD CGLF         354

SEQ ID NO: 110          moltype = AA  length = 815
FEATURE                 Location/Qualifiers
source                  1..815
                        mol_type = protein
                        organism = Homo sapiens
SEQUENCE: 110
MREPEELMPD SGAVFTFGKS KFAENNPGKF WFKNDVPVHL SCGDEHSAVV TGNNKLYMFG    60
SNNWGQLGLG SKSAISKPTC VKALKPEKVK LAACGRNHTL VSTEGGNVYA TGGNNEGQLG   120
LGDTEERNTF HVISFFTSEH KIKQLSAGSN TSAALTEDGR LFMWGDNSEG QIGLKNVSNV   180
CVPQQVTIGK PVSWISCGYY HSAFVTTDGE LYVFGEPENG KLGLPNQLLG NHRTPQLVSE   240
IPEKVIQVAC GGEHTVVLTE NAVYTFGLGQ FGQLGLGTFL FETSEPKVIE NIRDQTISYI   300
SCGENHTALI TDIGLMYTFG DGRHGKLGLG LENFTNHFIP TLCSNFLRFI VKLVACGGCH   360
MVVFAAPHRG VAKEIEFDEI NDTCLSVATF LPYSSLTSGN VLQRTLSARM RRRERERSPD   420
SFSMRRTLPP IEGTLGLSAC FLPNSVFPRC SERNLQESVL SEQDLMQPEE PDYLLDEMTK   480
EAEIDNSSTV ESLGETTDIL NMTHIMSLNS NEKSLKLSPV QKQKKQQTIG ELTQDTALTE   540
NDDSDEYEEM SEMKEGKACK QHVSQGIFMT QPATTIEAFS DEEVEIPEEK EGAEDSKGNG   600
IEEQEVEANE ENVKVHGGRK EKTEILSDDL TDKAEDHEFS ENKVKLEDV DEEINAENVE   660
SKKKTVGDDE SVPTGYHSKT EGAERTNDDS SAETIEKKEK ANLEERAICE YNENPKGYML   720
DDDADSSSLEI LENSETTPSK DMKKTKKIFL FKRVPSINQK IVKNNNEPLP EIKSIGDQII   780
LKSDNKDADQ NHMSQNHQNI PPTNTERRSK SCTIL                              815

SEQ ID NO: 111          moltype = AA  length = 646
FEATURE                 Location/Qualifiers
source                  1..646
                        mol_type = protein
                        organism = Homo sapiens
SEQUENCE: 111
MREPEELMPD SGAVFTFGKS KFAENNPGKF WFKNDVPVHL SCGDEHSAVV TGNNKLYMFG    60
SNNWGQLGLG SKSAISKPTC VKALKPEKVK LAACGRNHTL VSTEGGNVYA TGGNNEGQLG   120
LGDTEERNTF HVISFFTSEH KIKQLSAGSN TSAALTEDGR LFMWGDNSEG QIGLKNVSNV   180
CVPQQVTIGK PVSWISCGYY HSAFVTTDGE LYVFGEPENG KLGLPNQLLG NHRTPQLVSE   240
IPEKVIQVAC GGEHTVVLTE NAVYTFGLGQ FGQLGLGTFL FETSEPKVIE NIRDQTISYI   300
SCGENHTALI TDIGLMYTFG DGRHGKLGLG LENFTNHFIP TLCSNFLRFI VKLVACGGCH   360
MVVFAAPHRG VAKEIEFDEI NDTCLSVATF LPYSSLTSGN VLQRTLSARM RRRERERSPD   420
SFSMRRTLPP IEGTLGLSAC FLPNSVFPRC SERNLQESVL SEQDLMQPEE PDYLLDEMTK   480
EAEIDNSSTV ESLGETTDIL NMTHIMSLNS NEKSLKLSPV QKQKKQQTIG ELTQDTALTE   540
NDDSDEYEEM SEMKEGKACK QHVSQGIFMT QPATTIEAFS DEEVEIPEEK EGAEDSKGNG   600
IEEQEVEANE ENVKVHGGRK EKTEILSDDL TDKAEYSASH SQIVSV                  646

SEQ ID NO: 112          moltype = AA  length = 1152
FEATURE                 Location/Qualifiers
source                  1..1152
                        mol_type = protein
                        organism = Homo sapiens
SEQUENCE: 112
MREPEELMPD SGAVFTFGKS KFAENNPGKF WFKNDVPVHL SCGDEHSAVV TGNNKLYMFG    60
SNNWGQLGLG SKSAISKPTC VKALKPEKVK LAACGRNHTL VSTEGGNVYA TGGNNEGQLG   120
LGDTEERNTF HVISFFTSEH KIKQLSAGSN TSAALTEDGR LFMWGDNSEG QIGLKNVSNV   180
CVPQQVTIGK PVSWISCGYY HSAFVTTDGE LYVFGEPENG KLGLPNQLLG NHRTPQLVSE   240
```

```
IPEKVIQVAC GGEHTVVLTE NAVYTFGLGQ FGQLGLGTFL FETSEPKVIE NIRDQTISYI    300
SCGENHTALI TDIGLMYTFG DGRHGKLGLG LENFTNHFIP TLCSNFLRFI VKLVACGGCH    360
MVVFAAPHRG VAKEIEFDEI NDTCLSVATF LPYSSLTSGN VLQRTLSARM RRRERERSPD    420
SFSMRRTLPP IEGTLGLSAC FLPNSVFPRC SERNLQESVL SEQDLMQPEE PDYLLDEMTK    480
EAEIDNSSTV ESLGETTDIL NMTHIMSLNS NEKSLKLSPV QKQKKQQTIG ELTQDTALTE    540
NDDSDEYEEM SEMKEGKACK QHVSQGIFMT QPATTIEAFS DEEVEIPEEK EGAEDSKGNG    600
IEEQEVEANE ENVKVHGGRK EKTEILSDDL TDKAEVSEGK AKSVGEAEDG PEGRGDGTCE    660
EGSSGAEHWQ DEEREKGEKD KGRGEMERPG EGEKELAEKE EWKKRDGEEQ EQKEREQGHQ    720
KERNQEMEEG GEEEHGEGEE EEGDREEEEE KEGEGKEGGE GEEVEGEEKE EGERKKEER    780
AGKEEKGEEE GDQGEGEEEE TEGRGEEKEE GGEVEGGEVE EGKGEREEEE EEGEGEEEEG    840
EGEEEEGEGE EEEGEGEKGEE EGEGEGEGEE GEEGEGEGEE EEGEGEGEEE GEGEEEEEG    900
EGEGEEEEG EGEEEEGEGK GEEEGEEGEG EGEEEEGEGE GEDGEGEGEE EEGEWEGEEE    960
EGEGEEEEG EGEGEEEGGE EGEGEEGEGE EGEEEEGEGE EEGEGEEEEE GEGEEEEEG   1020
VEGEVEGEEG EGEGEEEEGE EEGEERKEKEG EGEENRRNRE EEEEEGKYQ ETGEEENERQ   1080
DGEEYKKVSK IKGSVKYGKH KTYQKKSVTN TQGNGKEQRS KMPVQSKRLL KNGPSGSKKF   1140
WNNVLPHYLE LK                                                     1152

SEQ ID NO: 113          moltype = AA  length = 1020
FEATURE                 Location/Qualifiers
source                  1..1020
                        mol_type = protein
                        organism = Homo sapiens
SEQUENCE: 113
MREPEELMPD SGAVFTFGKS KFAENNPGKF WFKNDVPVHL SCGDEHSAVV TGNNKLYMFG     60
SNNWGQLGLG SKSAISKPTC VKALKPEKVK LAACGRNHTL VSTEGGNVYA TGGNNEGQLG    120
LGDTEERNTF HVISFFTSEH KIKQLSAGSN TSAALTEDGR LFMWGDNSEG QIGLKNVSNV    180
CVPQQVTIGK PVSWISCGYY HSAFVTTDGE LYVFGEPENG KLGLPNQLLG NHRTPQLVSE    240
IPEKVIQVAC GGEHTVVLTE NAVYTFGLGQ FGQLGLGTFL FETSEPKVIE NIRDQTISYI    300
SCGENHTALI TDIGLMYTFG DGRHGKLGLG LENFTNHFIP TLCSNFLRFI VKLVACGGCH    360
MVVFAAPHRG VAKEIEFDEI NDTCLSVATF LPYSSLTSGN VLQRTLSARM RRRERERSPD    420
SFSMRRTLPP IEGTLGLSAC FLPNSVFPRC SERNLQESVL SEQDLMQPEE PDYLLDEMTK    480
EAEIDNSSTV ESLGETTDIL NMTHIMSLNS NEKSLKLSPV QKQKKQQTIG ELTQDTALTE    540
NDDSDEYEEM SEMKEGKACK QHVSQGIFMT QPATTIEAFS DEEVGNDTGQ VGPQADTDGE    600
GLQKEVYRHE NNNGVDQLDA KEIEKESDGG HSQKESEAEE IDSEKETKLA EIAGMKDLRE    660
REKSTKKMSP FFGNLPDRGM NTESEENKDF VKKRESCKQD VIFDSERESV EKPDSYMEGA    720
SESQQGIADG FQQPEAIEFS SGEKEDDEVE TDQNIRYGRK LIEQGNEKET KPIISKSMAK    780
YDFKCDRLSE IPEEKEGAED SKGNGIEEQE VEANEENVKV HGGRKEKTEI LSDDLTDKAE    840
DHEFSKTEEL KLEDVDEEIN AENVESKKKT VGDDESVPTG YHSKTEGAER TNDDSSAETI    900
EKKEKANLEE RAICEYNENP KGYMLDDADS SSLEILENSE TTPSKDMKKT KKIFLFKRVP    960
SINQKIVKNN NEPLPEIKSI GDQIILKSDN KDADQNHMSQ NHQNIPPTNT ERRSKSCTIL   1020

SEQ ID NO: 114          moltype = AA  length = 734
FEATURE                 Location/Qualifiers
source                  1..734
                        mol_type = protein
                        organism = Adeno-associated virus - 4
SEQUENCE: 114
MTDGYLPDWL EDNLSEGVRE WWALQPGAPK PKANQQHQDN ARGLVLPGYK YLGPGNGLDK     60
GEPVNAADAA ALEHDKAYDQ QLKAGDNPYL KYNHADAEFQ QRLQGDTSFG GNLGRAVFQA    120
KKRVLEPLGL VEQAGETAPG KKRPLIESPQ QPDSSTGIGK GKQPAKKKL VFEDETGAGD    180
GPPEGSTSGA MSDDSEMRAA AGGAAVEGGQ GADGVGNASG DWHCDSTWSE GHVTTTSTRT    240
WVLPTYNNHL YKRLGESLQS NTYNGFSTPW GYFDFNRFHC HFSPRDWQRL INNNWGMRPK    300
AMRVKIFNIQ VKEVTTSNGE TTVANNLTST VQIFADSSYE LPYVMDAGQE GSLPPFPNDV    360
FMVPQYGYCG LVTGNTSQQQ TDRNAFYCLE YFPSQMLRTG NNFEITYSFE KVPFHSMYAH    420
SQSLDRLMNP LIDQYLWGLQ STTTGTTLNA GTATTNFTKL RPTNFSNFKK NWLPGPSIKQ    480
QGFSKTANQN YKIPATGSDS LIKYETHSTL DGRWSALTPG PPMATAGPAD SKFSNSQLIF    540
AGPKQNGNTA TVPGTLIFTS EEELAATNAT DTDMWGNLPG GDQSNSNLPT VDRLTALGAV    600
PGMVWQNRDI YYQGPIWAKI PHTDGHFHPS PLIGGFGLKH PPPQIFIKNT PVPANPATTF    660
SSTPVNSFIT QYSTGQVSVQ IDWEIQKERS KRWNPEVQFT SNYGQQNSLL WAPDAAGKYT    720
EPRAIGTRYL THHL                                                    734

SEQ ID NO: 115          moltype = AA  length = 737
FEATURE                 Location/Qualifiers
VARIANT                 264
                        note = Xaa can be any naturally occurring amino acid
VARIANT                 266
                        note = Xaa can be any naturally occurring amino acid
VARIANT                 268
                        note = Xaa can be any naturally occurring amino acid
VARIANT                 448
                        note = Xaa can be any naturally occurring amino acid
VARIANT                 459..460
                        note = Xaa can be any naturally occurring amino acid
VARIANT                 467
                        note = Xaa can be any naturally occurring amino acid
VARIANT                 470..471
                        note = Xaa can be any naturally occurring amino acid
VARIANT                 474
                        note = Xaa can be any naturally occurring amino acid
```

| | | |
|---|---|---|
| VARIANT | 495 | |
| | note = Xaa can be any naturally occurring amino acid | |
| VARIANT | 516 | |
| | note = Xaa can be any naturally occurring amino acid | |
| VARIANT | 533 | |
| | note = Xaa can be any naturally occurring amino acid | |
| VARIANT | 547 | |
| | note = Xaa can be any naturally occurring amino acid | |
| VARIANT | 551 | |
| | note = Xaa can be any naturally occurring amino acid | |
| VARIANT | 555 | |
| | note = Xaa can be any naturally occurring amino acid | |
| VARIANT | 557 | |
| | note = Xaa can be any naturally occurring amino acid | |
| VARIANT | 561 | |
| | note = Xaa can be any naturally occurring amino acid | |
| VARIANT | 563 | |
| | note = Xaa can be any naturally occurring amino acid | |
| VARIANT | 577 | |
| | note = Xaa can be any naturally occurring amino acid | |
| VARIANT | 583 | |
| | note = Xaa can be any naturally occurring amino acid | |
| VARIANT | 593 | |
| | note = Xaa can be any naturally occurring amino acid | |
| VARIANT | 596 | |
| | note = Xaa can be any naturally occurring amino acid | |
| VARIANT | 661..662 | |
| | note = Xaa can be any naturally occurring amino acid | |
| VARIANT | 664..665 | |
| | note = Xaa can be any naturally occurring amino acid | |
| VARIANT | 710 | |
| | note = Xaa can be any naturally occurring amino acid | |
| VARIANT | 717..719 | |
| | note = Xaa can be any naturally occurring amino acid | |
| VARIANT | 723 | |
| | note = Xaa can be any naturally occurring amino acid | |
| source | 1..737 | |
| | mol_type = protein | |
| | organism = Ancestral Adeno-associated virus | |

SEQUENCE: 115
```
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPAKK RLNFGQTGDS  180
ESVPDPQPLG EPPAGPSGLG SGTMAAGGGA PMADNNEGAD GVGNASGNWH CDSTWLGDRV  240
ITTSTRTWAL PTYNNHLYKQ ISSXSXGXTN DNHYFGYSTP WGYFDFNRFH CHFSPRDWQR  300
LINNNWGFRP KRLNFKLFNI QVKEVTTNDG VTTIANNLTS TVQVFSDSEY QLPYVLGSAH  360
QGCLPPPPAD VFMIPQYGYL TLNNGSQAVG RSSFYCLEYF PSQMLRTGNN FTFSYTFEDV  420
PFHSSYAHSQ SLDRLMNPLI DQYLYYLXRT QSTGGTAGXX ELLFSQGPX XMSXQAKNWL  480
PGPCYRQQRV SKTLXQNNNS NFAWTGATKY HLNGRXSLVN PGVAMATHKD DEXRFFPSSG  540
VLIFGKXGAG XNNTXLXNVM XTXEEEIKTT NPVATEXYGV VAXNLQSSNT APXTGXVNSQ  600
GALPGMVWQN RDVYLQGPIW AKIPHTDGNF HPSPLMGGFG LKHPPPQILI KNTPVPANPP  660
XXFXXAKFAS FITQYSTGQV SVEIEWELQK ENSKRWNPEI QYTSNYAKSX NVDFAVXXXG  720
VYXEPRPIGT RYLTRNL                                                737
```

| | | |
|---|---|---|
| SEQ ID NO: 116 | moltype = AA   length = 16 | |
| FEATURE | Location/Qualifiers | |
| source | 1..16 | |
| | mol_type = protein | |
| | organism = synthetic construct | |

SEQUENCE: 116
LQRGVRIPSV LEVNGQ                                                  16

| | | |
|---|---|---|
| SEQ ID NO: 117 | moltype = AA   length = 10 | |
| FEATURE | Location/Qualifiers | |
| source | 1..10 | |
| | mol_type = protein | |
| | organism = synthetic construct | |

SEQUENCE: 117
LALIQDSMRA                                                         10

| | | |
|---|---|---|
| SEQ ID NO: 118 | moltype = AA   length = 16 | |
| FEATURE | Location/Qualifiers | |
| source | 1..16 | |
| | mol_type = protein | |
| | organism = synthetic construct | |

SEQUENCE: 118
LQRGVRIPSV LEVNGQ                                                  16

| | | |
|---|---|---|
| SEQ ID NO: 119 | moltype = AA   length = 10 | |

```
FEATURE                 Location/Qualifiers
source                  1..10
                        mol_type = protein
                        organism = synthetic construct
SEQUENCE: 119
LTHQDTTKNA                                                                      10

SEQ ID NO: 120          moltype = AA  length = 10
FEATURE                 Location/Qualifiers
source                  1..10
                        mol_type = protein
                        organism = synthetic construct
SEQUENCE: 120
QAHQDTTKNA                                                                      10

SEQ ID NO: 121          moltype = AA  length = 10
FEATURE                 Location/Qualifiers
source                  1..10
                        mol_type = protein
                        organism = synthetic construct
SEQUENCE: 121
LAHQDTTKNA                                                                      10

SEQ ID NO: 122          moltype = AA  length = 10
FEATURE                 Location/Qualifiers
source                  1..10
                        mol_type = protein
                        organism = synthetic construct
SEQUENCE: 122
LANQEHVKNA                                                                      10

SEQ ID NO: 123          moltype = AA  length = 17
FEATURE                 Location/Qualifiers
source                  1..17
                        mol_type = protein
                        organism = synthetic construct
SEQUENCE: 123
NGAVADYTRG LSPATGT                                                              17

SEQ ID NO: 124          moltype = AA  length = 17
FEATURE                 Location/Qualifiers
source                  1..17
                        mol_type = protein
                        organism = synthetic construct
SEQUENCE: 124
TGLDATRDHG LSPVTGT                                                              17

SEQ ID NO: 125          moltype = AA  length = 16
FEATURE                 Location/Qualifiers
source                  1..16
                        mol_type = protein
                        organism = synthetic construct
SEQUENCE: 125
LQKADRQPGV VVVNCQ                                                               16

SEQ ID NO: 126          moltype = AA  length = 16
FEATURE                 Location/Qualifiers
source                  1..16
                        mol_type = protein
                        organism = synthetic construct
SEQUENCE: 126
LQRGNRPVTT ADVNTQ                                                               16

SEQ ID NO: 127          moltype = AA  length = 10
FEATURE                 Location/Qualifiers
source                  1..10
                        mol_type = protein
                        organism = synthetic construct
SEQUENCE: 127
PAPQDTTKKA                                                                      10

SEQ ID NO: 128          moltype = AA  length = 16
FEATURE                 Location/Qualifiers
source                  1..16
                        mol_type = protein
                        organism = synthetic construct
SEQUENCE: 128
LQKNARPAST ESVNFQ                                                               16
```

| | | |
|---|---|---|
| SEQ ID NO: 129 | moltype = AA length = 17 | |
| FEATURE | Location/Qualifiers | |
| source | 1..17 | |
| | mol_type = protein | |
| | organism = synthetic construct | |
| SEQUENCE: 129 | | |
| TGGDPTRGTG LSPVTGA | | 17 |
| | | |
| SEQ ID NO: 130 | moltype = AA length = 17 | |
| FEATURE | Location/Qualifiers | |
| source | 1..17 | |
| | mol_type = protein | |
| | organism = synthetic construct | |
| SEQUENCE: 130 | | |
| TGSDGTRDHG LSPVTWT | | 17 |
| | | |
| SEQ ID NO: 131 | moltype = AA length = 12 | |
| FEATURE | Location/Qualifiers | |
| source | 1..12 | |
| | mol_type = protein | |
| | organism = synthetic construct | |
| SEQUENCE: 131 | | |
| TGVMHSQASG LS | | 12 |
| | | |
| SEQ ID NO: 132 | moltype = AA length = 12 | |
| FEATURE | Location/Qualifiers | |
| source | 1..12 | |
| | mol_type = protein | |
| | organism = synthetic construct | |
| SEQUENCE: 132 | | |
| TGGHDSSLDG LS | | 12 |
| | | |
| SEQ ID NO: 133 | moltype = AA length = 10 | |
| FEATURE | Location/Qualifiers | |
| source | 1..10 | |
| | mol_type = protein | |
| | organism = synthetic construct | |
| SEQUENCE: 133 | | |
| LALGETTRPA | | 10 |
| | | |
| SEQ ID NO: 134 | moltype = AA length = 10 | |
| FEATURE | Location/Qualifiers | |
| source | 1..10 | |
| | mol_type = protein | |
| | organism = synthetic construct | |
| SEQUENCE: 134 | | |
| LAPDSTTRSA | | 10 |
| | | |
| SEQ ID NO: 135 | moltype = AA length = 12 | |
| FEATURE | Location/Qualifiers | |
| source | 1..12 | |
| | mol_type = protein | |
| | organism = synthetic construct | |
| SEQUENCE: 135 | | |
| TVVSTQAGIG LS | | 12 |
| | | |
| SEQ ID NO: 136 | moltype = AA length = 10 | |
| FEATURE | Location/Qualifiers | |
| VARIANT | 3 | |
| | note = The amino acid at position 3 may also be Asn. | |
| VARIANT | 4 | |
| | note = The amino acid at position 4 may also be Gln. | |
| VARIANT | 6 | |
| | note = The amino acid at position 6 may also be His. | |
| VARIANT | 7 | |
| | note = The amino acid at position 7 may also be Val. | |
| VARIANT | 8 | |
| | note = The amino acid at position 8 may also be Lys. | |
| VARIANT | 9 | |
| | note = The amino acid at position 9 may also be Asn. | |
| source | 1..10 | |
| | mol_type = protein | |
| | organism = synthetic construct | |
| SEQUENCE: 136 | | |
| LALIZDSMRA | | 10 |
| | | |
| SEQ ID NO: 137 | moltype = AA length = 12 | |
| FEATURE | Location/Qualifiers | |
| VARIANT | 2 | |

```
                        note = X at position 2 is G, V or S.
VARIANT                 3
                        note = X at position 3 is V, E, P, G, D, M, A, or S
VARIANT                 4
                        note = X at position 4 is M, V, Y, H, G, S, or D
VARIANT                 5
                        note = X at position 5 is R, D, S, G, V, Y, T, H, or M
VARIANT                 6
                        note = X at position 6 is S, L, G, T, Q, P, or A
VARIANT                 7
                        note = X at position 7 is T, A, S, M, D, Q, or H
VARIANT                 8
                        note = X at position 8 is N, G, S, L, M, P, G, or A
VARIANT                 9
                        note = X at position 9 is S, G, D, N, A, I, P, or T
VARIANT                 12
                        note = The amino acid at position 12 may also be Asn.
source                  1..12
                        mol_type = protein
                        organism = synthetic construct
SEQUENCE: 137
TXXXXXXXXG LS                                                                   12

SEQ ID NO: 138          moltype = AA  length = 12
FEATURE                 Location/Qualifiers
VARIANT                 3
                        note = Xaa at position 3 is V, E, P, G, D, M, A, or S.
VARIANT                 4
                        note = Xaa at position 4 is M, V, Y, H, G, S, or D.
VARIANT                 5
                        note = Xaa at position 5 is R, D, S, G, V, Y, T, H, or M.
VARIANT                 6
                        note = Xaa at position 6 is S, L, G, T, Q, P, or A
VARIANT                 7
                        note = Xaa at position 7 is T, A, S, M, D, Q, or H
VARIANT                 8
                        note = Xaa at position 8 is N, G, S, L, M, P, G, or A
VARIANT                 9
                        note = Xaa at position 9 is S, G, D, N, A, I, P, or T
source                  1..12
                        mol_type = protein
                        organism = synthetic construct
SEQUENCE: 138
TGXXXXXXXG LS                                                                   12

SEQ ID NO: 139          moltype = AA  length = 17
FEATURE                 Location/Qualifiers
VARIANT                 1
                        note = Xaa at position 1 is T or N.
VARIANT                 3
                        note = Xaa at position 3 is L, S, A, or G.
VARIANT                 4
                        note = Xaa at position 4 is D or V.
VARIANT                 5
                        note = Xaa at position 5 is A, G, or P.
VARIANT                 6
                        note = Xaa at position 6 is T or D.
VARIANT                 7
                        note = Xaa at position 7 is R or Y
VARIANT                 8
                        note = Xaa at position 8 is D, T, or G
VARIANT                 9
                        note = Xaa at position 9 is H, R, or T.
source                  1..17
                        mol_type = protein
                        organism = synthetic construct
VARIANT                 14
                        note = Xaa at position 14 is V or A.
VARIANT                 16
                        note = Xaa at position 16 is G or W.
VARIANT                 17
                        note = Xaa at position 17 is T or A.
SEQUENCE: 139
XGXXXXXXXG LSPXTXX                                                              17

SEQ ID NO: 140          moltype = AA  length = 17
FEATURE                 Location/Qualifiers
VARIANT                 3
                        note = Xaa at position 3 is L, S, A, or G.
```

```
                            VARIANT              5
                                                 note = Xaa at position 5 is A, G, or P.
                            VARIANT              8
                                                 note = Xaa at position 8 is D, T, or G.
                            VARIANT              9
                                                 note = Xaa at position 9 is H, R, or T.
                            source               1..17
                                                 mol_type = protein
                                                 organism = synthetic construct
                            SEQUENCE: 140
                            TGXDXTRXXG LSPVTGT                                                              17

SEQ ID NO: 141       moltype = AA  length = 16
                            FEATURE              Location/Qualifiers
                            VARIANT              3
                                                 note = Xaa at position 3 is K or R.
                            VARIANT              4
                                                 note = Xaa at position 4 is N, G, or A.
                            VARIANT              5
                                                 note = Xaa at position 5 is A, V, N, or D.
                            VARIANT              7
                                                 note = Xaa at position 7 is P, I, or Q.
                            VARIANT              8
                                                 note = Xaa at position 8 is A, P, or V.
                            VARIANT              9
                                                 note = Xaa at position 9 is S, T, or G.
                            VARIANT              10
                                                 note = Xaa at position 10 is T or V.
                            VARIANT              11
                                                 note = Xaa at position 11 is E, L, A, or V.
                            VARIANT              12
                                                 note = Xaa at position 12 is S, E, D, or V.
                            VARIANT              15
                                                 note = Xaa at position 15 is F, G, T, or C.
                            source               1..16
                                                 mol_type = protein
                                                 organism = synthetic construct
                            SEQUENCE: 141
                            LQXXXRXXXX XXVNXQ                                                               16

SEQ ID NO: 142       moltype = AA  length = 15
                            FEATURE              Location/Qualifiers
                            source               1..15
                                                 mol_type = protein
                                                 organism = synthetic construct
                            VARIANT              5
                                                 note = The amino acid at position 5 may also be Asn.
                            VARIANT              6
                                                 note = The amino acid at position 6 may also be Gln.
                            VARIANT              8
                                                 note = The amino acid at position 8 may also be His.
                            VARIANT              9
                                                 note = The amino acid at position 9 may also be Val.
                            VARIANT              10
                                                 note = The amino acid at position 10 may also be Lys.
                            VARIANT              11
                                                 note = The amino acid at position 11 may also be Asn.
                            SEQUENCE: 142
                            TGLALIZDSM RAGLS                                                                15

SEQ ID NO: 143       moltype = AA  length = 13
                            FEATURE              Location/Qualifiers
                            source               1..13
                                                 mol_type = protein
                                                 organism = synthetic construct
                            VARIANT              5
                                                 note = The amino acid at position 5 may also be Asn.
                            VARIANT              6
                                                 note = The amino acid at position 6 may also be Gln.
                            VARIANT              8
                                                 note = The amino acid at position 8 may also be His.
                            VARIANT              9
                                                 note = The amino acid at position 9 may also be Val.
                            VARIANT              10
                                                 note = The amino acid at position 10 may also be Lys.
                            VARIANT              11
                                                 note = The amino acid at position 11 may also be Asn.
                            SEQUENCE: 143
                            LALALIZDSM RAA                                                                  13
```

```
SEQ ID NO: 144          moltype = AA  length = 15
FEATURE                 Location/Qualifiers
source                  1..15
                        mol_type = protein
                        organism = synthetic construct
VARIANT                 5
                        note = X at position 5 is V, E, P, G, D, M, A, or S.
VARIANT                 6
                        note = X at position 6 is M, V, Y, H, G, S, or D.
VARIANT                 7
                        note = X at position 7 is R, D, S, G, V, Y, T, H, or M.
VARIANT                 8
                        note = X at position 8 is S, L, G, T, Q, P, or A.
VARIANT                 9
                        note = X at position 9 is T, A, S, M, D, Q, or H.
VARIANT                 10
                        note = X at position 10 is N, G, S, L, M, P, G, or A.
VARIANT                 11
                        note = X at position 11 is S, G, D, N, A, I, P, or T.
VARIANT                 14
                        note = X at position 14 can be S or N.
SEQUENCE: 144
LATXXXXXXX XGLXA                                                             15

SEQ ID NO: 145          moltype = AA  length = 15
FEATURE                 Location/Qualifiers
source                  1..15
                        mol_type = protein
                        organism = synthetic construct
VARIANT                 5
                        note = X at position 5 is V, E, P, G, D, M, A, or S.
VARIANT                 6
                        note = X at position 6 is M, V, Y, H, G, S, or D.
VARIANT                 7
                        note = X at position 7 is R, D, S, G, V, Y, T, H, or M.
VARIANT                 8
                        note = X at position 8 is S, L, G, T, Q, P, or A.
VARIANT                 9
                        note = X at position 9 is T, A, S, M, D, Q, or H.
VARIANT                 10
                        note = X at position 10 is N, G, S, L, M, P, G, or A.
VARIANT                 11
                        note = X at position 11 is S, G, D, N, A, I, P, or T.
SEQUENCE: 145
LATGXXXXXX XGLSA                                                             15

SEQ ID NO: 146          moltype = AA  length = 20
FEATURE                 Location/Qualifiers
source                  1..20
                        mol_type = protein
                        organism = synthetic construct
VARIANT                 3
                        note = X at position 3 is T or N.
VARIANT                 5
                        note = X at position 5 is L, S, A, or G.
VARIANT                 6
                        note = X at position 6 is D or V.
VARIANT                 7
                        note = X at position 7 is A, G, or P.
VARIANT                 8
                        note = X at position 8 is T or D.
VARIANT                 9
                        note = X at position 9 is R or Y.
VARIANT                 10
                        note = X at position 10 is D, T, or G.
VARIANT                 11
                        note = X at position 11 is H, R, or T.
VARIANT                 16
                        note = X at position 16 is V or A.
VARIANT                 18
                        note = X at position 18 is G or W.
VARIANT                 19
                        note = X at position 19 is T or A.
SEQUENCE: 146
LAXGXXXXXX XGLSPXTXXA                                                        20

SEQ ID NO: 147          moltype = AA  length = 20
FEATURE                 Location/Qualifiers
```

```
source                   1..20
                         mol_type = protein
                         organism = synthetic construct
VARIANT                  5
                         note = X at position 5 is L, S, A, or G.
VARIANT                  7
                         note = X at position 7 is A, G, or P.
VARIANT                  10
                         note = X at position 10 is D, T, or G.
VARIANT                  11
                         note = X at position 11 is H, R, or T.
SEQUENCE: 147
LATGXDXTRX XGLSPVTGTA                                              20

SEQ ID NO: 148           moltype = AA  length = 20
FEATURE                  Location/Qualifiers
source                   1..20
                         mol_type = protein
                         organism = synthetic construct
VARIANT                  5
                         note = X at position 5 is K or R.
VARIANT                  6
                         note = X at position 6 is N, G, or A.
VARIANT                  7
                         note = X at position 7 is A, V, N, or D.
VARIANT                  8
                         note = X at position 8 is P, I, or Q.
VARIANT                  9
                         note = X at position 9 is A, P, or V.
VARIANT                  11
                         note = X at position 11 is S, T, or G.
VARIANT                  12
                         note = X at position 12 is T or V.
VARIANT                  13
                         note = X at position 13 is E, L, A, or V.
VARIANT                  14
                         note = X at position 14 is S, E, D, or V.
VARIANT                  17
                         note = X at position 17 is F, G, T, or C.
SEQUENCE: 148
LALQXXXRXX XXXXXVNXQA                                              20

SEQ ID NO: 149           moltype = AA  length = 13
FEATURE                  Location/Qualifiers
source                   1..13
                         mol_type = protein
                         organism = synthetic construct
VARIANT                  5
                         note = The amino acid at position 5 may also be Asn.
VARIANT                  6
                         note = The amino acid at position 6 may also be Gln.
VARIANT                  8
                         note = The amino acid at position 8 may also be His.
VARIANT                  9
                         note = The amino acid at position 9 may also be Val.
VARIANT                  10
                         note = The amino acid at position 10 may also be Lys.
VARIANT                  11
                         note = The amino acid at position 11 may also be Asn.
SEQUENCE: 149
LQLALIZDSM RAQ                                                     13

SEQ ID NO: 150           moltype = AA  length = 15
FEATURE                  Location/Qualifiers
source                   1..15
                         mol_type = protein
                         organism = synthetic construct
VARIANT                  5
                         note = X at position 5 is V, E, P, G, D, M, A, or S.
VARIANT                  6
                         note = X at position 6 is M, V, Y, H, G, S, or D.
VARIANT                  7
                         note = X at position 7 is R, D, S, G, V, Y, T, H, or M.
VARIANT                  8
                         note = X at position 8 is S, L, G, T, Q, P, or A.
VARIANT                  9
                         note = X at position 9 is T, A, S, M, D, Q, or H.
VARIANT                  10
                         note = X at position 10 is N, G, S, L, M, P, G, or A.
```

```
VARIANT              11
                     note = X at position 11 is S, G, D, N, A, I, P, or T.
VARIANT              14
                     note = X at position 14 can be S or N.
SEQUENCE: 150
LQTXXXXXXX XGLXQ                                                          15

SEQ ID NO: 151       moltype = AA  length = 15
FEATURE              Location/Qualifiers
source               1..15
                     mol_type = protein
                     organism = synthetic construct
VARIANT              5
                     note = X at position 5 is V, E, P, G, D, M, A, or S.
VARIANT              6
                     note = X at position 6 is M, V, Y, H, G, S, or D.
VARIANT              7
                     note = X at position 7 is R, D, S, G, V, Y, T, H, or M.
VARIANT              8
                     note = X at position 8 is S, L, G, T, Q, P, or A.
VARIANT              9
                     note = X at position 9 is T, A, S, M, D, Q, or H.
VARIANT              10
                     note = X at position 10 is N, G, S, L, M, P, G, or A.
VARIANT              11
                     note = X at position 11 is S, G, D, N, A, I, P, or T.
SEQUENCE: 151
LQTGXXXXXX XGLSQ                                                          15

SEQ ID NO: 152       moltype = AA  length = 20
FEATURE              Location/Qualifiers
source               1..20
                     mol_type = protein
                     organism = synthetic construct
VARIANT              3
                     note = X at position 3 is T or N.
VARIANT              5
                     note = X at position 5 is L, S, A, or G.
VARIANT              6
                     note = X at position 6 is D or V.
VARIANT              7
                     note = X at position 7 is A, G, or P.
VARIANT              8
                     note = X at position 8 is T or D.
VARIANT              9
                     note = X at position 9 is R or Y.
VARIANT              10
                     note = X at position 10 is D, T, or G.
VARIANT              11
                     note = X at position 11 is H, R, or T.
VARIANT              16
                     note = X at position 16 is V or A.
VARIANT              18
                     note = X at position 18 is G or W.
VARIANT              19
                     note = X at position 19 is T or A.
SEQUENCE: 152
LQXGXXXXXX XGLSPXTXXQ                                                     20

SEQ ID NO: 153       moltype = AA  length = 20
FEATURE              Location/Qualifiers
source               1..20
                     mol_type = protein
                     organism = synthetic construct
VARIANT              5
                     note = X at position 5 is L, S, A, or G.
VARIANT              7
                     note = X at position 7 is A, G, or P.
VARIANT              10
                     note = X at position 10 is D, T, or G.
VARIANT              11
                     note = X at position 11 is H, R, or T.
SEQUENCE: 153
LQTGXDXTRX XGLSPVTGTQ                                                     20

SEQ ID NO: 154       moltype = AA  length = 20
FEATURE              Location/Qualifiers
source               1..20
                     mol_type = protein
```

```
                        organism = synthetic construct
VARIANT                 5
                        note = X at position 5 is K or R.
VARIANT                 6
                        note = X at position 6 is N, G, or A.
VARIANT                 7
                        note = X at position 7 is A, V, N, or D.
VARIANT                 8
                        note = X at position 8 is P, I, or Q.
VARIANT                 9
                        note = X at position 9 is A, P, or V.
VARIANT                 11
                        note = X at position 11 is S, T, or G.
VARIANT                 12
                        note = X at position 12 is T or V.
VARIANT                 13
                        note = X at position 13 is E, L, A, or V.
VARIANT                 14
                        note = X at position 14 is S, E, D, or V.
VARIANT                 17
                        note = X at position 17 is F, G, T, or C.
SEQUENCE: 154
LQLQXXXRXX XXXXXVNXQQ                                                    20

SEQ ID NO: 155          moltype = AA  length = 17
FEATURE                 Location/Qualifiers
source                  1..17
                        mol_type = protein
                        organism = synthetic construct
VARIANT                 5
                        note = X at position 5 is V, E, P, G, D, M, A, or S.
VARIANT                 6
                        note = X at position 6 is M, V, Y, H, G, S, or D.
VARIANT                 7
                        note = X at position 7 is R, D, S, G, V, Y, T, H, or M.
VARIANT                 8
                        note = X at position 8 is S, L, G, T, Q, P, or A.
VARIANT                 9
                        note = X at position 9 is T, A, S, M, D, Q, or H.
VARIANT                 10
                        note = X at position 10 is N, G, S, L, M, P, G, or A.
VARIANT                 11
                        note = X at position 11 is S, G, D, N, A, I, P, or T.
VARIANT                 14
                        note = X at position 14 can be S or N.
SEQUENCE: 155
TGTXXXXXXX XGLXGLS                                                       17

SEQ ID NO: 156          moltype = AA  length = 17
FEATURE                 Location/Qualifiers
source                  1..17
                        mol_type = protein
                        organism = synthetic construct
VARIANT                 5
                        note = X at position 5 is V, E, P, G, D, M, A, or S.
VARIANT                 6
                        note = X at position 6 is M, V, Y, H, G, S, or D.
VARIANT                 7
                        note = X at position 7 is R, D, S, G, V, Y, T, H, or M.
VARIANT                 8
                        note = X at position 8 is S, L, G, T, Q, P, or A.
VARIANT                 9
                        note = X at position 9 is T, A, S, M, D, Q, or H.
VARIANT                 10
                        note = X at position 10 is N, G, S, L, M, P, G, or A.
VARIANT                 11
                        note = X at position 11 is S, G, D, N, A, I, P, or T.
SEQUENCE: 156
TGTGXXXXXX XGLSGLS                                                       17

SEQ ID NO: 157          moltype = AA  length = 22
FEATURE                 Location/Qualifiers
source                  1..22
                        mol_type = protein
                        organism = synthetic construct
VARIANT                 3
                        note = X at position 3 is T or N.
VARIANT                 5
                        note = X at position 5 is L, S, A, or G.
```

```
VARIANT            6
                   note = X at position 6 is D or V.
VARIANT            7
                   note = X at position 7 is A, G, or P.
VARIANT            8
                   note = X at position 8 is T or D.
VARIANT            9
                   note = X at position 9 is R or Y.
VARIANT            10
                   note = X at position 10 is D, T, or G.
VARIANT            11
                   note = X at position 11 is H, R, or T.
VARIANT            16
                   note = X at position 16 is V or A.
VARIANT            18
                   note = X at position 18 is G or W.
VARIANT            19
                   note = X at position 19 is T or A.
SEQUENCE: 157
TGXGXXXXXX XGLSPXTXXG LS                                                        22

SEQ ID NO: 158     moltype = AA  length = 22
FEATURE            Location/Qualifiers
source             1..22
                   mol_type = protein
                   organism = synthetic construct
VARIANT            5
                   note = X at position 5 is L, S, A, or G.
VARIANT            7
                   note = X at position 7 is A, G, or P.
VARIANT            10
                   note = X at position 10 is D, T, or G.
VARIANT            11
                   note = X at position 11 is H, R, or T.
SEQUENCE: 158
TGTGXDXTRX XGLSPVTGTG LS                                                        22

SEQ ID NO: 159     moltype = AA  length = 22
FEATURE            Location/Qualifiers
source             1..22
                   mol_type = protein
                   organism = synthetic construct
VARIANT            5
                   note = X at position 5 is K or R.
VARIANT            6
                   note = X at position 6 is N, G, or A.
VARIANT            7
                   note = X at position 7 is A, V, N, or D.
VARIANT            8
                   note = X at position 8 is P, I, or Q.
VARIANT            9
                   note = X at position 9 is A, P, or V.
VARIANT            11
                   note = X at position 11 is S, T, or G.
VARIANT            12
                   note = X at position 12 is T or V.
VARIANT            13
                   note = X at position 13 is E, L, A, or V.
VARIANT            14
                   note = X at position 14 is S, E, D, or V.
VARIANT            17
                   note = X at position 17 is F, G, T, or C.
SEQUENCE: 159
TGLQXXXRXX XXXXXVNXQG LS                                                        22
```